United States Patent [19]
Rorer

[11] Patent Number: 4,764,205

[45] Date of Patent: Aug. 16, 1988

[54] HERBICIDAL SULFONAMIDES

[75] Inventor: Morris P. Rorer, Newark, Del.

[73] Assignee: E. I. Du Pont de Nemours and Company, Wilmington, Del.

[21] Appl. No.: 67,725

[22] Filed: Jun. 19, 1987

Related U.S. Application Data

[60] Division of Ser. No. 842,791, Mar. 27, 1986, Pat. No. 4,699,647, which is a continuation-in-part of Ser. No. 739,215, May 30, 1985, abandoned.

[51] Int. Cl.$^4$ .................. C07D 401/14; C07D 403/14; C07D 409/14; A01N 43/66
[52] U.S. Cl. ............................................. 71/93; 71/86; 71/87; 71/90; 544/113; 544/212; 544/198; 544/207; 544/209; 544/195; 544/219
[58] Field of Search .................. 71/90, 93, 86, 87; 544/113, 212, 198, 207, 209, 195, 219

[56] References Cited

U.S. PATENT DOCUMENTS

| | | | |
|---|---|---|---|
| 4,127,405 | 11/1978 | Levitt | 71/93 |
| 4,169,719 | 10/1979 | Levitt | 71/90 |
| 4,460,401 | 7/1984 | Sauers | 71/92 |
| 4,465,505 | 8/1984 | Wolf | 71/92 |
| 4,475,944 | 10/1984 | Rorer | 71/90 |
| 4,534,790 | 8/1985 | Wolf | 71/93 |
| 4,602,940 | 7/1986 | Wolf | 71/92 |
| 4,655,817 | 4/1987 | Thompson | 71/90 |
| 4,657,578 | 4/1987 | Thompson | 71/90 |

FOREIGN PATENT DOCUMENTS 116518 8/1984 European Pat. Off.
83/8416 11/1983 South Africa.

*Primary Examiner*—John M. Ford

[57] ABSTRACT

This invention relates to herbicidal benzene sulfonamides containing a five or six membered heterocyclic ring consisting of 2–3 heteroatoms and 1–2 carbonyl groups as a substituent on benzene.

41 Claims, No Drawings

HERBICIDAL SULFONAMIDES

This application is a divisional of my copending application U.S. Ser. No. 842,791, filed Mar. 27, 1986, now U.S. Pat No. 4,699,647, which was a continuation-in-part of my then copending application U.S. Ser. No. 739,215, filed May 30, 1985, now abandoned.

BACKGROUND OF THE INVENTION

This invention relates to herbicidal benzenesulfonamides containing a five or six membered heterocyclic ring consisting of 2–3 heteroatoms and 1–2 carbonyl groups as a substituent on benzene, suitable compositions thereof, and their use as agricultural chemicals.

U.S. Pat. No. 4,127,405 and U.S. Pat. No. 4,169,719 disclose herbicidal benzenesulfonylureas.

European Patent Application (EP-A) No. 83,975 (published July 20, 1983) discloses herbicidal benzenesulfonamides of formula

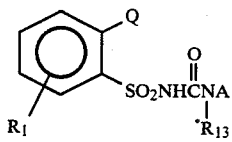

wherein

Q is selected from various five or six-membered aromatic or partially unsaturated heterocyclic rings containing 2 or 3 heteroatoms selected from O, S or NR.

European Patent Application (EP-A) No. 85,476 (published Aug. 10, 1983) discloses herbicidal benzenesulfonamides of formula

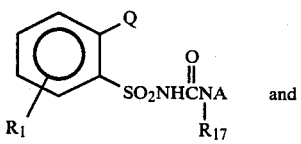 and

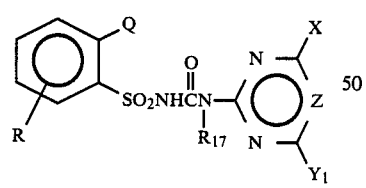

wherein

Q is selected from various 5-membered aromatic heterocycles, and their dihydro and tetrahydro analogs, which contain one heteroatom selected from O, S or NR, or Q is a saturated or partially unsaturated 6-membered ring containing one heteroatom selected from O or S; and $Q^1$ is a 6-membered aromatic heterocycle containing one to three N atoms.

South African Patent Application No. 83/8416 (published May 12, 1984) discloses herbicidal benzenesulfonamides of formula

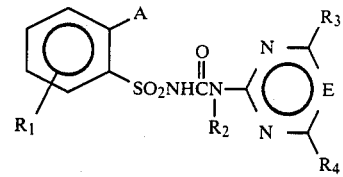

wherein

A is an unsaturated or only partially saturated 5- or 6-membered heterocyclic ring system which is bonded through a carbon atom and contains 1, 2 or 3 heteroatoms.

European Patent Application No. 116,518 (Swiss priority 2/4/83, published 8/22/84) discloses herbicidal sulfonamides of formula

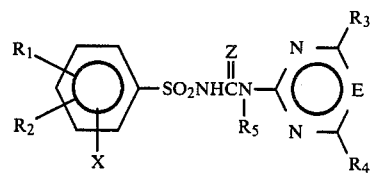

wherein

X is $NR_6R_7$, $N(SO_2R_9)_2$ or $$N \begin{matrix} A \\ \\ (C)_n \end{matrix} B;$$

A is CO, $SO_2$, $CONR_{23}$ or $CO_2$;
B is $C_1$–$C_4$ alkyl or $C_2$–$C_2$ alkenyl; and
C is CO, $CR_{21}R_{22}$ or $SO_2$.

U.S. Pat. No. 4,475,944 discloses herbicidal sulfamates, possessing an ortho-heterocyclic ring, such as those of formula

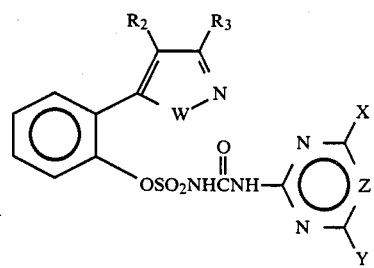

wherein

W is O, S or $NR_1$.

SUMMARY OF THE INVENTION

This invention relates to novel compounds of Formula I, agriculturally suitable compositions containing them, and their method-of-use as preemergent or postemergent herbicides or as plant growth regulants.

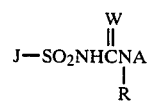

wherein

J is 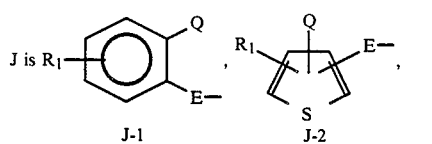

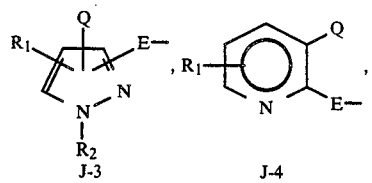

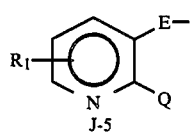

W is O or S;
R is H or CH₃;
E is a single bond, CH$_2$ or O;
Q is a saturated 5- or 6-membered heterocyclic ring, bonded through carbon or nitrogen, containing a carbonyl group and 2-3 heteroatoms selected from the group consisting of 0-2 oxygen, 0-2 sulfur or 0-2 nitrogen; a 5-membered heterocyclic ring, bonded through carbon or nitrogen, containing a carbonyl group and 2-3 heteroatoms selected from the group consisting of 0-2 oxygen, 0-2 sulfur or 1-3 nitrogen and containing one endocyclic double bond; a 6-membered heterocyclic ring, bonded through carbon or nitrogen, containing a carbonyl group and 2-3 heteroatoms selected from the group consisting of 0-2 oxygen, 0-2 sulfur or 1-3 nitrogen and containing one or two endocyclic double bonds; or a 5-membered heterocyclic ring, bonded through carbon or nitrogen, containing two adjacent carbonyl groups and 2 heteroatoms selected from the group consisting of 0-1 oxygen, 0-1 sulfur, or 1-2 nitrogen and containing one endocyclic double bond, said Q value may be substituted or unsubstituted wherein the substituent groups are selected from the group consisting of C$_1$-C$_4$ alkyl, C$_1$-C$_4$ haloalkyl, C$_3$-C$_4$ alkenyl, C$_3$-C$_4$ haloalkenyl, C$_3$-C$_4$ alkynyl, C$_3$-C$_4$ haloalkynyl, C$_1$-C$_3$ cyanoalkyl, C$_2$-C$_4$ alkoxyalkyl, C$_2$-C$_4$ alkylthioalkyl, C$_2$-C$_4$ alkylcarbonyl, C$_3$-C$_4$ alkylcarbonylalkyl, C$_1$-C$_4$ alkyl substituted with OH or NH$_2$, C$_2$-C$_4$ alkylaminoalkyl, C$_3$-C$_4$ dialkylaminoalkyl, CH$_2$CH(OCH$_3$)$_2$,

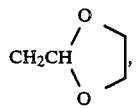

C(O)N(CH$_3$)$_2$, P(O)(OC$_1$-C$_2$ alkyl)$_2$, P(S)(OC$_1$-C$_2$ alkyl)$_2$ or C$_1$-C$_2$ alkyl substituted with C$_1$-C$_2$ alkoxycarbonyl;
R$_1$ is H, C$_1$-C$_3$ alkyl, C$_1$-C$_3$ haloalkyl, halogen, nitro, C$_1$-C$_3$ alkoxy, SO$_2$NR$_a$R$_b$, C$_1$-C$_3$ alkylthio, C$_1$-C$_3$ alkylsulfinyl, C$_1$-C$_3$ alkylsulfonyl, CH$_2$CN, CN, CO$_2$R$_c$, C$_1$-C$_3$ haloalkoxy, C$_1$-C$_3$ haloalkylthio, C$_2$-C$_4$ alkoxyalkyl, C$_2$-C$_4$ alkylthioalkyl, CH$_2$N$_3$ or NR$_d$R$_e$;

R$_a$ is H, C$_1$-C$_4$ alkyl, C$_2$-C$_3$ cyanoalkyl, methoxy or ethoxy;
R$_b$ is H, C$_1$-C$_4$ alkyl or C$_3$-C$_4$ alkenyl; or
R$_a$ and R$_b$ may be taken together as —(CH$_2$)$_3$—, —(CH$_2$)$_4$—, —(CH$_2$)$_5$— or —CH$_2$CH$_2$OCH$_2$CH$_2$—;
R$_c$ is C$_1$-C$_4$ alkyl, C$_3$-C$_4$ alkenyl, C$_3$-C$_4$ alkynyl, C$_2$-C$_4$ haloalkyl, C$_2$-C$_3$ cyanoalkyl, C$_5$-C$_6$ cycloalkyl, C$_4$-C$_7$ cycloalkylalkyl or C$_2$-C$_4$ alkoxyalkyl;
R$_d$ and R$_e$ are independently H or C$_1$-C$_2$ alkyl;

A is 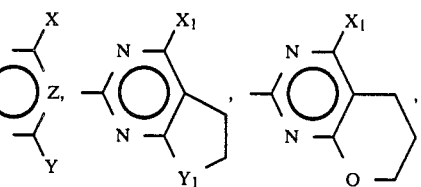

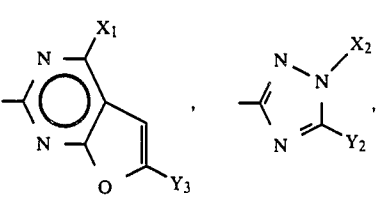

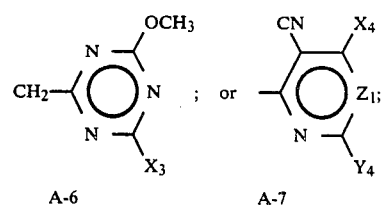

X is H, C$_1$-C$_4$ alkyl, C$_1$-C$_4$ alkoxy, C$_1$-C$_4$ haloalkoxy, C$_1$-C$_4$ haloalkyl, C$_1$-C$_4$ haloalkylthio, C$_1$-C$_4$ alkylthio, halogen, C$_2$-C$_5$ alkoxyalkyl, C$_2$-C$_5$ alkoxyalkoxy, amino, C$_1$-C$_3$ alkylamino, di(C$_1$-C$_3$ alkyl)amino or C$_3$-C$_5$ cycloalkyl;
Y is H, C$_1$-C$_4$ alkyl, C$_1$-C$_4$ alkoxy, C$_1$-C$_4$ haloalkoxy, C$_1$-C$_4$ haloalkylthio, C$_1$-C$_4$ alkylthio, C$_2$-C$_5$ alkoxyalkyl, C$_2$-C$_5$ alkoxyalkoxy, amino, C$_1$-C$_3$ alkylamino, di(C$_1$-C$_3$ alkyl)amino, C$_3$-C$_4$ alkenyloxy, C$_3$-C$_4$ alkynyloxy, C$_2$-C$_5$ alkylthioalkyl, C$_1$-C$_4$ haloalkyl, C$_2$-C$_4$ alkynyl, azido, cyano, C$_2$-C$_5$ alkylsulfinylalkyl, C$_2$-C$_5$ alkylsulfonylalkyl,

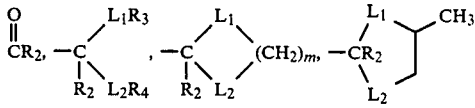

or N(OCH$_3$)CH$_3$;
m is 2 or 3;
L$_1$ and L$_2$ are independently O or S;
R$_2$ is H or C$_1$-C$_3$ alkyl;
R$_3$ and R$_4$ are independently C$_1$-C$_3$ alkyl;
Z is CH, N, CCH$_3$, CC$_2$H$_5$, CCl or CBr;
Z$_1$ is CH or N;
Y$_1$ is O or CH$_2$;
X$_1$ is CH$_3$, OCH$_3$, OC$_2$H$_5$ or OCF$_2$H;
X$_2$ is CH$_3$, C$_2$H$_5$ or CH$_2$CF$_3$;
Y$_2$ is OCH$_3$, OC$_2$H$_5$, SCH$_3$, SC$_2$H$_5$, CH$_3$ or CH$_2$CH$_3$;
X$_3$ is CH$_3$ or OCH$_3$;
Y$_3$ is H or CH$_3$;

$X_4$ is $CH_3$, $OCH_3$, $OC_2H_5$, $CH_2OCH_3$ or Cl; and
$Y_4$ is $CH_3$, $OCH_3$, $OC_2H_5$ or Cl;
and their agriculturally suitable salts; provided that (a) when Q contains 2 heteroatoms selected from 0-2 oxygen and 0-2 sulfur, said heteroatoms are not bonded directly to one another, and when Q contains 3 nitrogen heteroatoms, only two of these may be bonded directly together;

(b) when X is Cl, F, Br or I, then Z is CH and Y is $OCH_3$, $OC_2H_5$, $N(OCH_3)CH_3$, $NHCH_3$, $N(CH_3)_2$ or $OCF_2H$;

(c) when X or Y is $C_1$ haloalkoxy, then Z is CH;

(d) when J is J-2 or J-3, the substituent Q and the sulfonylurea bridge are on adjacent carbon atoms;

(e) when E is O, then J is J-1 and W is O;

(f) when W is S, then R is H, A is A-1, Z is CH or N and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or 1,3-dioxolan-2-yl;

(g) when the total number of carbons of X and Y is greater than four, then the number of carbons of $R_1$ must be less than or equal to two, and the number of carbons of the substituent on Q must be less than or equal or two;

(h) $X_4$ and $Y_4$ are not simultaneously Cl; and (i) when Q is bound through nitrogen and contains 2-heteroatoms and one carbonyl group, and said heteroatoms are bound through the carbonyl, then J is other than J-1.

Exemplary values of Q include:

Q-1, Q-2, Q-3, Q-4, Q-5, Q-6, Q-7, Q-8, Q-9, Q-10, Q-11, Q-12, Q-13, Q-14, Q-15, Q-16, Q-17, Q-18, Q-19, Q-20, Q-21, Q-22, Q-23, Q-24, Q-25, Q-26, Q-27, Q-28, Q-29, Q-30;

wherein
$R_5$ is H, $C_1-C_4$ alkyl, $CH_2CH=CH_2$, $CH_2CH=CHCH_3$, $CH_2C\equiv CH$, $CH_2C\equiv CCH_3$, $CH_2CN$, $CH_2CO_2(C_1-C_2$ alkyl), $CH(CH_3)CO_2(C_1-C_2$ alkyl), $CF_2H$, $C_2-C_3$ alkyl substituted with 1-3 atoms of F or Cl, $CH_2OCH_3$, $CH_2OCH_2CH_3$, $CH_2CH_2OCH_3$, or $CH_2CH_2OCH_2CH_3$;

$R_6$ is $C_1-C_3$ alkyl;

$R_6'$ and $R_6''$ are independently H or $C_1-C_2$ alkyl; and $R_7$ is H, $C_1-C_4$ alkyl, $C_1-C_3$ haloalkyl or $CH_2CH=CH_2$.

In the above definitions, the term "alkyl", used either alone or in compound words such as "alkylthio" or "haloalkyl", denotes straight chain or branched alkyl, e.g. methyl, ethyl, n-propyl, isopropyl or the different butyl isomers.

Alkoxy denotes methoxy, ethoxy, n-propyloxy, isopropyloxy and the different butyl isomers.

Alkenyl denotes straight chain or branched alkenes, e.g. vinyl, 1-propenyl, 2-propenyl, 3-propenyl and the different butenyl isomers.

Alkynyl denotes straight chain or branched alkynes, e.g. ethynyl, 1-propynyl, 2-propynyl and the different butynyl isomers.

Alkylsulfonyl denotes e.g. methylsulfonyl, ethylsulfonyl and the different propylsulfonyl isomers.

Alkylthio, alkylsulfinyl, alkylamino, etc. are defined analogously to the above examples.

Cycloalkyl denotes cyclopropyl, cyclobutyl, cyclopentyl and cyclohexyl.

Cycloalkylalkyl denotes, for example, cyclopropylmethyl, cyclopropylethyl and cyclohexylmethyl.

The term "halogen", either alone or in compound words such as "haloalkyl", denotes fluorine, chlorine, bromine or iodine. Further, when used in compound words such as "haloalkyl" said alkyl may be partially halogenated or fully substituted with halogen atoms which may be the same or different. Examples of haloalkyl include $CH_2CH_2F$, $CF_2CF_3$ and $CH_2CHFCl$.

Alkylcarbonyl denotes acetyl, propionyl, and the different butyryl isomers.

Alkoxycarboyl denotes methoxycarbonyl and ethoxycarbonyl.

The total number of carbon atoms in a substituent group is indicated by the $C_i$–$C_j$ prefix where i and j are numbers from 1 to 7. For example, $C_1$–$C_3$ alkylsulfonyl would designate methylsulfonyl through propylsulfonyl, $C_2$ alkoxyalkoxy would designate $OCH_2OCH_3$, $C_2$ cyanoalkyl would designate $CH_2CN$ and $C_3$ cyanoalkyl would designate $CH_2CH_2CN$ and $CH(CN)CH_3$.

Preferred for reasons of increased ease of synthesis and/or greater herbicidal efficacy are:

1. Compounds of Formula I where E is a single bond; and Z is CH or N;
2. Compounds of Formula I where E is $CH_2$, W is O and Z is CH or N;
3. Compounds of Formula I where E is O and Z is CH or N;
4. Compounds of Preferred 1 where Q is Q-1 to Q-30;
5. Compounds of Preferred 4 where
   W is O;
   R is H;
   $R_1$ is H, F, Cl, Br, $C_1$–$C_2$ alkyl, $C_1$–$C_3$ alkoxy, $C_1$–$C_3$ alkylthio, or $C_1$–$C_2$ alkyl, $C_1$–$C_3$ alkoxy or $C_1$–$C_3$ alkylthio substituted with 1–3 atoms of F, Cl or Br;
   X is $C_1$–$C_2$ alkyl, $C_1$–$C_2$ alkoxy, Cl, F, Br, I, $OCF_2H$, $CH_2F$, $CF_3$, $OCH_2CH_2F$, $OCH_2CHF_2$, $OCH_2CF_3$, $CH_2Cl$ or $CH_2Br$; and
   Y is H, $C_1$–$C_2$ alkyl, $C_1$–$C_2$ alkoxy, $CH_2OCH_3$, $CH_2OCH_2CH_3$, $NHCH_3$, $N(OCH_3)CH_3$, $N(CH_3)_2$, $CF_3$, $SCH_3$, $OCH_2CH=CH_2$, $OCH_2C\equiv CH$, $OCH_2CH_2OCH_3$, $CH_2SCH_3$,

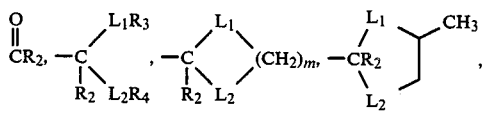

$OCF_2H$, $SCF_2H$, cyclopropyl, $OCF_2H$, $SCF_2H$, cyclopropyl, $C\equiv CH$ or $C\equiv CCH_3$;
6. Compounds of Preferred 5 where A is A-1;
7. Compounds of Preferred 6 where J is J-1;
8. Compounds of Preferred 6 where J is J-2;
9. Compounds of Preferred 6 where J is J-3;
10. Compounds of Preferred 6 where J is J-4;
11. Compounds of Preferred 6 where J is J-5;
12. Compounds of Preferred 6 where
    J is J-1;
    $R_1$ is H, Cl, $CH_3$ or $OCH_3$;
    X is $CH_3$, $OCH_3$, Cl or $OCF_2H$; and
    Y is $CH_3$, $OCH_3$, $C_2H_5$, $CH_2OCH_3$, $NHCH_3$, $CH(OCH_3)_2$ or cyclopropyl;
13. Compounds of Preferred 12 where Q is Q-1;
14. Compounds of Preferred 12 where Q is Q-2;
15. Compounds of Preferred 12 where Q is Q-3;
16. Compounds of Preferred 12 where Q is Q-4;
17. Compounds of Preferred 12 where Q is Q-5;
18. Compounds of Preferred 12 where Q is Q-6;
19. Compounds of Preferred 12 where Q is Q-7;
20. Compounds of Preferred 12 where Q is Q-8;
21. Compounds of Preferred 12 where Q is Q-9;
22. Compounds of Preferred 12 where Q is Q-10;
23. Compounds of Preferred 12 where Q is Q-11;
24. Compounds of Preferred 12 where Q is Q-12;
25. Compounds of Preferred 12 where Q is Q-13;
26. Compounds of Preferred 12 where Q is Q-14;
27. Compounds of Preferred 12 where Q is Q-15;
28. Compounds of Preferred 12 where Q is Q-16;
29. Compounds of Preferred 12 where Q is Q-17;
30. Compounds of Preferred 12 where Q is Q-18;
31. Compounds of Preferred 12 where Q is Q-19;
32. Compounds of Preferred 12 where Q is Q-21;
33. Compounds of Preferred 12 where Q is Q-22;
34. Compounds of Preferred 12 where Q is Q-23;
35. Compounds of Preferred 12 where Q is Q-24;
36. Compounds of Preferred 12 where Q is Q-25;
37. Compounds of Preferred 12 where Q is Q-26;
38. Compounds of Preferred 12 where Q is Q-27;
39. Compounds of Preferred 2 where
    R is H;
    J is J-1;
    $R_1$ is H;
    A is A-1;
    X is $CH_3$, $OCH_3$, $OCH_2CH_3$, Cl or $OCF_2H$;
    Y is $CH_3$, $OCH_3$, $C_2H_5$, $CH_2OCH_3$, $NHCH_3$, $CH(OCH_3)_2$ or cyclopropyl and Q is Q-1, Q-7, Q-10 or Q-15;
40. Compounds of Preferred 3 where
    R is H;
    J is J-1;
    $R_1$ is H;
    A is A-1;
    X is $CH_3$, $OCH_3$, $OCH_2CH_3$, Cl or $OCF_2H$;
    Y is $CH_3$, $OCH_3$, $C_2H_5$, $CH_2OCH_3$, $NHCH_3$, $CH(OCH_3)_2$ or cyclopropyl and Q is Q-1, Q-7, Q-10 or Q-15.

Specifically Preferred for reasons of greatest ease of synthesis and/or greatest herbicidal efficacy are:
2-(4,5-dihydro-4-methyl-5-oxo-1,3,4-oxadiazol-2-yl)-N-[(4,6-dimethoxypyrimidin-2-yl)aminocarbonyl]benzenesulfonamide, m.p. 208°–214° C.; and
2-(4,5-dihydro-4-methyl-5-oxo-1,3,4-oxadiazol-2-yl)-N-[(4-methoxy-6-methyl-1,3,5-triazin-2-yl)aminocarbonyl]benzenesulfonamide, m.p. 198°–200° C.

DETAILED DESCRIPTION OF THE INVENTION

Synthesis

Compounds of Formula I can be prepared by one or more of the methods shown below in Equations 1, 2, 3 and 4. The method of choice for the individual compounds of Formula I will be obvious to one skilled in the art.

Equation 1 illustrates the reaction of sulfonylisocyanates and sulfonylisothiocyanates of Formula II with the appropriate heterocyclic amines of Formula III to give the desired sulfonylureas I.

Equation 1

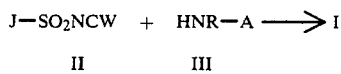

wherein

J, R, W and A are as previously defined provided $R_5$ is not H.

The reaction of Equation 1 is best carried out in an inert aprotic solvent such as methylene chloride, tetrahydrofuran or acetonitrile at a temperature between 0° and 82° C. A catalytic amount of 1,4-diazabicyclo[2.2.2]octane (DABCO) may be used to accelerate the reaction. In cases in which the products are insoluble in the reaction solvent, they may be isolated by simple filtration. When the products are soluble, they can be isolated by evaporation of the solvent and trituration of the residue with solvents such as 1-chlorobutane, diethyl ether or ethyl acetate, and filtration.

Many compounds of Formula I can be prepared as shown below in Equation 2 by the reaction of sulfonamides IV with the phenol ester of the appropriate carbamic acid or thiocarbamic acid of Formula V, in the presence of an equimolar quantity of a tertiary amine base such as 1,8-diazabicyclo[5.4.0]undec-7-ene (DBU).

Equation 2

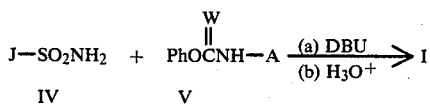

wherein

J, W and A are as previously defined, provided E is $CH_2$ or a single bond.

The reaction shown in Equation 2 is best carried out at $-5°$ to 25° C. in a solvent such as dioxane or acetonitrile for 1-2 hours under an inert atmosphere as described in European Publication No. 70,804 (published Jan. 26, 1983). The desired products of Formula I can be conveniently isolated by acidifying the reaction solution with aqueous hydrochloric acid and filtration. Alternatively, the aqueous layer can be extracted with a solvent such as methylene chloride or ethyl acetate. Drying and evaporation of the solvent affords the desired products. The phenyl carbamates V can be synthesized by treatment of the corresponding heterocyclic amines of Formula III with diphenyl carbonate or phenyl chloroformate in the presence of a base such as sodium hydride, pyridine, or potassium carbonate with a catalytic amount of 4-dimethylaminopyridine. The mixture is stirred at temperatures between 25° and 65° C. in a suitable solvent such as tetrahydrofuran for 12-36 hours.

Some compounds of Formula I may also be prepared by the reaction of a sulfonyl carbamate or thiocarbamate of Formula VI with an appropriate heterocyclic amine II, according to Equation 3.

Equation 3

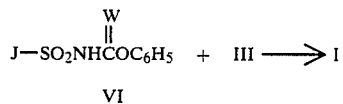

wherein

J, A, W and R are as previously defined, provided E is $CH_2$ or a single bond.

The reaction of Equation 3a is carried out at about 50° to 100° C. in an inert solvent such as 1,4-dioxane for 0.5 to 24 hours according to EPO Publication No. 44,807.

Phenylcarbamates and phenylthiocarbamates of Formula VI can be prepared by the methods described, or modifications thereof known to those skilled in the art, in U.S. Pat. No. 4,443,243.

In addition, some compounds of Formula I, wherein W is O, may be prepared by the reaction of an appropriate phenol of Formula VII with an appropriate sulfamoyl chloride of Formula VIII, as shown in Equation 4.

Equation 4

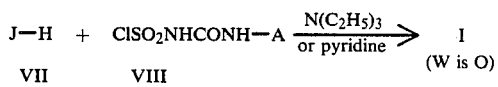

wherein

J and A are as previously defined provided E is O and $R_5$ is not H.

The reaction of Equation 4, and the preparation of sulfamoyl chlorides VIII, may be performed according to the procedure of B. Böhner, U.S. Pat. No. 4,391,976. Preferably sulfamoyl chloride VIII is prepared and reacted directly, without isolation, with phenol VII in the presence of a base such as pyridine or triethylamine at about 0°-25° C. in an inert solvent such as dioxane or acetonitrile. Sulfamoyl chlorides VIII are prepared by reaction of heterocyclic amines III with chlorosulfonylisocyanate at about 0°-10° C. in an inert solvent such as dioxane or acetonitrile.

Many sulfonyl isocyanates of Formula II can be prepared as shown in Equation 5 by the reaction of sulfonamides of the general structure IV with phosgene in the presence of n-butyl isocyanate and a catalytic amount of 1,4-diazabicyclo[2.2.2]octane (DABCO).

Equation 5

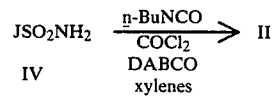

wherein

J is as previously defined, provided E is not O, and $R_5$ is not H.

The reaction depicted in Equation 5 is best carried out according to the procedure described in U.S. Pat. No. 4,238,621.

Alternatively, many sulfonyl isocyanates II can be prepared via phosgenation of the preformed n-butylureas of Formula IX as represented in Equation 6.

Equation 6

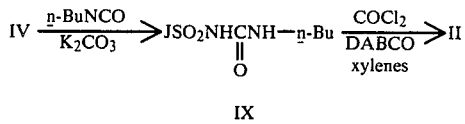

wherein

J is as defined in Equation 5.

The compounds of Formula IX are conveniently prepared by stirring a mixture of the appropriate sulfonamide IV, anhydrous potassium carbonate, and n-butyl isocyanate in a suitable solvent such as acetone or methyl ethyl ketone at 25° to 80° C. until all of the isocyanate has reacted. The products are isolated by quenching in dilute aqueous acid and recrystallizing the insoluble solid. The n-butylureas IX are then treated with phosgene and a catalytic amount of DABCO in refluxing xylenes or chlorobenzene in a manner analogous to that described in the reference cited for Equation 5.

Alternatively, treatment of many of the sulfonamides of Formula IV with thionyl chloride gives intermediate N-sulfinylsulfonamides X, which afford sulfonylisocyanates II upon exposure to phosgene in the presence of a catalytic amount of pyridine, as shown in Equation 7.

Equation 7

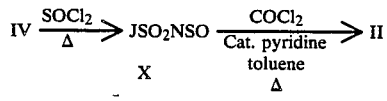

wherein

J is as originally defined, provided E is not O and $R_5$ is not H.

The reaction of Equation 7 can best be performed according to the procedure of H. Ulrich, B. Tucker and A. Sayigh, *J. Org. Chem.*, 34, 3200 (1969).

Sulfonyl isothiocyanates (II, W is S) are known in the art and are prepared from the corresponding sulfonamides (IV) by reaction with carbon disulfide and potassium hydroxide followed by treatment of the resulting dipotassium salt VI with phosgene. Such a procedure is described in *Arch. Pharm.* 299, 174 (1966).

Sulfamoyl isocyanates of Formula II (wherein E is O) are prepared by reaction of phenols VII with chlorosulfonylisocyanate at reflux in an inert solvent such as toluene, as illustrated in Equation 8.

Equation 8

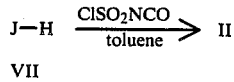

wherein

J is J-1, E is O and $R_5$ is not H.

The reaction of Equation 8 is best carried out according to procedures analogous to U.S. Pat. No. 4,475,944 and references cited therein.

The sulfonamides of Formula IV can be prepared by one or more of the methods illustrated hereinafter in Equations 9, 10, 16 or 18.

In addition, sulfonamides of Formula IV, wherein J is J-1 to J-5, Q is Q-20 and E is CH₂ or a single bond, may be prepared by reacting a corresponding sulfonamide, wherein Q is NH₂, with β-chloroethyl chloroformate followed by cyclization of the formed β-chloroethyl carbamate with base such as sodium methoxide. For details, refer to analogous reactions known in the art, for instance, *Bull. Chem. Soc. Japan*, 35, 1309 (1962). Similarly, reacting an appropriate sulfonamide (Q is NH₂) with 3-chloropropyl chloroformate may provide sulfonamides IV, wherein Q is Q-28. Also, sulfonamides IV, wherein J is J-1 to J-5, Q is Q-24 and E is CH₂ or a single bond, may be prepared by reaction of a corresponding sulfonamide, wherein Q is NHNH₂, with a propiolate ester by obvious methods.

Equation 9 depicts the reaction of sulfonyl chlorides of Formula XI with ammonia to give sulfonamides of Formula IVa.

Equation 9

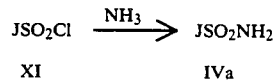

wherein

J is a previously defined, provided E is not O.

The amination of Equation 9 can be effected by adding at least two molar equivalents of either anhydrous ammonia or concentrated ammonium hydroxide to a solution of the sulfonyl chloride XI in a solvent such as diethyl ether, methylene chloride, or tetrahydrofuran at temperatures between −30° C. and 25° C. The sulfonamides of Formula IVa are isolated either by filtration, in which case the ammonium chloride by-product is removed by washing with water, or extraction into an organic solvent such as methylene chloride. Drying and evaporation of the solvent affords the sulfonamides IVa, which are usually sufficiently pure to be carried directly on to the next step.

Sulfonamides of Formula IVb can be prepared as depicted in Equation 10 by treatment of the corresponding N-t-butylsulfonamides XII with an appropriate acid such as trifluoroacetic (TFA), polyphosphoric (PPA), or p-toluenesulfonic acid (p-TSA).

Equation 10

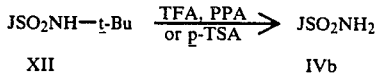

wherein

J is as originally defined, provided E is CH₂ or a single bond.

The reaction of Equation 10 is conveniently carried out by stirring a solution of the compound of Formula XII in excess trifluoroacetic acid (approximately 0.3M) at about 25° C. for 1–24 hours. The desired sulfonamides of Formula IVb are then isolated by removal of the volatiles in vacuo and recrystallization from a solvent such as ethyl acetate, diethyl ether, or 1-chlorobutane. Alternatively, the N-t-butylsulfonamides of Formula XII can be treated with a catalytic amount of p-toluene sulfonic acid monohydrate in a solvent such as toluene or xylenes at reflux temperature for 1–6 hours. The desired products are then isolated in a manner analogous to the one described above. For use of PPA in the deprotection of N-t-butylsulfonamides, see J. G. Lombardino, *J. Org. Chem.*, 36, 1843 (1971); for use of TFA, see J. D. Catt and W. L. Matier, *J. Org. Chem.*, 39, 566 (1974).

Sulfonyl chlorides of Formula XI can be prepared by one or more of the methods shown below in Equations 11-13.

Diazotization of appropriately substituted amine derivatives of Formula XIII, as shown in Equation 11, and subsequent coupling with sulfur dioxide in the presence of either cupric or cuprous chloride give the desired products of Formula XIa.

Equation 11

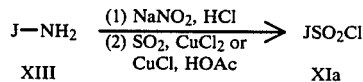

wherein

J is as originally defined, provided E is a single bond.

The reaction of Equation 11 can be effected by analogous methods described in EP-A Nos. 83,975 and 85,476 (published Aug. 10, 1983). In Equation 11, a substituted amine XIII, in acetic acid and hydrochloric acid is treated with a solution of sodium nitrite in water at $-5°$ to $5°$ C. After being stirred for 10-30 minutes at about $0°$ C., the solution is added to a mixture of excess sulfur dioxide and a catalytic amount of cupric or cuprous chloride in acetic acid at about $10°$ C. After stirring for 0.25 to 24 hours at temperatures between $10°$ to $25°$ C., the solution is poured into a large excess of ice water. The sulfonyl chlorides XIa can be isolated by filtration, or by extraction into a solvent such as methylene chloride or 1-chlorobutane, followed by drying and evaporation of the solvent.

Compounds of Formula XIb can be prepared via oxidative chlorination of the appropriate thioethers of Formula XIV as represented in Equation 12.

Equation 12

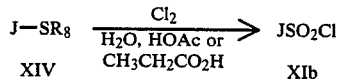

wherein

J is as originally defined, provided E is a single bond and $R_1$, $R_5$ or $R_7$ do not contain a thioether, alkenyl or alkynl group; and $R_8$ is $C_2$-$C_3$ alkyl or benzyl.

The reaction of Equation 12 can be carried out by contacting a suspension of the thioether XIV in a solvent such as acetic acid or propionic acid in the presence of at least 2.5 equivalents of water and at least 3.0 equivalents of chlorine at about $-10°$ to $30°$ C. for 0.25 to 5 hours. The reaction mixture is poured into icewater and the product is isolated by filtration or extraction with a solvent such as methylene chloride. The extraction product is optionally washed with aqueous sodium bicarbonate until neutral or slightly basic to litmus, then dried, and the solvent is evaporated to yield a product sufficiently pure to be carried directly on to the next step.

Alternatively, oxidative chlorination of thioethers XIV, wherein $R_8$ is benzyl or hydrogen, with a hypochlorite solution, i.e., NaOCl, may provide sulfonyl chlorides XIb. For details, see analogous reactions in L. H. McKendry and N. R. Pearson, South African Patent Application No. 84/8845. Mercaptans or thioethers may also be transformed to sulfonyl fluorides via reaction with chlorine and potassium hydrogen difluoride, which on further reaction with ammonia or ammonium hydroxide may provide sulfonamides (see e.g. D. J. Brown and J. A. Haskins, *J. Chem. Soc. Perkin Trans. I*, 522 (1972)).

Benzenemethanesulfonyl chlorides of Formula XIc may be prepared from appropriately substituted benzyl chlorides or bromides of Formula XV by a two-step procedure outlined in Equation 13.

Equation 13

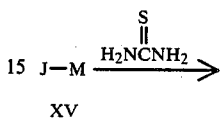

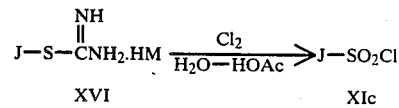

wherein

J is J-1, E is $CH_2$ and $R_1$, $R_5$ or $R_7$ do not contain a thioether, alkenyl or alkynyl group; and M is Cl or Br.

The conversion of alkyl halides of Formula XV to isothiouronium salts of Formula XVI can be carried out by the analogous procedure of T. B. Johnson and J. M. Sprague, *J. Am. Chem. Soc.*, 58, 1348 (1936); 59 1837 and 2439 (1937); 61 176 (1939). Oxidative chlorination of isothouronium salts such as XVI to afford sulfonyl chlorides of Formula XIc is best carried out according to the analogous procedure of Johnson as described in *J. Am. Chem. Soc.*, 61, 2548 (1939).

The benzyl halides of Formula XV above may be prepared by conventional methods by reaction of appropriately substituted toluenes with either N-bromosuccinimide or N-chlorosuccinimide in an inert solvent such as carbon tetrachloride at $25°$ to reflux temperature. A free radical catalyst such as azoisobutyronitrile or benzoyl peroxide is usually employed to initiate the reaction. When complete, the cooled solution is filtered to remove the by-product succinimide and the filtrate is concentrated in vacuo.

By analogy other arylmethanesulfonyl chlorides of Formula XIc (J is $J_2$-$J_5$) may be prepared from appropriate arylmethane compounds of Formula XV (J is $J_2$-$J_5$) by those skilled in the art.

The requisite aniline derivatives of Formula XIII can be prepared by reduction of the corresponding nitro compounds of Formula XVII as depicted in Equation 14.

Equation 14

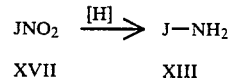

wherein

J is as originally defined, provided E is a single bond.

The reduction reaction of Equation 14 can be accomplished by methods known in the literature by those skilled in the art. For details see, for example, U.S. Pat. No. 3,846,440 and referenced cited therein, and U.S. Pat. No. 3,846,439.

Phenols of the general Formula VII may be prepared via hydrolysis of diazonium salts prepared from amines XIII in sulfuric acid or hydrochloric acid, as depicted in Equation 15 below. For details refer to analogous procedures reported in the literature, for example, A. I. Vogel, "Practical Organic Chemistry", p. 595 (1956), 3rd Edition; U.S. Pat. No. 3,270,029; J. K. Finley et al., *J. Het. Chem.*, 6, 841 (1969); M. Ohta et al., *J. Pharm. Soc. Japan*, 73, 701 (1953); and Neth. Appl. No. 6,602,601.

Equation 15

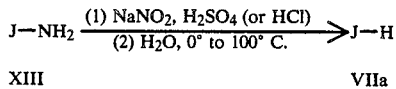

wherein

J is as originally defined, provided E in XIII is a single bond.

A choice by one skilled in the art of the appropriate method for preparing compounds of Formula I, as well as intermediate reagents such as sulfonamides, sulfonyl chlorides, amines and phenols, must take into account the nature of the substituents contained within the J values ($J_1$-$J_5$), namely Q and $R_1$, and their chemical compatibility with reaction conditions of Equations 1-15.

As illustrated in Equation 16, 1,3,4-oxadiazolin-5-ones of Formula XIX are prepared by reaction of hydrazides XVIII with trichloromethyl chloroformate to form XIX ($R_5$=H). Subsequent N-alkylation then provides XIX.

Equation 16

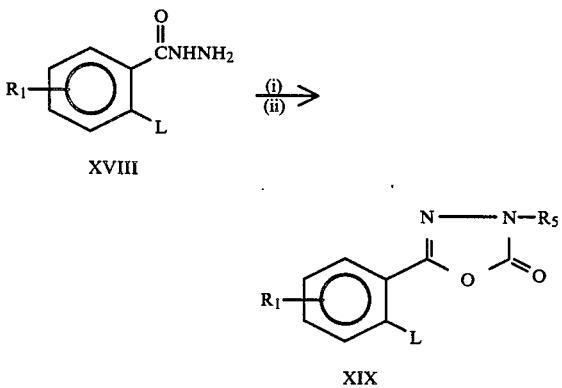

(i) ClCO₂CCl₃;
(ii) R₅M, base; or R₉SO₂OR₅, base, wherein

L is $CH_3$, $SR_8$, $NO_2$, OH, $SO_2NH_2$ or $CH_2SO_2NH_2$;
M is Cl, Br, or I;
$R_1$, $R_5$ and $R_8$ are as originally defined; and
$R_9$ is $CH_3$ or p-tolyl.

The reaction of XVIII, wherein L is other than $SO_2NH_2$ or $CH_2SO_2NH_2$, with trichloromethyl chloroformate is best carried out in refluxing dioxane, according to a procedure of N. Chau et al., *J. Het. Chem.*, 19, 541 (1982). The preparation of XIX, wherein L is $SO_2NH_2$ or $CH_2SO_2NH_2$ ($R_5$=H), is preferably carried out by reacting the corresponding XVIII with at least one equivalent of trichloromethyl chloroformate or phosgene followed by two equivalents of a suitable base, such as triethylamine, in an inert solvent, such as dioxane, at about 10° to 100° C. Alternatively, XVIII may be cyclized to XIX ($R_5$=H) by reaction with 1,1-carbonyldiimidazole, according to a procedure of E. Tihanyi et al., *Heterocycles*, 20, 571 (1983); or, where L is $CH_3$, $NO_2$ or OH, by reaction with excess phosgene in a solvent such as refluxing chloroform or dioxane; for details, see for example, U.S. Pat. No. 3,127,410; *Chem. Ber.*, 98, 540 (1965); *J. Am. Pharm. Assoc.*, 47, 799 (1958); and *J. Het. Chem.*, 1, 186 (1964).

The N-alkylation reaction of Equation 16 is best carried out by reacting XIX ($R_5$=H) with a suitable base followed by an alkylating agent in a solvent such as methanol, tetrahydrofuran or dimethylformamide (DMF) at a temperature between about 0° and 100° C. Suitable bases include sodium hydride, sodium methoxide, potassium carbonate, or preferably, potassium t-butoxide in DMF. The products are isolated by dilution with water and filtration, or extraction with methylene chloride. For analogous reactions see, for example, *Heterocycles*, 20, 571 (1983) and *Canadian J. Chem.*, 43, 1607 (1965).

As shown in Equation 17, nitrocompounds of Formula XVIIa may be prepared by reaction of nitro-compounds of Formula XXI with the sodium or potassium salts of oxadiazolin-5-ones of thiadiazolin-5-ones of Formula XX.

Equation 17

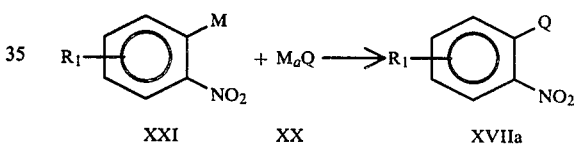

wherein $M_a$ is Na⁺ or K⁺;
$R_1$ and M are as previously defined; and
Q is Q-15, Q-16 or Q-17.

The reaction of Equation 17 is best carried out using the analogous N-alkylation procedures described above in Equation 16. For more details, refer to analogous reactions described in *J. Het. Chem.*, 15, 1221 (1978); *Ibid.*, 19, 823 (1982); U.S. Pat. No. 3,846,439; and *Heterocycles*, 13, 197 (1979). Compounds XX (Q is Q-15, $M_a$ is H) can be prepared by known methods, such as reaction of hydrazides with phosgene or trichloromethyl chloroformate; see, for examples, *Chem. Ber.*, 98, 540 (1965), and *J. Het. Chem.*, 19, 541 (1982); or by reaction of trimethyl acetylurea with potassium hypobromite to form XX, wherein Q is Q-15, $R_7$ is t-butyl and $M_a$ is H; see U.S. Pat. No. 3,846,439. Compounds XX, wherein Q is Q-16 or Q-17 and $M_a$ is H, are known; see respectively, U.S. Pat. No. 4,448,968 and U.S. Pat. No. 3,767,646.

As shown in Equation 18 below, sulfonamides of Formula IV may be prepared by a sequence of reactions in which hydrazide XXII is reacted with an alkylisocyanate to form a semicarbazide, which is cyclized to form a 1,3,4-triazolin-5-one of Formula IVc ($R_5$=H), which is N-alkylated to provide IVc.

Equation 18

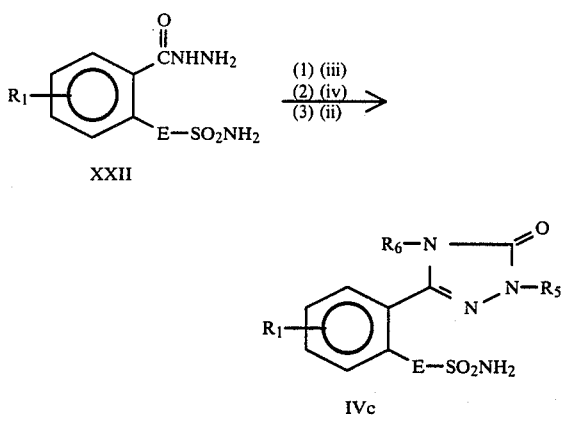

(iii) is $R_6NCO$;
(iv) is NaOH, $NaOCH_3$ or "DBU".

wherein $R_1$, $R_5$, $R_6$ and (ii) are as previously defined; and
E is $CH_2$ or a single bond.

The cyclization reaction of Equation 18 is best carried out according to analogous procedures described in Chem. Pharm. Bull., 24, 1336 (1976) and Ibid., 21, 1342 (1973). Thus, reaction of hydrazide XXII with an appropriate alkyl isocyanate, in a solvent such as dioxane, by general procedures, provides the corresponding semicarbazide. Subsequent reaction of the semicarbazide with a base, such as aqueous sodium hydroxide in a solvent such as ethanol, or with "DBU" in a solvent such as dioxane, or sodium methoxide in a solvent such as methanol, at about 0° to 80° C. can provide IVc ($R_5$=H). Subsequent N-alkylation by methods described in Equation 16 provides IVc.

In a similar fashion to reactions described in Equations 16 and 18, sulfonamido-thiophenes, -pyrazoles and -pyridines of Formula IV, wherein J is J-2 to J-5, E is a single bond or $CH_2$ and Q is Q-1 or Q-7, may be prepared from appropriate corresponding hydrazido sulfonamides, by those skilled in the art.

Also, t-butylsulfonamido-thiophenes, -pyrazoles and -pyridines of Formula XII, wherein J is J-2 to J-5, E is a single bond and Q is Q-15 and Q-16, may be prepared by reaction of appropriate corresponding t-butylsulfonamides, which contain a o-halogen atom susceptible to nucleophilic displacement reactions, with the sodium or potassium salts of XX, by those skilled in the art. Similarly, nitro-thiophenes, -pyrazoles and -pyridines of Formula XVII, wherein J is J-2 to J-5, E is a single bond and Q is Q-15, Q-16 or Q-17 may be prepared from corresponding nitro compounds containing an appropriate o-halogen atom by those skilled in the art. Preferably, these reactions are run in the presence of a catalyst such as copper (II) oxide.

In addition, as illustrated in Equation 19 below, thioethers of Formula XIVa may be prepared from appropriately substituted thioethers of Formula XXIII.

Equation 19

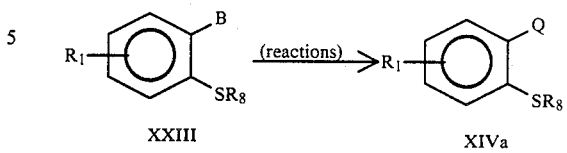

wherein $R_1$ and $R_8$ are as defined in Equation 16;
B represents appropriate functional groups, described hereinafter, which may be reacted to prepare o-groups Q-2 to Q-14 or Q-18 to Q-30; and
Q is Q-2 to Q-14 or Q-18 to Q-30.

The reaction of Equation 19 may be run according to analogous methods known in the art, or simple modifications thereof.

For instance, thioethers XIVa, wherein Q is Q-2 ($R_6$=H) may be prepared by reaction of XXIII, wherein B is an amidoxime group, with diketene followed by cyclization of the formed o-acetoacetylamidoxime with base such as sodium methoxide in refluxing toluene, according to Chem. Pharm. Bull., 30, 336 (1982); or by reaction of the amidoxime with ethyl chloroformate and a base such as pyridine in refluxing toluene or benzene for a short time, according to U.S. Pat. No. 3,767,646. Subsequent N-alkylation of XIVa (Q-2; $R_6$ is H) provides XIVa (Q is Q-2); see for example, U.S. Pat. No. 3,767,646; Ann. Chim. (Rome), 53, 1405 (1963); Tetrahedron, 21, 1681 (1965); Chem. Ber., 117, 2999 (1984); Chem. Ber., 103, 2330 (1970); and Equation 16. Alternatively, XIVa (Q is Q-2) may be prepared by reaction of XXIII, wherein B is a N-alkyl amidoxime, with ethyl chloroformate, according to Chim. Acta. Turc., 4, 131 (1976).

Thioethers XIVa, wherein Q is Q-3, may be prepared by reaction of XXIII, wherein B is a nitrile group, with an N-alkyl-hydroxylamine followed by cyclization of the formed N-alkyl-N-hydroxy amidine with ethyl chloroformate and base such as pyridine, according to J. Chem. Soc. Perkins Trans, I, 85 (1974); by reaction of XXIII, wherein B is a carbonylisocyanate group, with a N-alkyl-hydroxylamine, according to J. Chem. Soc., (C), 2794 (1969); or by reaction of a N-ethoxycarbonylthioamide with N-alkylhydroxylamine, according to J. Org. Chem., 41, 3233 (1976).

Thioethers XIVa, wherein Q is Q-4 ($R_6$ is H), may be prepared by reacting XXIII, wherein B is an acid chloride group, with potassium thiocyanate to form a carbonylthiocyanate, which with methanol gives the corresponding carbamate, which with methyl iodide gives an aminothiolcarbamate, which with hydroxylamine cyclizes to a 3-methoxy-1,2,4-oxadiazol ring, which with an appropriate demethylating agent such as pyridine.HCl is converted to XIVa (Q-4, $R_6$ is H), which may be N-alkylated with diazomethane, or other appropriate alkylating agent, to form XIVa (Q is Q-4), according to Tetrahedron, 21, 1681 (1965). Alternatively, XXIII, wherein B is 3-methoxy-1,2,4-oxadiazol ring, may be heated with sodium iodide and acetonylacetone to form XIVa (Q is Q-4, $R_6$ is $CH_3$), according to the above reference.

Thioethers XIVa, wherein Q is Q-5 ($R_6$ is H), may be prepared by reaction of XXIII, wherein B is a thiohydrazide group, with phosgene, according to Nippon Kagaku Kaishi, 315 (1976); by reacting XXIII, wherein B is a N-carbamoylthiohydrazide, with heat in the presence or absence of additives such as concentrated hydrochloric acid to cause cyclization to XIVa (Q-5, $R_6$ is H); or by demethylation of XXIII, wherein B is a 2-methoxy-1,3,4-thiazole ring with hydrogen chloride in a solvent such as dioxane, according to U.S. Pat. No. 4,448,968. Subsequent N-alkylation by general methods provides XIVa (Q is Q-5); see, for example, *Helv. Chim. Acta*, 65, 2606 (1982) and Equation 16. Thioethers XXIII, wherein B is a 2-methoxy-1,3,4-thiazole ring, may be prepared from XXIII, wherein B is an imidate, ortho-ester or acid chloride, according to U.S. Pat. No. 4,448,968.

Thioethers XIVa, wherein Q is Q-6, may be prepared by rearrangement of 3,4-disubstituted-1,2,4-oxadiazoline-5-thiones, according to *Tetrahedron*, 22, 1945 (1977), and *J. Chem. Soc. Perkin Trans*, I, 687 (1983). The 5-thiones may be prepared by reaction of XXIII, wherein B is a N-alkylamidoxime, with thiophosgene, according to *Chem. Ber.*, 28, 2227 (1895).

Thioethers XIVa, wherein Q is Q-7 or Q-8, may be prepared according to the procedures of *Chem. Pharm. Bull.*, 21, 1342 (1973) and *Chem. Pharm. Bull.*, 24 1336 (1976). Accordingly, XXIII, wherein B is an alkylsemicarbazide group is reacted with a base such as sodium hydroxide, followed by N-alkylation by general methods to form XIVa (Q-7). Reaction of XXIII, wherein B is a 1,2-dimethylsemicarbazide group, with alkaline solutions provides XIVa (Q-8).

Thioethers XIVa, wherein Q is Q-9, are prepared by reaction of XXIII, wherein B is an amide group, with chlorocarbonylsulfenyl chloride in a solvent such as refluxing tetrahydrofuran, according to *Phosphorous and Sulfur*, 15, 137 (1983), *J. Org. Chem.*, 43, 3736 (1978) and *Acta. Chem. Scan.*, 21, 1871 (1967).

Thioethers XIVa, wherein Q is Q-10, may be prepared by reaction of XXIII, wherein B is a hydroxyoxime group, with phosgene; see, for example, *Chem. Ber.*, 84, 688 (1951); *Tetrahedron Lett.*, 319, (1968); Ger. Offen. No. 2,059,990 (1972); and *Rocz. Chem.*, 45, 833 (1971).

Thioethers XIVa, wherein Q is Q-11, may be prepared by reaction of XXIII, wherein B is a thiazolin-4,5-dione group, with sulfur, according to *Chem. Ber.*, 100, 1627 (1967).

Thioethers XIVa, wherein Q is Q-12, may be prepared by reaction of XXIII, wherein B is a thiohydroxamic acid group, with phosgene under alkaline conditions according to conditions obvious to one skilled in the art and found in Belg. No. 632,072 and Ger. Offen. No. 2,059,990.

Thioethers XIVa, wherein Q is Q-13, may be prepared by reaction of XXIII, wherein B is a thioamide group, with oxalyl chloride, according to *Chem. Ber.*, 93, 671 (1960) and *Chem. Ber.*, 114, 549 (1981).

Thioethers XIVa, wherein Q is Q-14, may be prepared by reaction of XXIII, wherein B is a N-alkylamidine group, with oxalyl chloride, according to *Chem. Ber.*, 100, 2064 (1967) and *Chemistry of Penicillin*, 52 (1949).

Thioethers XIVa, wherein Q is Q-18 or Q-19, may be prepared by reaction of XXIII, wherein B is a α-oxopropanoate ester group, with an alkylhydrazine or hydroxylamine.HCl, respectively, according to methods known in the art; see for example, *Tetrahedron*, 20, 299 (1964) and U.S. Pat. No. 4,044,013 for Q-18; and *J. Gen. Chem.* (U.S.S.R.), 17, 1816 (1947) (*Chem. Abst.* 42: 4170c) for Q-19. One skilled in the art will recognize that in compounds containing the substituents Q-18 or Q-19, these heterocycles may partially exist in their respective tautomeric forms.

Thioethers XIVa, wherein Q is Q-21 or Q-22, may be prepared by heating XXIII, wherein B is a NHCOCH$_2$CH$_2$OH or NHCOCH$_2$OH group, respectively, with paraformaldehyde and an acid catalyst in a solvent such as toluene, according to analogous methods described in *Heterocycles*, 7, 919 (1977) and *Japan Kokai Tokyo Koho* 79, 24,869 (*Chem. Abst.* 91: 74630f).

Thioethers XIVa, wherein Q is Q-23, may be prepared by reaction of XXIII, wherein B is a hydroxylamine group, with an appropriate 3-halopropanoic acid chloride, followed by cyclization of the formed 3-halopropanamide with base. For details refer to analogous methods known in the art, for instance, U.S. Pat. No. 4,405,357.

Thioethers XIVa, wherein Q is Q-24, may be prepared by reaction of XXIII, wherein Q is a hydrazine group, with a propiolate ester or an appropriate derivative.

Thioethers XIVa, wherein Q is Q-25, may be prepared by reaction of XXIII, wherein Q is an amidine group, with chloroacetyl chloride followed by cyclization. Also, reaction of XXIII (B is an amidine group), with an appropriate α-oxopropanoate ester may provide XIVa (Q is Q-27).

Thioethers XIVa, wherein Q is Q-20 or Q-28, may be prepared by reaction of XXIII wherein B is an amino group, with 2-chloroethyl or 3-chloropropyl chloroformate followed by cyclization with an appropriate base.

Also, reaction of thioethers XXIII, wherein B is an isocyanate group, with an appropriate 3-chloropropyl or 2-chloroethylamine followed by cyclization of the formed urea may provide thioethers XIVa, wherein Q is 29 or 30.

In similar fashion, by substituting appropriate nitrobenzenes for thioethers XXIII in Equation 19 above, and carrying out the reactions described therein, those skilled in the art may prepare nitrobenzenes of Formula XVII, wherein J is J-1, E is a single bond and Q is as defined in Equation 19.

Also, by substituting appropriate phenols for thioethers XXIII in Equation 19, and carrying out the reactions described therein, or simple modifications thereof, those skilled in the art may prepare phenols of Formula VII, wherein J is J-1, E is O and Q is as defined in Equation 19. In some cases a phenolic protecting group which could be later removed would be desirable. For a review on phenolic protecting groups see, T. W. Greene, *Protective Groups in Organic Synthesis*, pp. 87–113, John Wiley and Sons, Inc., New York, 1981.

Also, by analogy, by substituting appropriate thiophenes, pyrazoles or pyridines for thioethers XVIII and XXIII in Equations 16 and 19 above, respectively, and carrying out the reactions described therein or simple modifications thereof, those skilled in the art may prepare thioethers of Formula XIV, wherein J is J-2 to J-5, E is a single bond and Q is as defined in Equations 16 and 19.

The heterocyclic amines of Formula III in Equation 3 above can be prepared by methods known in the literature, or simple modifications thereof, by those skilled in the art. For instance, EP-A No. 84,224 (published July 27, 1983) and W. Braker et al., *J. Chem. Soc.*, 69, 3072 (1947) describes methods for preparing aminopyridines and triazines substituted by acetal groups such as dialkoxymethyl or 1,3-dioxolan-2-yl, among other groups. Also, for example, South Africa Patent Application Nos. 82/5045 and 82/5671 describe methods for preparing aminopyrimidines and triazines substituted by haloalkyl or haloalkylthio groups such as $OCH_2CH_2F$, $OCH_2CF_3$, $SCF_2H$, and $OCF_2H$. South African patent application No. 83/7434 (published October 5, 1983) describes methods for the synthesis of cyclopropylpyrimidines and triazines substituted by such groups as alkyl, haloalkyl, alkoxy, haloalkoxy, alkylamino, dialkylamino or alkoxyalkyl.

The 5,6-dihydrofuro[2.3-d]pyrimidine-2-amines, the cylcopenta[d]pyrimidines-2-amines (III, A is A-2) and the 6,7-dihydro-5H-pyrano[2.3-d]pyrimidin-2-amines (III, A is A-3) can be prepared as described in EP-A-15,683. The furo[2.3-d]pyrimidin-2-amines (III, A is A-4) are described in EP-A-46,677. Compounds of Formula III, where A is A-7, are described in EP-A-125,864.

Compounds of Formula III, where A is A-5, are described in EP-A-73,562. Compounds of Formula III, where A is A-6, are described in EP-A-94,260.

In addition, general methods for preparing aminopyrimidines and triazines have been reviewed in the following publications:

"The Chemistry of Heterocyclic Compounds," a series published by Interscience Publ., New York and London;

"Pyrimidines", Vol. 16 of the same series by D. J. Brown;

"s-Triazines and Derivatives," Vol. 13 of the same series by E. M. Smolin and L. Rapaport;

F. C. Schaefer, U.S. Pat. No. 3,154,547 and K. R. Huffman and F. C. Schaefer, *J. Org. Chem.*, 28, 1812 (1963), which describes the synthesis of triazines.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, or carbonate). Quaternary amine salts can be made of similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Unless otherwise indicated, temperatures are in degrees centigrade.

EXAMPLE 1

5-{2-[(Phenylmethyl)thio]phenyl}-1,3,4-oxadiazol-2(3H)-one

To a solution containing 12.2 g of trichloromethyl chloroformate in 130 ml of p-dioxane was added portionwise 16 g of 2-[(phenylmethyl)thio]benzoic acid, hydrazide [prepared by the procedure of South African Patent Application No. 838,416 (1983)] to cause a slight exotherm to 37° C. After stirring at ambient temperature for 0.5 hr., the suspension was refluxed for 6 hours, then cooled to 25° C. and poured onto excess ice/water to yield a precipitate. The mixture was filtered, washed with water and the isolated solid was recrystallized from acetonitrile to yield 14 g of the subject compound: m.p. 169°–172° C.

IR (Nujol): 1790 cm$^{-1}$ (C=O).

EXAMPLE 2

3-Methyl-5-[2-[(phenylmethyl)thio]phenyl]-1,3,4-oxadiazol-2(3H)-one

To a suspension of 2.9 g of potassium t-butoxide in 60 ml of DMF under a $N_2$ atmosphere was added portionwise 7 g of the product of Example 1 while maintaining the reaction temperature at 25°–30° C. with an ice-water bath. After stirring at 25° C. for 1 hour, 7 g of methyl iodide was added dropwise to cause an exotherm to 37° C. The suspension was heated at 40°–60° C. for 5 hours, then cooled to 25° and poured onto excess ice-water to yield a precipitate. The suspension was filtered, and the isolated solid was dissolved in tetrahydrofuran and dried over $MgSO_4$. The isolated solid was passed through a silica gel column with methylene chloride and, after evaporation of the first eluant, 5 g of the subject compound was obtained; m.p. 137°–140° C.

IR (Nujol): 1780 cm$^{-1}$ (C=O)

NMR (CDCl$_3$): ppm 3.4 (s, 3H, NCH$_3$); 4.1 (s, 2H, CH$_2$); 7.2–7.9 (m, 9H, Ar).

EXAMPLE 3

2-(4,5-Dihydro-4-methyl-5-oxo-1,3,4-oxadiazol-2-yl)benzenesulfonyl chloride

To a suspension of 4 g of the product of Example 2 and 0.72 g of H$_2$O in 50 ml of propionic acid was added dropwise 3.4 ml of condensed Cl$_2$ while maintaining the reaction temperature at −5° to 0° C. with external cooling. The suspension was stirred at 0° for 0.75 hr., then poured onto excess ice-water to yield a precipitate. After filtration the isolated residue was washed with excess H$_2$O and then about 30 ml of hexane to yield 3.3 g of the subject compound as a crude solid; m.p. 122°–125° C.

IR (Njuol): 1755 cm$^{-1}$ (C=O)

EXAMPLE 4

2-(4,5-Dihydro-4-methyl-5-oxo-1,3,4-oxadiazol-2-yl)benzenesulfonamide

To a suspension of 3.3 g of the product of Example 3 in 50 ml of tetrahydrofuran was added dropwise 3 ml of condensed ammonia while keeping the reaction temperature at −5° C. with external cooling. After stirring at 0° for 1.5 hours, the solvent was evaporated in vacuo and water was added to the residue to yield a precipitate. After filtration the isolated residue was washed with water, then dissolved in tetrahydrofuran and dried over MgSO$_4$. After evaporation of the solvent in vacuo, 2.9 g of the subject compound was obtained as a crude solid; m.p. 168°-173° C.

IR (Nujol): 1770 cm$^{-1}$ (C=O); 3225 and 3310 cm$^{-1}$ (SO$_2$NH$_2$).

NMR (CDCl$_3$+DMSO): ppm 3.5 (s, 3H, NCH$_3$); 7.1 (s, 2H, SO$_2$NH$_2$); 7.7-8.4 (m, 4H, Ar).

EXAMPLE 5

2-(4,5-Dihydro-4-methyl-5-oxo-1,3,4-oxadiazol-2-yl)-N-[(4,6-dimethoxypyrimidin-2-yl)aminocarbonyl]benzenesulfonamide To a suspension of 0.4 g of the product of Eample 4 and 0.43 g of phenyl(4,6-dimethoxypyrimidin-2-yl)carbamate in 10 ml of p-dioxane was added 0.24 g of 1,8-diazabicyclo[5.4.0]undec-7-ene (DBU). The suspension was stirred for 2 hours at room temperature, then diluted with 50 ml of ice-water, and the obtained solution was acidified with ~10 drops of concentrated hydrochloric acid to yield a precipitate. After filtration the residue was washed with excess water, then suction-dried overnight to yield 0.6 g of a white solid. The solid was further purified by slurry-washing with 10 ml of warm ethyl acetate to yield 0.4 g of the subject compound; m.p. 208°-214° C.

IR (Nujol): 1710; 1770 cm$^{-1}$ (2×C=O)

NMR (CDCl$_3$): ppm 3.4 (s, 3H, NCH$_3$); 4.0 (s, 6H, 2×OCH$_3$); 5.8 (s, 1H, py-H); 7.7-7.9 (m, 3H, Ar); 8.5 (bs, 1H, Ar).

EXAMPLE 6

2-(4,5-Dihydro-4-methyl-5-oxo-1,3,4-oxadiazol-2-yl-N[(4-methyl-6-methoxy-1,3,5-triazin-2-yl)aminocarbonyl]benzenesulfonamide By the procedure of Example 5, 0.4 g of the product of Example 4 was reacted with 0.41 g of phenyl(4-methyl-6-methoxy-1,3,5-triazin-2-yl)carbamate and 0.24 g of "DBU" in 10 ml of p-dioxane. The isolated crude solid was purified by slurry-washing with 10 ml of warm acetonitrile to yield 0.3 g of the subject compound; m.p. 198°-200° C.

IR (Nujol): 1700 and 1770 cm$^{-1}$ (2×C=O)

NMR (CDCl$_3$): ppm 2.7 (s, 3H, CH$_3$); 3.5 (s, 3H, NCH$_3$); 4.1 (s, 3H, OCH$_3$); 7.8 (bm, 3H, Ar); 8.5 (bm, 1H, Ar).

EXAMPLE 7

N-[(Butylamino)carbonyl]-2-(4,5-dihydro-4-methyl-5-oxo-1,3,4-oxadiazol-2-yl)benzenesulfonamide A suspension of 15 g of the product prepared as in Example 4, 8.2 g of potassium carbonate and 7 g of n-butyl isocyanate in 150 ml of methyl ethyl ketone was refluxed for 6 hours. After concentrating the suspension in vacuo, ice-water (~300 ml) was added to the residue and the cloudy solution was filtered. The filtrate was acidified with concentrated hydrochloric acid to form a viscous oil. After decanting the water, the residual oil was dissolved in tetrahydrofuran, dried over MgSO$_4$, and the solvent was evaporated in vacuo to yield an oil which slowly solidified to yield 18.5 g of the subject compound as a crude solid; m.p. 110°-115° C.

EXAMPLE 8

2-(4,5-Dihydro-4-methyl-5-oxo-1,3,4-oxadiazol-2-yl)benzenesulfonyl isocyanate

A suspension of 8 g of the product of Example 7 and 0.4 g of DABCO in 90 ml of xylenes was heated under N$_2$ at 130°-135° C. while 1.8 ml of phosgene was added portionwise at a rate to maintain a reflux temperature of about 130°-135° C. The mixture was refluxed an additional two hours, cooled under N$_2$ to room temperature, filtered, and the filtrate was concentrated in vacuo to yield 6.9 g of the subject compound as a crude oil.

IR (neat): 1785 (b) cm$^{-1}$ (C=O); 2240 cm$^{-1}$ (NCO).

EXAMPLE 9

2-(4,5-Dihydro-4-methyl-5-oxo-1,3,4-oxadiazol-2-yl)-N-[(4-methoxypyrimidin-2-yl)aminocarbonyl]benzenesulfonamide To a solution of 0.18 g of 2-amino-4-methoxypyrimidine in 5 ml of methylene chloride was added a solution of 0.56 g of the product of Example 8 dissolved in 5 ml of methylene chloride. The suspension was stirred at 25° C. for 3 hours, then diluted with 20 ml of 1-chlorobutane and stirred 0.5 hr. After filtration the residue was washed with ether to yield 0.55 g of the subject compound; m.p. 223°-224° C.

IR (Nujol): 1700 and 1780 cm$^{-1}$ (2×C=O)

NMR (CDCl$_3$): ppm 3.5 (s, 3H, NCH$_3$); 3.9 (s, 3H, OCH$_3$); 6.45 (d, 1H, py H); 8.45 (d, 1H, py H); 7.7 (m, 3H, Ar); 8.5 (m, 1H, Ar).

EXAMPLE 10

5-(2-Hydroxyphenyl)-1,3,4-oxadiazol-2(3H)-one

To a solution of 10 g of salicylhydrazide in 100 ml of p-dioxane was added dropwise 13.1 g of trichloromethyl chloroformate while maintaining the temperature at 20°-30° C. with external cooling. After stirring at 25° C. for 0.5 hours, the suspension was refluxed for 4 hours then cooled to 25° C. and poured into excess ice-water. The mixture was filtered and the residue was recrystallized from acetonitrile to yield 9.0 g of the subject compound; m.p. 198°-200° C.

EXAMPLE 11

5-(2-Hydroxyphenyl)-3-methyl-1,3,4-oxadiazol-2(3H)-one

To a suspension of 3.8 g of potassium t-butoxide in 60 ml of dry DMF under a N$_2$ atmosphere was added portionwise 6 g of the product of Example 10 while maintaining the reaction temperature at 10°-20° C. with external cooling. After stirring at 25° C. for one hour, 9.6 g of methyl iodide was added dropwise at 10°-20° C. with external cooling. After stirring at room temperature for 16 hours, the suspension was poured into excess ice-water and filtered. The residue was recrystallized from 2-propanol to yield 4.6 g of the subject compound; m.p. 160°-162° C.

NMR (CDCl$_3$) ppm: 3.5 (s, 3H, NCH$_3$); 6.9-7.7 (m, 4H, Ar); 8.6 (bs, 1H, OH).

EXAMPLE 12

[2-(4,5-Dihydro-4-methyl-5-oxo-1,3,4-oxadiazol-2-yl-phenoxy]sulfonyl isocyanate

To a suspension of 4 g of the product of Example 11 in 75 ml of dry toluene under a N$_2$ atmosphere was added dropwise 3 g of chlorosulfonyl isocyanate at 25°-30° C. After stirring at 25° C. for 0.5 hour the suspension was refluxed for one hour, then cooled under N$_2$ to 25°. The solvent was evaporated from the solution in vacuo to yield 6 g of the subject compound as a crude oil.

IR (Nujol) cm$^{-1}$ 1770 (C=O); 2245 (NCO).

EXAMPLE 13

2-(4,5-Dihydro-4-methyl-5-oxo-1,3,4-oxadiazol-2-yl)phenyl[(4-chloro-6-methoxypyrimidin-2-yl)aminocarbonyl]sulfamate To a suspension of 0.48 g of 2-amino-4-chloro-6-methoxypyrimidine in 5 ml of dry methylene chloride was added a solution of 1.5 g of the crude product of Example 12 in 10 ml of methylene chloride. After stirring at 25° C. for 16 hours the solvent was evaporated in vacuo. After stirring the residue in about 20 ml of 1-chlorobutane for one hour, the suspension was filtered, and the isolated solid was triturated with about 30 ml of warm ethyl acetate to yield 0.5 g of the subject compound; m.p. 175°–178° C. IR (Nujol): 1725; 1780 cm$^{-1}$ (2×C=O) NMR (DCCl$_3$=DMSO): ppm 3.4 (s, 3H, OCH$_3$); 3.7 (s, 3H, NCH$_3$); 6.5 (s, 1H, py H); 7.5–7.9 (m, 5H, Ar+NH).

Using the techniques described in Equations 1–19 and Examples 5, 6, 9 and 13, or simple modifications thereof, the following compounds in Tables 1–7 may be made by one skilled in the art.

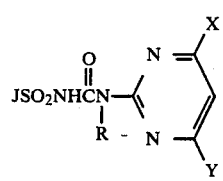

General Formula 1

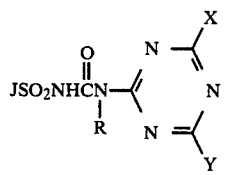

General Formula 2

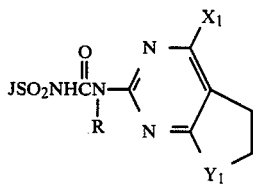

General Formula 3

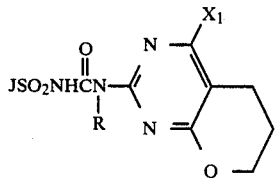

General Formula 4

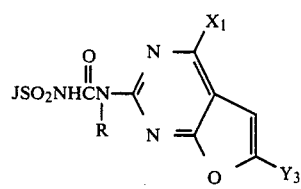

General Formula 5

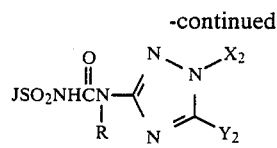

General Formula 6

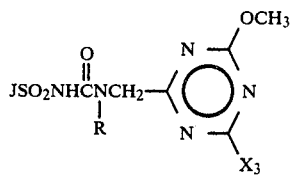

General Formula 7

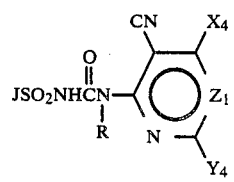

General Formula 8

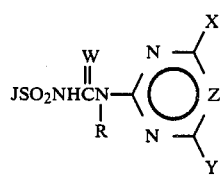

General Formula 9 wherein, for Tables 1 to 9, J-1, J-4 and J-5 represent structures previously described, while J-2a to J-2c and J-3a to J-3d represent the following general structures:

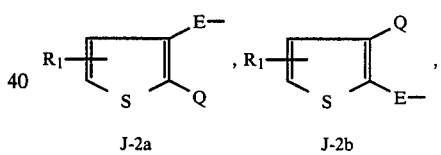

J-2a    J-2b

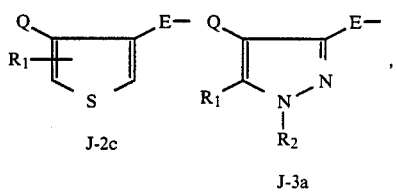

J-2c    J-3a

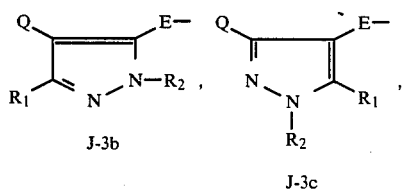

J-3b    J-3c

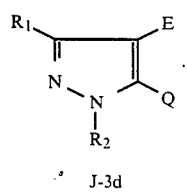

J-3d

TABLE 1

General Formula 1

| J | Q | E | R | R$_1$ | X | Y | m.p. °C. |
|---|---|---|---|---|---|---|---|
| 1 | Q-1(R$_5$ = CH$_3$) | — | H | H | CH$_3$ | OCH$_3$ | 221–222 |
| 1 | Q-1(R$_5$ = CH$_3$) | — | H | H | CH$_3$ | CH$_3$ | dec. 225 |
| 1 | Q-1(R$_5$ = CH$_3$) | — | H | H | OCH$_3$ | OCH$_3$ | 208–214 |
| 1 | Q-1(R$_5$ = CH$_3$) | — | H | H | Cl | OCH$_3$ | 239–242 |
| 1 | Q-1(R$_5$ = CH$_3$) | — | H | H | Br | OCH$_3$ | 236–240 |
| 1 | Q-1(R$_5$ = CH$_3$) | — | H | H | CH$_3$ | H | dec. 219 |
| 1 | Q-1(R$_5$ = CH$_3$) | — | H | H | OCH$_3$ | H | 223–224 |
| 1 | Q-1(R$_5$ = CH$_3$) | — | H | H | OCH$_3$ | CH$_2$OC$_2$H$_5$ | 171–172 |
| 1 | Q-1(R$_5$ = CH$_3$) | — | H | H | OCF$_2$H | OCH$_3$ | 174–176 |
| 1 | Q-1(R$_5$ = CH$_3$) | — | H | H | OCH$_3$ | CH(OCH$_3$)$_2$ | 142–148 |
| 1 | Q-1(R$_5$ = CH$_3$) | — | H | H | CH$_3$ | OC$_2$H$_5$ | 211–213 |
| 1 | Q-1(R$_5$ = CH$_3$) | — | H | H | CH$_3$ | CH$_2$OCH$_3$ | 203–205 |
| 1 | Q-1(R$_5$ = CH$_3$) | — | H | H | OCH$_3$ | CH$_2$OCH$_3$ | |
| 1 | Q-1(R$_5$ = CH$_3$) | — | H | H | OCH$_3$ | C$_2$H$_5$ | |
| 1 | Q-1(R$_5$ = CH$_3$) | — | H | H | OC$_2$H$_5$ | OCH$_3$ | |
| 1 | Q-1(R$_5$ = CH$_3$) | — | H | H | OCH$_2$CF$_3$ | OCH$_3$ | |
| 1 | Q-1(R$_5$ = CH$_3$) | — | H | H | CF$_3$ | OCH$_3$ | |
| 1 | Q-1(R$_5$ = CH$_3$) | — | H | H | CH$_2$F | OCH$_3$ | |
| 1 | Q-1(R$_5$ = CH$_3$) | — | H | H | CH$_2$Cl | OCH$_3$ | |
| 1 | Q-1(R$_5$ = CH$_3$) | — | H | H | CH$_2$Br | OCH$_3$ | |
| 1 | Q-1(R$_5$ = CH$_3$) | — | H | H | F | OCH$_3$ | |
| 1 | Q-1(R$_5$ = CH$_3$) | — | H | H | I | OCH$_3$ | |
| 1 | Q-1(R$_5$ = CH$_3$) | — | H | H | OCH$_2$CH$_2$F | OCH$_3$ | |
| 1 | Q-1(R$_5$ = CH$_3$) | — | H | H | OCH$_2$CF$_3$ | OCH$_3$ | |
| 1 | Q-1(R$_5$ = CH$_3$) | — | H | H | OCH$_2$CHF$_2$ | CH$_3$ | |
| 1 | Q-1(R$_5$ = CH$_3$) | — | H | H | OCH$_2$CF$_3$ | CH$_3$ | |
| 1 | Q-1(R$_5$ = CH$_3$) | — | H | H | Cl | OC$_2$H$_5$ | 179–181 |
| 1 | Q-1(R$_5$ = CH$_3$) | — | H | H | OC$_2$H$_5$ | NHCH$_3$ | 183–187 |
| 1 | Q-1(R$_5$ = CH$_3$) | — | H | H | OCH$_3$ | CH$_2$SCH$_3$ | 188–193 |
| 1 | Q-1(R$_5$ = C$_2$H$_5$) | — | H | H | OCH$_3$ | OCH$_3$ | 210–212 |
| 1 | Q-1(R$_5$ = C$_2$H$_5$) | — | H | H | CH$_3$ | OCH$_3$ | 194–196 |
| 1 | Q-1(R$_5$ = C$_2$H$_5$) | — | H | H | CH$_3$ | CH$_3$ | 201–203 |
| 1 | Q-1(R$_5$ = C$_2$H$_5$) | — | H | H | Cl | OCH$_3$ | 195–197 |
| 1 | Q-1(R$_5$ = n-C$_3$H$_7$) | — | H | H | OCH$_3$ | OCH$_3$ | 185–189 |
| 1 | Q-1(R$_5$ = n-C$_3$H$_7$) | — | H | H | CH$_3$ | OCH$_3$ | 163–168 |
| 1 | Q-1(R$_5$ = n-C$_3$H$_7$) | — | H | H | CH$_3$ | CH$_3$ | 189–191 |
| 1 | Q-1(R$_5$ = n-C$_3$H$_7$) | — | H | H | Cl | OCH$_3$ | 166–169 |
| 1 | Q-1(R$_5$ = CH(CH$_3$)$_2$) | — | H | H | OCH$_3$ | OCH$_3$ | 186–188 |
| 1 | Q-1(R$_5$ = CH(CH$_3$)$_2$) | — | H | H | CH$_3$ | OCH$_3$ | 191–192 |
| 1 | Q-1(R$_5$ = CH(CH$_3$)$_2$) | — | H | H | CH$_3$ | CH$_3$ | 188–189 |
| 1 | Q-1(R$_5$ = CH(CH$_3$)$_2$) | — | H | H | Cl | OCH$_3$ | 189–191 |
| 1 | Q-1(R$_5$ = n-C$_4$H$_9$) | — | H | H | OCH$_3$ | OCH$_3$ | 182–187 |
| 1 | Q-1(R$_5$ = t-butyl) | — | H | H | OCH$_3$ | OCH$_3$ | |
| 1 | Q-1(R$_5$ = CH$_2$CH(CH$_3$)$_2$) | — | H | H | OCH$_3$ | OCH$_3$ | |
| 1 | Q-1(R$_5$ = CH$_2$CH=CH$_2$) | — | H | H | OCH$_3$ | OCH$_3$ | 184–185 |
| 1 | Q-1(R$_5$ = CH$_2$CH=CH$_2$) | — | H | H | CH$_3$ | CH$_3$ | 189–190 |
| 1 | Q-1(R$_5$ = CH$_2$CH=CH$_2$) | — | H | H | OCH$_3$ | CH$_3$ | 170–172 |
| 1 | Q-1(R$_5$ = CH$_2$CH=CH$_2$) | — | H | H | Cl | OCH$_3$ | 164–166 |
| 1 | Q-1(R$_5$ = CH$_2$CH=CHCH$_3$) | — | H | H | OCH$_3$ | OCH$_3$ | |
| 1 | Q-1(R$_5$ = CH$_2$C≡CH) | — | H | H | OCH$_3$ | OCH$_3$ | |
| 1 | Q-1(R$_5$ = CH$_2$C≡CCH$_3$) | — | H | H | OCH$_3$ | OCH$_3$ | |
| 1 | Q-1(R$_5$ = CH$_2$CN) | — | H | H | OCH$_3$ | OCH$_3$ | 179–183 |
| 1 | Q-1(R$_5$ = CH$_2$CN) | — | H | H | CH$_3$ | OCH$_3$ | 174–176 |
| 1 | Q-1(R$_5$ = CH$_2$CN) | — | H | H | CH$_3$ | CH$_3$ | 195–199 |
| 1 | Q-1(R$_5$ = CH$_2$CN) | — | H | H | Cl | OCH$_3$ | 178–184 |
| 1 | Q-1(R$_5$ = CH$_2$CO$_2$CH$_3$) | — | H | H | OCH$_3$ | OCH$_3$ | 165–170 |
| 1 | Q-1(R$_5$ = CH$_2$CO$_2$C$_2$H$_5$) | — | H | H | OCH$_3$ | OCH$_3$ | |
| 1 | Q-1(R$_5$ = CH(CH$_3$)CO$_2$CH$_3$) | — | H | H | OCH$_3$ | OCH$_3$ | |
| 1 | Q-1(R$_5$ = CH(CH$_3$)CO$_2$C$_2$H$_5$) | — | H | H | OCH$_3$ | OCH$_3$ | |
| 1 | Q-1(R$_5$ = CF$_2$H) | — | H | H | OCH$_3$ | OCH$_3$ | |
| 1 | Q-1(R$_5$ = CF$_2$H) | — | H | H | CH$_3$ | OCH$_3$ | |
| 1 | Q-1(R$_5$ = CF$_2$H) | — | H | H | CH$_3$ | CH$_3$ | |
| 1 | Q-1(R$_5$ = CF$_2$H) | — | H | H | Cl | OCH$_3$ | |
| 1 | Q-1(R$_5$ = CF$_2$H) | — | H | H | Br | OCH$_3$ | |
| 1 | Q-1(R$_5$ = CF$_2$H) | — | H | H | CH$_3$ | H | |
| 1 | Q-1(R$_5$ = CF$_2$H) | — | H | H | OCH$_3$ | H | |
| 1 | Q-1(R$_5$ = CF$_2$H) | — | H | H | OCH$_3$ | CH$_2$OC$_2$H$_5$ | |
| 1 | Q-1(R$_5$ = CF$_2$H) | — | H | H | OCF$_2$H | OCH$_3$ | |
| 1 | Q-1(R$_5$ = CF$_2$H) | — | H | H | OCH$_3$ | CH(OCH$_3$)$_2$ | |
| 1 | Q-1(R$_5$ = CF$_2$H) | — | H | H | CH$_3$ | OC$_2$H$_5$ | |
| 1 | Q-1(R$_5$ = CF$_2$H) | — | H | H | CH$_3$ | CH$_2$OCH$_3$ | |
| 1 | Q-1(R$_5$ = CF$_2$H) | — | H | H | OCH$_3$ | CH$_2$OCH$_3$ | |
| 1 | Q-1(R$_5$ = CF$_2$H) | — | H | H | OCH$_3$ | C$_2$H$_5$ | |
| 1 | Q-1(R$_5$ = CF$_2$H) | — | H | H | OC$_2$H$_5$ | OCH$_3$ | |
| 1 | Q-1(R$_5$ = CF$_2$H) | — | H | H | OCH$_2$CF$_3$ | OCH$_3$ | |
| 1 | Q-1(R$_5$ = CF$_2$H) | — | H | H | CH$_2$F | OCH$_3$ | |
| 1 | Q-1(R$_5$ = CH$_2$CH$_2$F) | — | H | H | OCH$_3$ | OCH$_3$ | |
| 1 | Q-1(R$_5$ = CH$_2$CH$_2$F) | — | H | H | CH$_3$ | OCH$_3$ | |
| 1 | Q-1(R$_5$ = CH$_2$CH$_2$F) | — | H | H | CH$_3$ | CH$_3$ | |
| 1 | Q-1(R$_5$ = CH$_2$CH$_2$F) | — | H | H | Cl | OCH$_3$ | |

TABLE 1-continued

General Formula 1

| J | Q | E | R | R₁ | X | Y | m.p. °C. |
|---|---|---|---|----|---|---|----------|
| 1 | Q-1($R_5$ = CH₂CH₂Cl) | — | H | H | OCH₃ | OCH₃ | |
| 1 | Q-1($R_5$ = CH₂CH₂CH₂F) | — | H | H | OCH₃ | OCH₃ | |
| 1 | Q-1($R_5$ = CH₂CHF₂) | — | H | H | OCH₃ | OCH₃ | |
| 1 | Q-1($R_5$ = CH₂CF₃) | — | H | H | OCH₃ | OCH₃ | |
| 1 | Q-1($R_5$ = CH₂CF₃) | — | H | H | CH₃ | OCH₃ | |
| 1 | Q-1($R_5$ = CH₂CF₃) | — | H | H | CH₃ | CH₃ | |
| 1 | Q-1($R_5$ = CH₂CF₃) | — | H | H | Cl | OCH₃ | |
| 1 | Q-1($R_5$ = CH₂OCH₃) | — | H | H | OCH₃ | OCH₃ | 199–202 |
| 1 | Q-1($R_5$ = CH₂OCH₃) | — | H | H | CH₃ | OCH₃ | 209–210 |
| 1 | Q-1($R_5$ = CH₂OCH₃) | — | H | H | CH₃ | CH₃ | dec. 217 |
| 1 | Q-1($R_5$ = CH₂OCH₃) | — | H | H | Cl | OCH₃ | 203–206 |
| 1 | Q-1($R_5$ = CH₂OCH₂CH₃) | — | H | H | OCH₃ | OCH₃ | |
| 1 | Q-1($R_5$ = CH₂CH₂OCH₃) | — | H | H | OCH₃ | OCH₃ | 175–178 |
| 1 | Q-1($R_5$ = CH₂CH₂OC₂H₅) | — | H | H | OCH₃ | OCH₃ | |
| 1 | Q-2($R_6$ = CH₃) | — | H | H | OCH₃ | OCH₃ | |
| 1 | Q-2($R_6$ = C₂H₅) | — | H | H | OCH₃ | OCH₃ | |
| 1 | Q-2($R_6$ = CH(CH₃)₂) | — | H | H | OCH₃ | OCH₃ | |
| 1 | Q-3($R_6$ = CH₃) | — | H | H | OCH₃ | OCH₃ | |
| 1 | Q-4($R_6$ = CH₃) | — | H | H | OCH₃ | OCH₃ | |
| 1 | Q-5($R_6$ = CH₃) | — | H | H | OCH₃ | OCH₃ | |
| 1 | Q-5($R_6$ = CH₃) | — | H | H | CH₃ | OCH₃ | |
| 1 | Q-5($R_6$ = CH₃) | — | H | H | CH₃ | CH₃ | |
| 1 | Q-5($R_6$ = CH₃) | — | H | H | Cl | OCH₃ | |
| 1 | Q-5($R_6$ = n-C₃H₇) | — | H | H | OCH₃ | OCH₃ | |
| 1 | Q-6($R_6$ = CH₃) | — | H | H | OCH₃ | OCH₃ | |
| 1 | Q-7($R_5$, $R_6$ = CH₃) | — | H | H | OCH₃ | OCH₃ | |
| 1 | Q-7($R_5$, $R_6$ = CH₃) | — | H | H | CH₃ | OCH₃ | |
| 1 | Q-7($R_5$, $R_6$ = CH₃) | — | H | H | CH₃ | CH₃ | |
| 1 | Q-7($R_5$, $R_6$ = CH₃) | — | H | H | Cl | OCH₃ | |
| 1 | Q-7($R_5$ = C₂H₅, $R_6$ = CH₃) | — | H | H | OCH₃ | OCH₃ | |
| 1 | Q-7($R_5$ = C₂H₅, $R_6$ = CH₃) | — | H | H | CH₃ | OCH₃ | |
| 1 | Q-7($R_5$ = C₂H₅, $R_6$ = CH₃) | — | H | H | CH₃ | CH₃ | |
| 1 | Q-7($R_5$ = C₂H₅, $R_6$ = CH₃) | — | H | H | Cl | OCH₃ | |
| 1 | Q-8 | — | H | H | OCH₃ | OCH₃ | |
| 1 | Q-9 | — | H | H | OCH₃ | OCH₃ | |
| 1 | Q-9 | — | H | H | CH₃ | OCH₃ | |
| 1 | Q-9 | — | H | H | CH₃ | CH₃ | dec. 207 |
| 1 | Q-9 | — | H | H | Cl | OCH₃ | |
| 1 | Q-10 | — | H | H | OCH₃ | OCH₃ | |
| 1 | Q-10 | — | H | H | CH₃ | OCH₃ | |
| 1 | Q-10 | — | H | H | CH₃ | CH₃ | |
| 1 | Q-10 | — | H | H | Cl | OCH₃ | |
| 1 | Q-11 | — | H | H | OCH₃ | OCH₃ | |
| 1 | Q-12 | — | H | H | OCH₃ | OCH₃ | |
| 1 | Q-13 | — | H | H | OCH₃ | OCH₃ | |
| 1 | Q-14($R_6$ = CH₃) | — | H | H | OCH₃ | OCH₃ | |
| 1 | Q-15($R_7$ = CH₃) | — | H | H | OCH₃ | OCH₃ | |
| 1 | Q-15($R_7$ = CH₃) | — | H | H | CH₃ | OCH₃ | |
| 1 | Q-15($R_7$ = CH₃) | — | H | H | CH₃ | CH₃ | |
| 1 | Q-15($R_7$ = CH₃) | — | H | H | Cl | OCH₃ | |
| 1 | Q-15($R_7$ = C₂H₅) | — | H | H | OCH₃ | OCH₃ | |
| 1 | Q-15($R_7$ = C₂H₅) | — | H | H | CH₃ | OCH₃ | |
| 1 | Q-15($R_7$ = C₂H₅) | — | H | H | CH₃ | CH₃ | |
| 1 | Q-15($R_7$ = C₂H₅) | — | H | H | Cl | OCH₃ | |
| 1 | Q-15($R_7$ = n-C₃H₇) | — | H | H | OCH₃ | OCH₃ | |
| 1 | Q-15($R_7$ = n-C₃H₇) | — | H | H | CH₃ | OCH₃ | |
| 1 | Q-15($R_7$ = n-C₃H₇) | — | H | H | CH₃ | CH₃ | |
| 1 | Q-15($R_7$ = n-C₃H₇) | — | H | H | Cl | OCH₃ | |
| 1 | Q-15($R_7$ = CH(CH₃)₂) | — | H | H | OCH₃ | OCH₃ | |
| 1 | Q-15($R_7$ = CH(CH₃)₂) | — | H | H | CH₃ | OCH₃ | |
| 1 | Q-15($R_7$ = CH(CH₃)₂) | — | H | H | CH₃ | CH₃ | |
| 1 | Q-15($R_7$ = CH(CH₃)₂) | — | H | H | Cl | OCH₃ | |
| 1 | Q-15($R_7$ = n-C₄H₉) | — | H | H | OCH₃ | OCH₃ | |
| 1 | Q-15($R_7$ = t-butyl) | — | H | H | OCH₃ | OCH₃ | |
| 1 | Q-15($R_7$ = t-butyl) | — | H | H | CH₃ | OCH₃ | |
| 1 | Q-15($R_7$ = t-butyl) | — | H | H | CH₃ | CH₃ | |
| 1 | Q-15($R_7$ = t-butyl) | — | H | H | Cl | OCH₃ | |
| 1 | Q-16($R_7$ = CH₃) | — | H | H | OCH₃ | OCH₃ | |
| 1 | Q-16($R_7$ = CH₃) | — | H | H | CH₃ | OCH₃ | |
| 1 | Q-16($R_7$ = CH₃) | — | H | H | CH₃ | CH₃ | |
| 1 | Q-16($R_7$ = CH₃) | — | H | H | Cl | OCH₃ | |
| 1 | Q-1($R_5$ = CH₃) | O | H | H | OCH₃ | OCH₃ | 153–158 |
| 1 | Q-1($R_5$ = CH₃) | O | H | H | CH₃ | OCH₃ | 150–156 |
| 1 | Q-1($R_5$ = CH₃) | O | H | H | CH₃ | CH₃ | 99–104 |
| 1 | Q-1($R_5$ = CH₃) | O | H | H | Cl | OCH₃ | 175–178 |
| 1 | Q-1($R_5$ = CH₃) | O | H | H | Cl | OC₂H₅ | |
| 1 | Q-1($R_5$ = CH₃) | O | H | H | CH₃ | H | |
| 1 | Q-1($R_5$ = CH₃) | O | H | H | OCH₃ | H | |
| 1 | Q-1($R_5$ = CH₃) | O | H | H | OCH₃ | CH₂OCH₃ | |
| 1 | Q-1($R_5$ = CH₃) | O | H | H | CH₃ | CH₂OCH₃ | |

TABLE 1-continued

General Formula 1

| J | Q | E | R | R$_1$ | X | Y | m.p. °C. |
|---|---|---|---|---|---|---|---|
| 1 | Q-1(R$_5$ = CH$_3$) | O | H | H | OCF$_2$H | OCH$_3$ | 129–133 |
| 1 | Q-1(R$_5$ = CH$_3$) | O | H | H | OCH$_3$ | CH(OCH$_3$)$_2$ | |
| 1 | Q-1(R$_5$ = CH$_3$) | O | H | H | CH$_3$ | OC$_2$H$_5$ | |
| 1 | Q-1(R$_5$ = CH$_3$) | O | H | H | OCH$_3$ | CH$_2$OC$_2$H$_5$ | |
| 1 | Q-1(R$_5$ = CH$_3$) | O | H | H | OCH$_3$ | C$_2$H$_5$ | |
| 1 | Q-1(R$_5$ = CH$_3$) | O | H | H | OC$_2$H$_5$ | OCH$_3$ | |
| 1 | Q-1(R$_5$ = CH$_3$) | O | H | H | OCH$_2$CF$_3$ | OCH$_3$ | |
| 1 | Q-1(R$_5$ = CH$_3$) | O | H | H | CH$_2$F | OCH$_3$ | |
| 1 | Q-1(R$_5$ = CH$_3$) | O | H | H | OCH$_2$CF$_3$ | NHCH$_3$ | |
| 1 | Q-1(R$_5$ = CH$_3$) | O | H | H | OCH$_3$ | CH$_2$SCH$_3$ | |
| 1 | Q-1(R$_5$ = CH$_3$) | O | H | H | Br | OCH$_3$ | |
| 1 | Q-1(R$_5$ = C$_2$H$_5$) | O | H | H | OCH$_3$ | OCH$_3$ | |
| 1 | Q-1(R$_5$ = C$_2$H$_5$) | O | H | H | CH$_3$ | OCH$_3$ | |
| 1 | Q-1(R$_5$ = C$_2$H$_5$) | O | H | H | CH$_3$ | CH$_3$ | |
| 1 | Q-1(R$_5$ = C$_2$H$_5$) | O | H | H | Cl | OCH$_3$ | |
| 1 | Q-1(R$_5$ = n-C$_3$H$_7$) | O | H | H | OCH$_3$ | OCH$_3$ | |
| 1 | Q-1(R$_5$ = n-C$_3$H$_7$) | O | H | H | CH$_3$ | OCH$_3$ | |
| 1 | Q-1(R$_5$ = n-C$_3$H$_7$) | O | H | H | CH$_3$ | CH$_3$ | |
| 1 | Q-1(R$_5$ = n-C$_3$H$_7$) | O | H | H | Cl | OCH$_3$ | |
| 1 | Q-1(R$_5$ = CH(CH$_3$)$_2$) | O | H | H | OCH$_3$ | OCH$_3$ | |
| 1 | Q-1(R$_5$ = CH(CH$_3$)$_2$) | O | H | H | OCH$_3$ | CH$_3$ | |
| 1 | Q-1(R$_5$ = CH(CH$_3$)$_2$) | O | H | H | CH$_3$ | CH$_3$ | |
| 1 | Q-1(R$_5$ = CH(CH$_3$)$_2$) | O | H | H | Cl | OCH$_3$ | |
| 1 | Q-1(R$_5$ = CF$_2$H) | O | H | H | OCH$_3$ | OCH$_3$ | |
| 1 | Q-1(R$_5$ = CF$_2$H) | O | H | H | OCH$_3$ | CH$_3$ | |
| 1 | Q-1(R$_5$ = CF$_2$H) | O | H | H | CH$_3$ | OCH$_3$ | |
| 1 | Q-1(R$_5$ = CF$_2$H) | O | H | H | Cl | OCH$_3$ | |
| 1 | Q-1(R$_5$ = CH$_2$CN) | O | H | H | OCH$_3$ | OCH$_3$ | |
| 1 | Q-1(R$_5$ = CH$_2$CN) | O | H | H | CH$_3$ | OCH$_3$ | |
| 1 | Q-1(R$_5$ = CH$_2$CN) | O | H | H | CH$_3$ | CH$_3$ | |
| 1 | Q-1(R$_5$ = CH$_2$CN) | O | H | H | Cl | OCH$_3$ | |
| 1 | Q-1(R$_5$ = CH$_2$CH=CH$_2$) | O | H | H | OCH$_3$ | OCH$_3$ | |
| 1 | Q-1(R$_5$ = CH$_2$CH=CH$_2$) | O | H | H | CH$_3$ | OCH$_3$ | |
| 1 | Q-1(R$_5$ = CH$_2$CH=CH$_2$) | O | H | H | CH$_3$ | CH$_3$ | |
| 1 | Q-1(R$_5$ = CH$_2$CH=CH$_2$) | O | H | H | Cl | OCH$_3$ | |
| 1 | Q-7(R$_5$, R$_6$ = CH$_3$) | O | H | H | OCH$_3$ | OCH$_3$ | |
| 1 | Q-9 | O | H | H | OCH$_3$ | OCH$_3$ | |
| 1 | Q-10 | O | H | H | OCH$_3$ | OCH$_3$ | 131–135 |
| 1 | Q-10 | O | H | H | CH$_3$ | OCH$_3$ | 175–176 |
| 1 | Q-10 | O | H | H | CH$_3$ | CH$_3$ | 58–72 |
| 1 | Q-10 | O | H | H | Cl | OCH$_3$ | 120–123 |
| 1 | Q-15(R$_7$ = CH$_3$) | O | H | H | OCH$_3$ | OCH$_3$ | |
| 1 | Q-1(R$_5$ = CH$_3$) | CH$_2$ | H | H | OCH$_3$ | OCH$_3$ | 195–197 |
| 1 | Q-1(R$_5$ = CH$_3$) | CH$_2$ | H | H | CH$_3$ | OCH$_3$ | 171–172 |
| 1 | Q-1(R$_5$ = CH$_3$) | CH$_2$ | H | H | CH$_3$ | CH$_3$ | 194–197 |
| 1 | Q-1(R$_5$ = CH$_3$) | CH$_2$ | H | H | Cl | OCH$_3$ | 177–180 |
| 1 | Q-2(R$_6$ = CH$_3$) | CH$_2$ | H | H | OCH$_3$ | OCH$_3$ | |
| 1 | Q-7(R$_5$, R$_6$ = CH$_3$) | CH$_2$ | H | H | OCH$_3$ | OCH$_3$ | |
| 1 | Q-7(R$_5$, R$_6$ = CH$_3$) | CH$_2$ | H | H | CH$_3$ | OCH$_3$ | |
| 1 | Q-7(R$_5$, R$_6$ = CH$_3$) | CH$_2$ | H | H | CH$_3$ | CH$_3$ | |
| 1 | Q-7(R$_5$, R$_6$ = CH$_3$) | CH$_2$ | H | H | Cl | OCH$_3$ | |
| 1 | Q-9 | CH$_2$ | H | H | OCH$_3$ | OCH$_3$ | |
| 1 | Q-10 | CH$_2$ | H | H | OCH$_3$ | OCH$_3$ | |
| 1 | Q-15 | CH$_2$ | H | H | OCH$_3$ | OCH$_3$ | |
| 1 | Q-1(R$_5$ = CH$_3$) | — | CH$_3$ | H | OCH$_3$ | OCH$_3$ | |
| 1 | Q-7(R$_5$, R$_6$ = CH$_3$) | — | CH$_3$ | H | OCH$_3$ | OCH$_3$ | |
| 1 | Q-15(R$_7$ = CH$_3$) | — | CH$_3$ | H | OCH$_3$ | OCH$_3$ | |
| 1 | Q-1(R$_5$ = CH$_3$) | — | H | 3-F | OCH$_3$ | OCH$_3$ | |
| 1 | Q-1(R$_5$ = CH$_3$) | — | H | 5-Cl | OCH$_3$ | OCH$_3$ | 203–206 |
| 1 | Q-1(R$_5$ = CH$_3$) | — | H | 6-Br | OCH$_3$ | OCH$_3$ | |
| 1 | Q-1(R$_5$ = CH$_3$) | — | H | 5-CH$_3$ | OCH$_3$ | OCH$_3$ | |
| 1 | Q-1(R$_5$ = CH$_3$) | — | H | 6-C$_2$H$_5$ | OCH$_3$ | OCH$_3$ | |
| 1 | Q-1(R$_5$ = CH$_3$) | — | H | 5-OCH$_3$ | OCH$_3$ | OCH$_3$ | |
| 1 | Q-1(R$_5$ = CH$_3$) | — | H | 3-OC$_2$H$_5$ | OCH$_3$ | OCH$_3$ | |
| 1 | Q-1(R$_5$ = CH$_3$) | — | H | 6-OCH(CH$_3$)$_2$ | OCH$_3$ | OCH$_3$ | |
| 1 | Q-1(R$_5$ = CH$_3$) | — | H | 5-SCH$_3$ | OCH$_3$ | OCH$_3$ | |
| 1 | Q-1(R$_5$ = CH$_3$) | — | H | 6-SC$_2$H$_5$ | OCH$_3$ | OCH$_3$ | |
| 1 | Q-1(R$_5$ = CH$_3$) | — | H | 3-SCH(CH$_3$)$_2$ | OCH$_3$ | OCH$_3$ | |
| 1 | Q-1(R$_5$ = CH$_3$) | — | H | 5-CH$_2$F | OCH$_3$ | OCH$_3$ | |
| 1 | Q-1(R$_5$ = CH$_3$) | — | H | 5-CF$_3$ | OCH$_3$ | OCH$_3$ | |
| 1 | Q-1(R$_5$ = CH$_3$) | — | H | 5-CH$_2$CH$_2$Br | OCH$_3$ | OCH$_3$ | |
| 1 | Q-1(R$_5$ = CH$_3$) | — | H | 6-OCF$_2$H | OCH$_3$ | OCH$_3$ | |
| 1 | Q-1(R$_5$ = CH$_3$) | — | H | 6-OCH$_2$CH$_2$Br | OCH$_3$ | OCH$_3$ | |
| 1 | Q-1(R$_5$ = CH$_3$) | — | H | 6-OCH(CH$_3$)CH$_2$Cl | OCH$_3$ | OCH$_3$ | |
| 1 | Q-1(R$_5$ = CH$_3$) | — | H | 5-SCH$_2$F | OCH$_3$ | OCH$_3$ | |
| 1 | Q-1(R$_5$ = CH$_3$) | — | H | 6-SCH$_2$CH$_2$Br | OCH$_3$ | OCH$_3$ | |
| 1 | Q-1(R$_5$ = CH$_3$) | — | H | 6-SCH(CH$_3$)CH$_2$Cl | OCH$_3$ | OCH$_3$ | |
| 1 | Q-1(R$_5$ = CH$_3$) | — | H | 4-NO$_2$ | OCH$_3$ | OCH$_3$ | |
| 1 | Q-1(R$_5$ = CH$_3$) | O | H | 5-Cl | OCH$_3$ | OCH$_3$ | |
| 1 | Q-1(R$_5$ = CH$_3$) | O | H | 5-CH$_3$ | OCH$_3$ | OCH$_3$ | |

TABLE 1-continued

General Formula 1

| J | Q | E | R | R$_1$ | X | Y | m.p. °C. |
|---|---|---|---|---|---|---|---|
| 1 | Q-1(R$_5$ = CH$_3$) | O | H | 5-OCH$_3$ | OCH$_3$ | OCH$_3$ | |
| 1 | Q-1(R$_5$ = CH$_3$) | O | H | 5-SCH$_3$ | OCH$_3$ | OCH$_3$ | |
| 1 | Q-1(R$_5$ = C$_2$H$_5$) | — | H | H | C$_2$H$_5$ | OCH$_3$ | |
| 1 | Q-1(R$_5$ = C$_2$H$_5$) | — | H | H | CF$_3$ | OCH$_3$ | |
| 1 | Q-1(R$_5$ = C$_2$H$_5$) | — | H | H | OCH$_3$ | H | |
| 1 | Q-1(R$_5$ = CH$_3$) | — | H | H | NH$_2$ | OCH$_3$ | |
| 1 | Q-1(R$_5$ = CH$_3$) | — | H | H | n-C$_3$H$_7$ | OCH$_3$ | |
| 1 | Q-1(R$_5$ = CH$_3$) | — | H | H | NHCH$_3$ | OCH$_3$ | |
| 1 | Q-1(R$_5$ = CH$_3$) | — | H | H | OCH$_3$ | SCH$_3$ | |
| 1 | Q-1(R$_5$ = CH$_3$) | — | H | H | OCH$_3$ | SCF$_2$H | |
| 1 | Q-1(R$_5$ = CH$_3$) | — | H | H | OCH$_3$ | OCH$_2$C≡CH | |
| 1 | Q-1(R$_5$ = CH$_3$) | — | H | H | OCH$_3$ | C≡CH | |
| 1 | Q-1(R$_5$ = CH$_3$) | — | H | H | OCH$_3$ | N(CH$_3$)$_2$ | |
| 1 | Q-1(R$_5$ = CH$_3$) | — | H | H | OCH$_3$ | cyclopropyl | |
| 1 | Q-1(R$_5$ = CH$_3$) | — | H | H | OCH$_3$ | NH$_2$ | |
| 1 | Q-10 | — | H | H | OCH$_3$ | OCF$_2$H | |
| 1 | Q-1(R$_5$ = CH$_3$) | — | H | H | OCH$_3$ | CF$_3$ | |
| 1 | Q-1(R$_5$ = CH$_3$) | — | H | H | OCH$_3$ | OCH$_2$CH$_2$OCH$_3$ | |
| 1 | Q-1(R$_5$ = CH$_3$) | — | H | H | OCH$_3$ | CH$_2$SCH$_3$ | |
| 1 | Q-1(R$_5$ = CH$_3$) | — | H | H | OCH$_3$ | CHO | |
| 1 | Q-1(R$_5$ = CH$_3$) | — | H | H | OCH$_3$ | COCH$_3$ | |
| 1 | Q-1(R$_5$ = CH$_3$) | — | H | H | OCH$_3$ | CH(SCH$_3$)OC$_2$H$_5$ | |
| 1 | Q-1(R$_5$ = CH$_3$) | — | H | H | OCH$_3$ | C(CH$_3$)(SCH$_3$)$_2$ | |
| 1 | Q-1(R$_5$ = CH$_3$) | — | H | H | OCH$_3$ | C(SC$_2$H$_5$)$_2$ | |
| 1 | Q-1(R$_5$ = CH$_3$) | — | H | H | OCH$_3$ | 1,3-dioxolan-2-yl | |
| 1 | Q-1(R$_5$ = CH$_3$) | — | H | H | OCH$_3$ | 2-methyl-1,3-oxathiolan-2-yl | |
| 1 | Q-1(R$_5$ = CH$_3$) | — | H | H | OCH$_3$ | 1,3-oxathian-2-yl | |
| 1 | Q-1(R$_5$ = CH$_3$) | — | H | H | OCH$_3$ | 2-methyl-1,3-dithian-2-yl | |
| 1 | Q-1(R$_5$ = CH$_3$) | — | H | H | OCH$_3$ | 4-methyl-1,3-dioxolan-2-yl | |
| 1 | Q-1(R$_5$ = CH$_3$) | — | H | H | OCH$_3$ | 2,4-dimethyl-1,3-dithiolan-2-yl | |
| 1 | Q-1(R$_5$ = CH$_3$) | — | H | H | OCH$_3$ | N(OCH$_3$)(CH$_3$) dithiolan-2-yl | |
| 1 | Q-1(R$_5$ = CH$_3$) | — | H | H | OCH$_3$ | C≡CCH$_3$ | |
| 1 | Q-1(R$_5$ = CH$_3$) | — | H | H | OCH$_3$ | cyclopropyl | |
| 2a | Q-1(R$_5$ = CH$_3$) | — | H | H | OCH$_3$ | OCH$_3$ | 150–155 |
| 2a | Q-1(R$_5$ = CH$_3$) | — | H | H | CH$_3$ | OCH$_3$ | 190–193 |
| 2a | Q-1(R$_5$ = CH$_3$) | — | H | H | CH$_3$ | CH$_3$ | 164–168 |
| 2a | Q-1(R$_5$ = CH$_3$) | — | H | H | Cl | OCH$_3$ | 205–207 |
| 2a | Q-1(R$_5$ = C$_2$H$_5$) | — | H | H | OCH$_3$ | OCH$_3$ | |
| 2a | Q-1(R$_5$ = C$_2$H$_5$) | — | H | H | CH$_3$ | OCH$_3$ | |
| 2a | Q-1(R$_5$ = C$_2$H$_5$) | — | H | H | CH$_3$ | CH$_3$ | |
| 2a | Q-1(R$_5$ = C$_2$H$_5$) | — | H | H | Cl | OCH$_3$ | |
| 2a | Q-1(R$_5$ = n-C$_3$H$_7$) | — | H | H | OCH$_3$ | OCH$_3$ | |
| 2a | Q-1(R$_5$ = n-C$_3$H$_7$) | — | H | H | CH$_3$ | OCH$_3$ | |
| 2a | Q-1(R$_5$ = n-C$_3$H$_7$) | — | H | H | CH$_3$ | CH$_3$ | |
| 2a | Q-1(R$_5$ = n-C$_3$H$_7$) | — | H | H | Cl | OCH$_3$ | |
| 2a | Q-1(R$_5$ = CH(CH$_3$)$_2$) | — | H | H | OCH$_3$ | OCH$_3$ | |
| 2a | Q-1(R$_5$ = CH(CH$_3$)$_2$) | — | H | H | CH$_3$ | OCH$_3$ | |
| 2a | Q-1(R$_5$ = CH(CH$_3$)$_2$) | — | H | H | CH$_3$ | CH$_3$ | |
| 2a | Q-1(R$_5$ = CH(CH$_3$)$_2$) | — | H | H | Cl | OCH$_3$ | |
| 2a | Q-1(R$_5$ = CH$_2$CN) | — | H | H | OCH$_3$ | OCH$_3$ | 119–122 |
| 2a | Q-1(R$_5$ = CH$_2$CN) | — | H | H | CH$_3$ | OCH$_3$ | 183–185 |
| 2a | Q-1(R$_5$ = CH$_2$CN) | — | H | H | CH$_3$ | CH$_3$ | |
| 2a | Q-1(R$_5$ = CH$_2$CN) | — | H | H | Cl | OCH$_3$ | 172–175 |
| 2a | Q-1(R$_5$ = CH$_2$CH=CH$_2$) | — | H | H | OCH$_3$ | OCH$_3$ | 94–97 |
| 2a | Q-1(R$_5$ = CH$_2$CH=CH$_2$) | — | H | H | OCH$_3$ | CH$_3$ | 172–174 |
| 2a | Q-1(R$_5$ = CH$_2$CH=CH$_2$) | — | H | H | CH$_3$ | CH$_3$ | 193–197 |
| 2a | Q-1(R$_5$ = CH$_2$CH=CH$_2$) | — | H | H | Cl | OCH$_3$ | 147–148 |
| 2a | Q-1(R$_5$ = CF$_2$H) | — | H | H | OCH$_3$ | OCH$_3$ | |
| 2a | Q-1(R$_5$ = CF$_2$H) | — | H | H | CH$_3$ | OCH$_3$ | |
| 2a | Q-1(R$_5$ = CF$_2$H) | — | H | H | CH$_3$ | CH$_3$ | |
| 2a | Q-1(R$_5$ = CF$_2$H) | — | H | H | Cl | OCH$_3$ | |
| 2a | Q-7(R$_5$, R$_6$ = CH$_3$) | — | H | H | OCH$_3$ | OCH$_3$ | |
| 2a | Q-7(R$_5$, R$_6$ = CH$_3$) | — | H | H | CH$_3$ | OCH$_3$ | |
| 2a | Q-7(R$_5$, R$_6$ = CH$_3$) | — | H | H | CH$_3$ | CH$_3$ | |
| 2a | Q-7(R$_5$, R$_6$ = CH$_3$) | — | H | H | Cl | OCH$_3$ | |
| 2a | Q-15(R$_7$ = CH$_3$) | — | H | H | OCH$_3$ | OCH$_3$ | |
| 2a | Q-15(R$_7$ = CH$_3$) | — | H | H | CH$_3$ | OCH$_3$ | |
| 2a | Q-15(R$_7$ = CH$_3$) | — | H | H | CH$_3$ | CH$_3$ | |
| 2a | Q-15(R$_7$ = CH$_3$) | — | H | H | Cl | OCH$_3$ | |
| 2b | Q-1(R$_5$ = CH$_3$) | — | H | H | OCH$_3$ | OCH$_3$ | |
| 2b | Q-1(R$_5$ = CH$_3$) | — | H | H | CH$_3$ | OCH$_3$ | |
| 2b | Q-1(R$_5$ = CH$_3$) | — | H | H | CH$_3$ | CH$_3$ | |
| 2b | Q-1(R$_5$ = CH$_3$) | — | H | H | Cl | OCH$_3$ | |
| 2b | Q-7(R$_5$, R$_6$ = CH$_3$) | — | H | H | OCH$_3$ | OCH$_3$ | |
| 2b | Q-7(R$_5$, R$_6$ = CH$_3$) | — | H | H | CH$_3$ | OCH$_3$ | |

TABLE 1-continued

General Formula 1

| J | Q | E | R | R$_1$ | X | Y | m.p. °C. |
|---|---|---|---|---|---|---|---|
| 2b | Q-1(R$_5$, R$_6$ = CH$_3$) | — | H | H | CH$_3$ | CH$_3$ | |
| 2b | Q-1(R$_5$, R$_6$ = CH$_3$) | — | H | H | Cl | OCH$_3$ | |
| 2c | Q-1(R$_5$ = CH$_3$) | — | H | H | OCH$_3$ | OCH$_3$ | |
| 2c | Q-1(R$_5$ = CH$_3$) | — | H | H | CH$_3$ | OCH$_3$ | |
| 2c | Q-1(R$_5$ = CH$_3$) | — | H | H | CH$_3$ | CH$_3$ | |
| 2c | Q-1(R$_5$ = CH$_3$) | — | H | H | Cl | OCH$_3$ | |
| 3a | (R$_2$ = CH$_3$)Q-1(R$_5$ = CH$_3$) | — | H | H | OCH$_3$ | OCH$_3$ | |
| 3a | (R$_2$ = CH$_3$)Q-1(R$_5$ = CH$_3$) | — | H | H | CH$_3$ | OCH$_3$ | |
| 3a | (R$_2$ = CH$_3$)Q-1(R$_5$ = CH$_3$) | — | H | H | CH$_3$ | CH$_3$ | |
| 3a | (R$_2$ = CH$_3$)Q-1(R$_5$ = CH$_3$) | — | H | H | Cl | OCH$_3$ | |
| 3b | (R$_2$ = C$_2$H$_5$)Q-1(R$_5$ = CH$_3$) | — | H | H | OCH$_3$ | OCH$_3$ | |
| 3c | (R$_2$ = CH$_3$)Q-1(R$_5$ = CH$_3$) | — | H | H | OCH$_3$ | OCH$_3$ | |
| 3c | (R$_2$ = CH$_3$)Q-1(R$_5$ = CH$_3$) | — | H | H | CH$_3$ | OCH$_3$ | |
| 3c | (R$_2$ = CH$_3$)Q-1(R$_5$ = CH$_3$) | — | H | H | CH$_3$ | CH$_3$ | |
| 3c | (R$_2$ = CH$_3$)Q-1(R$_5$ = CH$_3$) | — | H | H | Cl | OCH$_3$ | |
| 3c | (R$_2$ = CH$_3$)Q-7(R$_5$, R$_6$ = CH$_3$) | — | H | H | OCH$_3$ | OCH$_3$ | |
| 3c | (R$_2$ = CH$_3$)Q-7(R$_5$, R$_6$ = CH$_3$) | — | H | H | CH$_3$ | OCH$_3$ | |
| 3c | (R$_2$ = CH$_3$)Q-7(R$_5$, R$_6$ = CH$_3$) | — | H | H | CH$_3$ | CH$_3$ | |
| 3c | (R$_2$ = CH$_3$)Q-7(R$_5$, R$_6$ = CH$_3$) | — | H | H | Cl | OCH$_3$ | |
| 3d | (R$_2$ = CH$_3$)Q-1(R$_5$ = CH$_3$) | — | H | H | OCH$_3$ | OCH$_3$ | |
| 3d | (R$_2$ = CH$_3$)Q-1(R$_5$ = CH$_3$) | — | H | H | CH$_3$ | OCH$_3$ | |
| 3d | (R$_2$ = CH$_3$)Q-1(R$_5$ = CH$_3$) | — | H | H | CH$_3$ | CH$_3$ | |
| 3d | (R$_2$ = CH$_3$)Q-1(R$_5$ = CH$_3$) | — | H | H | Cl | OCH$_3$ | |
| 3d | (R$_2$ = CH$_3$)Q-7(R$_5$, R$_6$ = CH$_3$) | — | H | H | OCH$_3$ | OCH$_3$ | |
| 3d | (R$_2$ = CH$_3$)Q-7(R$_5$, R$_6$ = CH$_3$) | — | H | H | CH$_3$ | OCH$_3$ | |
| 3d | (R$_2$ = CH$_3$)Q-7(R$_5$, R$_6$ = CH$_3$) | — | H | H | CH$_3$ | CH$_3$ | |
| 3d | (R$_2$ = CH$_3$)Q-7(R$_5$, R$_6$ = CH$_3$) | — | H | H | Cl | OCH$_3$ | |
| 3d | (R$_2$ = C$_2$H$_5$)Q-7(R$_5$ = CH$_3$) | — | H | H | OCH$_3$ | OCH$_3$ | |
| 3d | (R$_2$ = C$_2$H$_5$)Q-7(R$_5$ = CH$_3$) | — | H | H | CH$_3$ | OCH$_3$ | |
| 3d | (R$_2$ = C$_2$H$_5$)Q-7(R$_5$ = CH$_3$) | — | H | H | CH$_3$ | CH$_3$ | |
| 3d | (R$_2$ = C$_2$H$_5$)Q-7(R$_5$ = CH$_3$) | — | H | H | Cl | OCH$_3$ | |
| 3d | (R$_2$ = n-C$_3$H$_7$)Q-1(R$_5$ = CH$_3$) | — | H | H | OCH$_3$ | OCH$_3$ | |
| 3d | (R$_2$ = n-C$_3$H$_7$)Q-1(R$_5$ = CH$_3$) | — | H | H | CH$_3$ | OCH$_3$ | |
| 3d | (R$_2$ = n-C$_3$H$_7$)Q-1(R$_5$ = CH$_3$) | — | H | H | CH$_3$ | CH$_3$ | |
| 3d | (R$_2$ = n-C$_3$H$_7$)Q-1(R$_5$ = CH$_3$) | — | H | H | Cl | OCH$_3$ | |
| 3d | (R$_2$ = CH(CH$_3$)$_2$)Q-1(R$_5$ = CH$_3$) | — | H | H | OCH$_3$ | OCH$_3$ | |
| 3d | (R$_2$ = CH(CH$_3$)$_2$)Q-1(R$_5$ = CH$_3$) | — | H | H | CH$_3$ | OCH$_3$ | |
| 3d | (R$_2$ = CH(CH$_3$)$_2$)Q-1(R$_5$ = CH$_3$) | — | H | H | CH$_3$ | CH$_3$ | |
| 3d | (R$_2$ = CH(CH$_3$)$_2$)Q-1(R$_5$ = CH$_3$) | — | H | H | Cl | OCH$_3$ | |
| 4 | Q-1(R$_5$ = CH$_3$) | — | H | H | OCH$_3$ | OCH$_3$ | dec. 187 |
| 4 | Q-1(R$_5$ = CH$_3$) | — | H | H | CH$_3$ | OCH$_3$ | dec. 148 |
| 4 | Q-1(R$_5$ = CH$_3$) | — | H | H | CH$_3$ | CH$_3$ | dec. 146 |
| 4 | Q-1(R$_5$ = CH$_3$) | — | H | H | Cl | OCH$_3$ | dec. 185 |
| 4 | Q-7(R$_5$, R$_6$ = CH$_3$) | — | H | H | OCH$_3$ | OCH$_3$ | |
| 4 | Q-7(R$_5$, R$_6$ = CH$_3$) | — | H | H | CH$_3$ | OCH$_3$ | |
| 4 | Q-7(R$_5$, R$_6$ = CH$_3$) | — | H | H | CH$_3$ | CH$_3$ | |
| 4 | Q-7(R$_5$, R$_6$ = CH$_3$) | — | H | H | Cl | OCH$_3$ | |
| 5 | Q-15(R$_7$ = CH$_3$) | — | H | H | OCH$_3$ | OCH$_3$ | |
| 5 | Q-15(R$_7$ = CH$_3$) | — | H | H | CH$_3$ | OCH$_3$ | |
| 5 | Q-15(R$_7$ = CH$_3$) | — | H | H | CH$_3$ | CH$_3$ | |
| 5 | Q-15(R$_7$ = CH$_3$) | — | H | H | Cl | OCH$_3$ | |
| 1 | Q-1(R$_5$ = CH$_3$) | — | H | H | OCH$_3$ | OCH$_2$CH=CH$_2$ | |
| 1 | Q-1(R$_5$ = H) | — | H | H | OCH$_3$ | OCH$_3$ | |
| 1 | Q-1(R$_5$ = H) | — | H | H | CH$_3$ | OCH$_3$ | |
| 1 | Q-1(R$_5$ = H) | — | H | H | CH$_3$ | CH$_3$ | |
| 1 | Q-1(R$_5$ = H) | — | H | H | Cl | OCH$_3$ | |
| 1 | Q-15(R$_7$ = H) | — | H | H | OCH$_3$ | OCH$_3$ | |
| 1 | Q-18(R$_6$ = CH$_3$) | — | H | H | OCH$_3$ | OCH$_3$ | |
| 1 | Q-18(R$_6$ = CH$_3$) | — | H | H | CH$_3$ | OCH$_3$ | |
| 1 | Q-18(R$_6$ = CH$_3$) | — | H | H | CH$_3$ | CH$_3$ | |
| 1 | Q-18(R$_6$ = CH$_3$) | — | H | H | Cl | OCH$_3$ | |
| 1 | Q-19 | — | H | H | OCH$_3$ | OCH$_3$ | |
| 1 | Q-19 | — | H | H | CH$_3$ | OCH$_3$ | |
| 1 | Q-19 | — | H | H | CH$_3$ | CH$_3$ | |
| 1 | Q-19 | — | H | H | Cl | OCH$_3$ | |
| 1 | Q-15(R$_7$ = CH$_2$CH=CH$_2$) | — | H | H | OCH$_3$ | OCH$_3$ | |
| 1 | Q-15(R$_7$ = CF$_3$) | — | H | H | OCH$_3$ | OCH$_3$ | |
| 1 | Q-15(R$_7$ = CF$_2$CF$_2$CF$_3$) | — | H | H | OCH$_3$ | OCH$_3$ | |
| 1 | Q-21 | — | H | H | OCH$_3$ | OCH$_3$ | |
| 1 | Q-21 | — | H | H | CH$_3$ | OCH$_3$ | |
| 1 | Q-21 | — | H | H | CH$_3$ | CH$_3$ | |
| 1 | Q-21 | — | H | H | Cl | OCH$_3$ | |
| 1 | Q-22 | — | H | H | OCH$_3$ | OCH$_3$ | |
| 1 | Q-22 | — | H | H | CH$_3$ | OCH$_3$ | |
| 1 | Q-22 | — | H | H | CH$_3$ | CH$_3$ | |
| 1 | Q-22 | — | H | H | Cl | OCH$_3$ | |
| 1 | Q-23(R$_6'$, R$_6''$ = CH$_3$) | — | H | H | OCH$_3$ | OCH$_3$ | |
| 1 | Q-23(R$_6'$, R$_6''$ = CH$_3$) | — | H | H | CH$_3$ | OCH$_3$ | |
| 1 | Q-23(R$_6'$, R$_6''$ = CH$_3$) | — | H | H | CH$_3$ | CH$_3$ | |
| 1 | Q-23(R$_6'$, R$_6''$ = CH$_3$) | — | H | H | Cl | OCH$_3$ | |

TABLE 1-continued

General Formula 1

| J | Q | E | R | R₁ | X | Y | m.p. °C. |
|---|---|---|---|---|---|---|---|
| 1 | Q-23(R₆' = H) | — | H | H | OCH₃ | OCH₃ | |
| 1 | Q-23(R₆' = H) | — | H | H | CH₃ | OCH₃ | |
| 1 | Q-23(R₆' = H) | — | H | H | CH₃ | CH₃ | |
| 1 | Q-23(R₆' = H) | — | H | H | Cl | OCH₃ | |
| 1 | Q-1(R₅ = CH₃) | — | H | 5-CH₂CN | OCH₃ | OCH₃ | |
| 1 | Q-1(R₅ = CH₃) | — | H | 5-CH₂CN | OCH₃ | CH₃ | |
| 1 | Q-1(R₅ = CH₃) | — | H | 5-CH₂CN | Cl | OCH₃ | |
| 1 | Q-1(R₅ = CH₃) | — | H | 5-CH₂CN | CH₃ | CH₃ | |
| 1 | Q-1(R₅ = CH₃) | — | H | 5-CH₂OCH₃ | OCH₃ | OCH₃ | |
| 1 | Q-1(R₅ = CH₃) | — | H | 5-CH₂SCH₃ | OCH₃ | OCH₃ | |
| 1 | Q-17(R₆ = CH₃) | — | H | H | OCH₃ | OCH₃ | |
| 1 | Q-1(R₅ = C₂H₅) | — | H | 5-CH₂SCH₃ | OCH₃ | OCH₃ | |
| 1 | Q-1(R₅ = n-C₃H₇) | — | H | 5-CH₂SCH₃ | OCH₃ | OCH₃ | |
| 2a | Q-20 | — | H | H | OCH₃ | OCH₃ | |
| 2a | Q-20 | — | H | H | CH₃ | OCH₃ | |
| 2a | Q-20 | — | H | H | CH₃ | CH₃ | |
| 2a | Q-20 | — | H | H | Cl | OCH₃ | |
| 2b | Q-20 | — | H | H | OCH₃ | OCH₃ | |
| 2b | Q-20 | — | H | H | CH₃ | OCH₃ | |
| 2b | Q-20 | — | H | H | CH₃ | CH₃ | |
| 2b | Q-20 | — | H | H | Cl | OCH₃ | |
| 2c | Q-20 | — | H | H | OCH₃ | OCH₃ | |
| 3a | Q-20 | — | H | H | OCH₃ | OCH₃ | |
| 3b | Q-20 | — | H | H | OCH₃ | OCH₃ | |
| 3c | Q-20 | — | H | H | OCH₃ | OCH₃ | |
| 5 | Q-20 | — | H | H | OCH₃ | OCH₃ | |
| 1 | Q-10 | O | H | H | OCF₂H | OCH₃ | 164–166 |
| 1 | Q-17(R₆ = CH₃) | — | H | H | CH₃ | OCH₃ | |
| 5 | Q-24(R₆' = H) | — | H | H | OCH₃ | OCH₃ | 124–128 |
| 5 | Q-24(R₆' = H) | — | H | H | CH₃ | OCH₃ | 110–115 |
| 5 | Q-24(R₆' = H) | — | H | H | CH₃ | CH₃ | 95–100 |
| 5 | Q-24(R₆' = CH₃) | — | H | H | OCH₃ | OCH₃ | 220–230 |
| 5 | Q-24(R₆' = CH₃) | — | H | H | OCH₃ | CH₃ | 118–120 |
| 5 | Q-24(R₆' = CH₃) | — | H | H | CH₃ | CH₃ | >240 |
| 5 | Q-24(R₆' = CH₃) | — | H | H | Cl | OCH₃ | 236–240 |
| 2a | Q-1(R₅ = H) | — | H | H | CH₃ | CH₃ | 198–201 |
| 2a | Q-1(R₅ = H) | — | H | H | CH₃ | OCH₃ | 229–231 |
| 2a | Q-1(R₅ = H) | — | H | H | OCH₃ | OCH₃ | 215–220 |
| 2a | Q-1(R₅ = H) | — | H | H | Cl | OCH₃ | 212–215 |
| 1 | Q-1(R₅ = CH₂CH(Cl)CH₂Cl) | — | H | H | OCH₃ | OCH₃ | 75–79 |
| 1 | Q-1(R₅ = CH₂CH₂CH₂CH₃) | — | H | H | OCH₃ | CH₃ | 168–173 |
| 1 | Q-1(R₅ = CH₂CH₂CH₂CH₃) | — | H | H | CH₃ | CH₃ | 163–166 |
| 1 | Q-1(R₅ = CH₂CH₂CH₂CH₃) | — | H | H | Cl | OCH₃ | 162–170 |
| 1 | Q-1(R₅ = CH₂CO₂CH₃) | — | H | H | CH₃ | CH₃ | 186–191 |
| 1 | Q-1(R₅ = CH₂CO₂CH₃) | — | H | H | Cl | OCH₃ | 78–97 |
| 1 | Q-1(R₅ = CH₂CO₂CH₃) | — | H | H | CH₃ | OCH₃ | 168–171 |
| 1 | Q-1(R₅ = CH₂CH₂OCH₃) | — | H | H | CH₃ | OCH₃ | 166–170 |
| 1 | Q-1(R₅ = CH₂CH₂OCH₃) | — | H | H | CH₃ | CH₃ | 189–191 |
| 1 | Q-1(R₅ = CH₂CH₂OCH₃) | — | H | H | Cl | OCH₃ | 171–173 |
| 1 | Q-1(R₅ = CH₃) | — | H | 5-Cl | CH₃ | OCH₃ | 177–179 |
| 1 | Q-1(R₅ = CH₃) | — | H | 5-Cl | CH₃ | CH₃ | 196–199 |
| 1 | Q-1(R₅ = CH₃) | — | H | 5-Cl | Cl | OCH₃ | 198–204 |
| 1 | Q-1(R₅ = CH₂OCH₃) | — | H | H | OCF₂H | CH₃ | 160–165 |
| 1 | Q-1(R₅ = CH₃OCH₃) | — | H | H | OCF₂H | OCH₃ | 135–140 |
| 1 | Q-1(R₅ = CH₂OCH₃) | — | H | H | Cl | OCF₂H | 140–146 |
| 1 | Q-1(R₅ = CH₃) | — | H | H | OCF₂H | CH₃ | 166–170 |
| 1 | Q-1(R₅ = CH₃) | — | H | 6-CH₃ | OCH₃ | OCH₃ | |
| 1 | Q-1(R₅ = CH₃) | — | H | 6-CH₃ | CH₃ | OCH₃ | |
| 1 | Q-1(R₅ = CH₃) | — | H | 6-CH₃ | CH₃ | CH₃ | |
| 1 | Q-1(R₅ = CH₃) | — | H | 6-CH₃ | Cl | OCH₃ | |
| 1 | Q-1(R₅ = CH₃) | — | H | 6-Cl | OCH₃ | OCH₃ | |
| 1 | Q-1(R₅ = CH₃) | — | H | 6-Cl | CH₃ | OCH₃ | |
| 1 | Q-1(R₅ = CH₃) | — | H | 6-Cl | CH₃ | CH₃ | |
| 1 | Q-1(R₅ = CH₃) | — | H | 6-Cl | Cl | OCH₃ | |
| 1 | Q-1(R₅ = CH₃) | — | H | 5-SCH₃ | CH₃ | OCH₃ | |
| 1 | Q-1(R₅ = CH₃) | — | H | 5-SCH₃ | CH₃ | CH₃ | |
| 1 | Q-1(R₅ = CH₃) | — | H | 5-SCH₃ | Cl | OCH₃ | |
| 1 | Q-1(R₅ = CH₃) | — | H | 5-OCH₃ | CH₃ | OCH₃ | |
| 1 | Q-1(R₅ = CH₃) | — | H | 5-OCH₃ | CH₃ | CH₃ | |
| 1 | Q-1(R₅ = CH₃) | — | H | 5-OCH₃ | Cl | OCH₃ | |
| 1 | Q-1(R₅ = CH₃) | — | H | 5-OCH₂CF₃ | OCH₃ | OCH₃ | |
| 1 | Q-1(R₅ = CH₃) | — | H | 5-OCH₂CF₃ | OCH₃ | CH₃ | |
| 1 | Q-1(R₅ = CH₃) | — | H | 5-OCH₂CF₃ | CH₃ | CH₃ | |
| 1 | Q-1(R₅ = CH₃) | — | H | 5-OCH₂CF₃ | Cl | OCH₃ | |
| 1 | Q-1(R₅ = CH₃) | — | H | 5-CH₂N₃ | OCH₃ | OCH₃ | |
| 1 | Q-1(R₅ = CH₃) | — | H | 5-CH₂SO₂CH₃ | OCH₃ | OCH₃ | |
| 1 | Q-25(R₆ = CH₃) | — | H | H | OCH₃ | OCH₃ | |
| 1 | Q-26 | — | H | H | OCH₃ | OCH₃ | |
| 1 | Q-27(R₆ = CH₃) | — | H | H | OCH₃ | OCH₃ | |
| 2a | Q-28 | — | H | H | OCH₃ | OCH₃ | |

TABLE 1-continued

General Formula 1

| J | Q | E | R | R$_1$ | X | Y | m.p. °C. |
|---|---|---|---|---|---|---|---|
| 2a | Q-29 | — | H | H | OCH$_3$ | OCH$_3$ | |
| 2a | Q-30 | — | H | H | OCH$_3$ | OCH$_3$ | |
| 2b | Q-1(R$_5$ = CH$_2$CH=CH$_2$) | — | H | H | OCH$_3$ | OCH$_2$CH$_2$OCH$_3$ | |
| 2b | Q-1(R$_5$ = CH$_2$CH=CH$_2$) | — | H | H | OCH$_3$ | OCH$_3$ | |
| 2b | Q-1(R$_5$ = CH$_2$CH=CH$_2$) | — | H | H | CH$_3$ | OCH$_3$ | |
| 2b | Q-1(R$_5$ = CH$_2$CH=CH$_2$) | — | H | H | CH$_3$ | CH$_3$ | |
| 2b | Q-1(R$_5$ = CH$_2$CH=CH$_2$) | — | H | H | Cl | OCH$_3$ | |

TABLE 2

General Formula 2

| J | Q | E | R | R$_1$ | X | Y | m.p. °C. |
|---|---|---|---|---|---|---|---|
| 1 | Q-1 (R$_5$ = CH$_3$) | — | H | H | OCH$_3$ | OCH$_3$ | 206–209 |
| 1 | Q-1 (R$_5$ = CH$_3$) | — | H | H | CH$_3$ | OCH$_3$ | 198–200 |
| 1 | Q-1 (R$_5$ = CH$_3$) | — | H | H | OC$_2$H$_5$ | NHCH$_3$ | 181 dec. |
| 1 | Q-1 (R$_5$ = CH$_3$) | — | H | H | OCH$_3$ | cyclopropyl | 209–211 |
| 1 | Q-1 (R$_5$ = CH$_3$) | — | H | H | OCH$_2$CH$_2$F | CH$_3$ | |
| 1 | Q-1 (R$_5$ = CH$_3$) | — | H | H | OCH$_2$CH$_2$F | OCH$_3$ | |
| 1 | Q-1 (R$_5$ = CH$_3$) | — | H | H | OCH$_2$CF$_3$ | NHCH$_3$ | 196 dec. |
| 1 | Q-1 (R$_5$ = CH$_3$) | — | H | H | OCH$_2$CF$_3$ | OCH$_3$ | 192–194 |
| 1 | Q-1 (R$_5$ = CH$_3$) | — | H | H | CH$_3$ | OCH$_2$C≡CH | 124–150 |
| 1 | Q-1 (R$_5$ = C$_2$H$_5$) | — | H | H | OCH$_3$ | CH$_3$ | 185–187 |
| 1 | Q-1 (R$_5$ = C$_2$H$_5$) | — | H | H | OCH$_3$ | OCH$_3$ | 192–194 |
| 1 | Q-1 (R$_5$ = C$_2$H$_5$) | — | H | H | OC$_2$H$_5$ | NHCH$_3$ | |
| 1 | Q-1 (R$_5$ = n-C$_3$H$_7$) | — | H | H | OCH$_3$ | CH$_3$ | 173–175 |
| 1 | Q-1 (R$_5$ = n-C$_3$H$_7$) | — | H | H | OCH$_3$ | OCH$_3$ | 178–180 |
| 1 | Q-1 (R$_5$ = CH(CH$_3$)$_2$) | — | H | H | CH$_3$ | OCH$_3$ | 198–200 |
| 1 | Q-1 (R$_5$ = n-C$_4$H$_9$) | — | H | H | CH$_3$ | OCH$_3$ | 145–149 |
| 1 | Q-1 (R$_5$ = t-butyl) | — | H | H | OCH$_3$ | CH$_3$ | |
| 1 | Q-1 (R$_5$ = CH$_2$CH(CH$_3$)$_2$ | — | H | H | CH$_3$ | OCH$_3$ | |
| 1 | Q-1 (R$_5$ = CH$_2$CH=CH$_2$) | — | H | H | CH$_3$ | OCH$_3$ | 173–174 |
| 1 | Q-1 (R$_5$ = CH$_2$CH=CH$_2$) | — | H | H | OCH$_3$ | OCH$_3$ | 174–177 |
| 1 | Q-1 (R$_5$ = CH$_2$CH=CHCH$_3$) | — | H | H | CH$_3$ | OCH$_3$ | |
| 1 | Q-1 (R$_5$ = CH$_2$C≡CH) | — | H | H | CH$_3$ | OCH$_3$ | |
| 1 | Q-1 (R$_5$ = CH$_2$C≡CCH$_3$) | — | H | H | OCH$_3$ | CH$_3$ | |
| 1 | Q-1 (R$_5$ = CH$_2$CN) | — | H | H | OCH$_3$ | CH$_3$ | 176–179 |
| 1 | Q-1 (R$_5$ = CH$_2$CN) | — | H | H | OCH$_3$ | OCH$_3$ | 170–175 |
| 1 | Q-1 (R$_5$ = CH$_2$CN) | — | H | H | OC$_2$H$_5$ | NHCH$_3$ | |
| 1 | Q-1 (R$_5$ = CH$_2$CO$_2$CH$_3$) | — | H | H | OCH$_3$ | CH$_3$ | 88–106 |
| 1 | Q-1 (R$_5$ = CH$_2$CO$_2$C$_2$H$_5$) | — | H | H | CH$_3$ | OCH$_3$ | |
| 1 | Q-1 (R$_5$ = CH(CH$_3$)CO$_2$CH$_3$) | — | H | H | OCH$_3$ | OCH$_3$ | |
| 1 | Q-1 (R$_5$ = CH(CH$_3$)CO$_2$C$_2$H$_5$) | — | H | H | CH$_3$ | OCH$_3$ | |
| 1 | Q-1 (R$_5$ = CF$_2$H) | — | H | H | CH$_3$ | OCH$_3$ | |
| 1 | Q-1 (R$_5$ = CF$_2$H) | — | H | H | OCH$_3$ | OCH$_3$ | |
| 1 | Q-1 (R$_5$ = CF$_2$H) | — | H | H | OC$_2$H$_5$ | NHCH$_3$ | |
| 1 | Q-1 (R$_5$ = CF$_2$H) | — | H | H | OCH$_3$ | cyclopropyl | |
| 1 | Q-1 (R$_5$ = CF$_2$H) | — | H | H | OCH$_2$CF$_3$ | OCH$_3$ | |
| 1 | Q-1 (R$_5$ = CF$_2$H) | — | H | H | OCH$_2$CH$_2$F | CH$_3$ | |
| 1 | Q-1 (R$_5$ = CH$_2$CH$_2$F) | — | H | H | CH$_3$ | OCH$_3$ | |
| 1 | Q-1 (R$_5$ = CH$_2$CH$_2$Cl) | — | H | H | CH$_3$ | OCH$_3$ | |
| 1 | Q-1 (R$_5$ = CH$_2$CH$_2$CH$_2$F) | — | H | H | CH$_3$ | OCH$_3$ | |
| 1 | Q-1 (R$_5$ = CH$_2$CHF$_2$) | — | H | H | CH$_3$ | OCH$_3$ | |
| 1 | Q-1 (R$_5$ = CH$_2$CF$_3$) | — | H | H | CH$_3$ | OCH$_3$ | |
| 1 | Q-1 (R$_5$ = CH$_2$OCH$_3$) | — | H | H | OCH$_3$ | CH$_3$ | 180–182 |
| 1 | Q-1 (R$_5$ = CH$_2$OCH$_3$) | — | H | H | OCH$_3$ | OCH$_3$ | 173–178 |
| 1 | Q-1 (R$_5$ = CH$_2$OCH$_3$) | — | H | H | OC$_2$H$_5$ | NHCH$_3$ | |
| 1 | Q-1 (R$_5$ = CH$_2$OC$_2$H$_5$) | — | H | H | CH$_3$ | OCH$_3$ | |
| 1 | Q-1 (R$_5$ = CH$_2$CH$_2$OCH$_3$) | — | H | H | CH$_3$ | OCH$_3$ | 158–161 |
| 1 | Q-1 (R$_5$ = CH$_2$CH$_2$OC$_2$H$_5$) | — | H | H | CH$_3$ | OCH$_3$ | |
| 1 | Q-2 (R$_6$ = CH$_3$) | — | H | H | CH$_3$ | OCH$_3$ | |
| 1 | Q-2 (R$_6$ = C$_2$H$_5$) | — | H | H | CH$_3$ | OCH$_3$ | |
| 1 | Q-2 (R$_6$ = CH(CH$_3$)$_2$) | — | H | H | CH$_3$ | OCH$_3$ | |
| 1 | Q-3 (R$_6$ = CH$_3$) | — | H | H | CH$_3$ | OCH$_3$ | |
| 1 | Q-4 (R$_6$ = CH$_3$) | — | H | H | CH$_3$ | OCH$_3$ | |
| 1 | Q-5 (R$_6$ = CH$_3$) | — | H | H | CH$_3$ | OCH$_3$ | |
| 1 | Q-5 (R$_6$ = n-C$_3$H$_7$) | — | H | H | CH$_3$ | OCH$_3$ | |
| 1 | Q-6 (R$_6$ = CH$_3$) | — | H | H | CH$_3$ | OCH$_3$ | |
| 1 | Q-7 (R$_5$, R$_6$ = CH$_3$) | — | H | H | CH$_3$ | OCH$_3$ | |
| 1 | Q-7 (R$_5$, R$_6$ = CH$_3$) | — | H | H | OCH$_3$ | OCH$_3$ | |
| 1 | Q-7 (R$_5$, R$_6$ = CH$_3$) | — | H | H | OC$_2$H$_5$ | NHCH$_3$ | |
| 1 | Q-8 | — | H | H | CH$_3$ | OCH$_3$ | |
| 1 | Q-9 | — | H | H | CH$_3$ | OCH$_3$ | |
| 1 | Q-9 | — | H | H | OCH$_3$ | OCH$_3$ | |
| 1 | Q-9 | — | H | H | OC$_2$H$_5$ | NHCH$_3$ | |
| 1 | Q-9 | — | H | H | OCH$_3$CF$_3$ | OCH$_3$ | |
| 1 | Q-9 | — | H | H | OCH$_2$CH$_2$F | CH$_3$ | |
| 1 | Q-10 | — | H | H | CH$_3$ | OCH$_3$ | |
| 1 | Q-10 | — | H | H | OCH$_3$ | OCH$_3$ | |

TABLE 2-continued

General Formula 2

| J | Q | E | R | R₁ | X | Y | m.p. °C. |
|---|---|---|---|---|---|---|---|
| 1 | Q-10 | — | H | H | OC$_2$H$_5$ | NHCH$_3$ | |
| 1 | Q-10 | — | H | H | OCH$_2$CF$_3$ | OCH$_3$ | |
| 1 | Q-10 | — | H | H | OCH$_2$CH$_2$F | CH$_3$ | |
| 1 | Q-11 | — | H | H | CH$_3$ | OCH$_3$ | |
| 1 | Q-12 | — | H | H | CH$_3$ | OCH$_3$ | |
| 1 | Q-13 | — | H | H | CH$_3$ | OCH$_3$ | |
| 1 | Q-14 (R$_6$ = CH$_3$) | — | H | H | CH$_3$ | OCH$_3$ | |
| 1 | Q-15 (R$_7$ = CH$_3$) | — | H | H | CH$_3$ | OCH$_3$ | |
| 1 | Q-15 (R$_7$ = CH$_3$) | — | H | H | OCH$_3$ | OCH$_3$ | |
| 1 | Q-15 (R$_7$ = CH$_3$) | — | H | H | OC$_2$H$_5$ | NHCH$_3$ | |
| 1 | Q-15 (R$_7$ = CH$_3$) | — | H | H | OCH$_2$CF$_3$ | OCH$_3$ | |
| 1 | Q-15 (R$_7$ = CH$_3$) | — | H | H | OCH$_2$CH$_2$F | CH$_3$ | |
| 1 | Q-15 (R$_7$ = C$_2$H$_5$) | — | H | H | CH$_3$ | OCH$_3$ | |
| 1 | Q-15 (R$_7$ = C$_2$H$_5$) | — | H | H | OCH$_3$ | OCH$_3$ | |
| 1 | Q-15 (R$_7$ = C$_2$H$_5$) | — | H | H | OCH$_2$CF$_3$ | OCH$_3$ | |
| 1 | Q-15 (R$_7$ = C$_2$H$_5$) | — | H | H | OC$_2$H$_5$ | NHCH$_3$ | |
| 1 | Q-15 (R$_7$ = C$_2$H$_5$) | — | H | H | OCH$_2$CH$_2$F | CH$_3$ | |
| 1 | Q-15 (R$_7$ = n-C$_3$H$_7$) | — | H | H | CH$_3$ | OCH$_3$ | |
| 1 | Q-15 (R$_7$ = CH(CH$_3$)$_2$) | — | H | H | CH$_3$ | OCH$_3$ | |
| 1 | Q-15 (R$_7$ = n-C$_4$H$_9$) | — | H | H | CH$_3$ | OCH$_3$ | |
| 1 | Q-15 (R$_7$ = t-butyl) | — | H | H | CH$_3$ | OCH$_3$ | |
| 1 | Q-15 (R$_7$ = t-butyl) | — | H | H | OCH$_3$ | OCH$_3$ | |
| 1 | Q-15 (R$_7$ = t-butyl) | — | H | H | OC$_2$H$_5$ | NHCH$_3$ | |
| 1 | Q-15 (R$_7$ = t-butyl) | — | H | H | OCH$_2$CF$_3$ | NHCH$_3$ | |
| 1 | Q-15 (R$_7$ = t-butyl) | — | H | H | OCH$_2$CH$_2$F | CH$_3$ | |
| 1 | Q-16 (R$_7$ = CH$_3$) | — | H | H | CH$_3$ | OCH$_3$ | |
| 1 | Q-1 (R$_5$ = CH$_3$) | O | H | H | CH$_3$ | OCH$_3$ | 68–73 |
| 1 | Q-1 (R$_5$ = CH$_3$) | O | H | H | OCH$_3$ | OCH$_3$ | 160–164 |
| 1 | Q-1 (R$_5$ = CH$_3$) | O | H | H | OC$_2$H$_5$ | NHCH$_3$ | |
| 1 | Q-1 (R$_5$ = CH$_3$) | O | H | H | OCH$_2$CF$_3$ | OCH$_3$ | |
| 1 | Q-1 (R$_5$ = CH$_3$) | O | H | H | OCH$_2$CH$_2$Cl | CH$_3$ | |
| 1 | Q-1 (R$_5$ = C$_2$H$_5$) | O | H | H | CH$_3$ | OCH$_3$ | |
| 1 | Q-1 (R$_5$ = n-C$_3$H$_7$) | O | H | H | CH$_3$ | OCH$_3$ | |
| 1 | Q-1 (R$_5$ = CH(CH$_3$)$_2$) | O | H | H | CH$_3$ | OCH$_3$ | |
| 1 | Q-1 (R$_5$ = CF$_2$H) | O | H | H | CH$_3$ | OCH$_3$ | |
| 1 | Q-1 (R$_5$ = CF$_2$H) | O | H | H | OCH$_3$ | OCH$_3$ | |
| 1 | Q-1 (R$_5$ = CF$_2$H) | O | H | H | OC$_2$H$_5$ | NHCH$_3$ | |
| 1 | Q-1 (R$_5$ = CF$_2$H) | O | H | H | OCH$_2$CF$_3$ | OCH$_3$ | |
| 1 | Q-1 (R$_5$ = CF$_2$H) | O | H | H | CH$_2$CH$_2$F | CH$_3$ | |
| 1 | Q-1 (R$_5$ = CH$_2$CN) | O | H | H | CH$_3$ | OCH$_3$ | |
| 1 | Q-1 (R$_5$ = CH$_2$CH=CH$_2$) | O | H | H | CH$_3$ | OCH$_3$ | |
| 1 | Q-7 (R$_5$, R$_6$ = CH$_3$) | O | H | H | CH$_3$ | OCH$_3$ | |
| 1 | Q-9 | O | H | H | CH$_3$ | OCH$_3$ | |
| 1 | Q-10 | O | H | H | OCH$_3$ | CH$_3$ | 76–84 |
| 1 | Q-10 | O | H | H | OCH$_3$ | OCH$_3$ | |
| 1 | Q-10 | O | H | H | OC$_2$H$_5$ | NHCH$_3$ | |
| 1 | Q-10 | O | H | H | OCH$_2$CF$_3$ | OCH$_3$ | |
| 1 | Q-15 (R$_7$ = CH$_3$) | O | H | H | CH$_3$ | OCH$_3$ | |
| 1 | Q-1 (R$_5$ = CH$_3$) | CH$_2$ | H | H | CH$_3$ | OCH$_3$ | 108–114 |
| 1 | Q-7 (R$_5$, R$_6$ = CH$_3$) | CH$_2$ | H | H | CH$_3$ | OCH$_3$ | |
| 1 | Q-9 | CH$_2$ | H | H | CH$_3$ | OCH$_3$ | |
| 1 | Q-10 | CH$_2$ | H | H | CH$_3$ | OCH$_3$ | |
| 1 | Q-15 | CH$_2$ | H | H | CH$_3$ | OCH$_3$ | |
| 1 | Q-1 (R$_5$ = CH$_3$) | — | CH$_3$ | H | CH$_3$ | OCH$_3$ | |
| 1 | Q-1 (R$_5$ = CH$_3$) | — | H | 3-F | CH$_3$ | OCH$_3$ | |
| 1 | Q-1 (R$_5$ = CH$_3$) | — | H | 5-Cl | CH$_3$ | OCH$_3$ | 195–198 |
| 1 | Q-1 (R$_5$ = CH$_3$) | — | H | 6-Br | CH$_3$ | OCH$_3$ | |
| 1 | Q-1 (R$_5$ = CH$_3$) | — | H | 5-CH$_3$ | CH$_3$ | OCH$_3$ | |
| 1 | Q-1 (R$_5$ = CH$_3$) | — | H | 6-C$_2$H$_5$ | CH$_3$ | OCH$_3$ | |
| 1 | Q-1 (R$_5$ = CH$_3$) | — | H | 5-OCH$_3$ | CH$_3$ | OCH$_3$ | |
| 1 | Q-1 (R$_5$ = CH$_3$) | — | H | 3-OC$_2$H$_5$ | CH$_3$ | OCH$_3$ | |
| 1 | Q-1 (R$_5$ = CH$_3$) | — | H | 6-OCH(CH$_3$)$_2$ | CH$_3$ | OCH$_3$ | |
| 1 | Q-1 (R$_5$ = CH$_3$) | — | H | 5-SCH$_3$ | CH$_3$ | OCH$_3$ | |
| 1 | Q-1 (R$_5$ = CH$_3$) | — | H | 6-SC$_2$H$_5$ | CH$_3$ | OCH$_3$ | |
| 1 | Q-1 (R$_5$ = CH$_3$) | — | H | 3-SCH(CH$_3$)$_2$ | CH$_3$ | OCH$_3$ | |
| 1 | Q-1 (R$_5$ = CH$_3$) | — | H | 5-CH$_2$F | CH$_3$ | OCH$_3$ | |
| 1 | Q-1 (R$_5$ = CH$_3$) | — | H | 5-CH$_2$CH$_2$Br | CH$_3$ | OCH$_3$ | |
| 1 | Q-1 (R$_5$ = CH$_3$) | — | H | 6-OCF$_2$H | CH$_3$ | OCH$_3$ | |
| 1 | Q-1 (R$_5$ = CH$_3$) | — | H | 6-OCH$_2$CH$_2$Br | CH$_3$ | OCH$_3$ | |
| 1 | Q-1 (R$_5$ = CH$_3$) | — | H | 6-OCH(CH$_3$)CH$_2$Cl | CH$_3$ | OCH$_3$ | |
| 1 | Q-1 (R$_5$ = CH$_3$) | — | H | 5-SCH$_2$F | CH$_3$ | OCH$_3$ | |
| 1 | Q-1 (R$_5$ = CH$_3$) | — | H | 6-SCH$_2$CH$_2$Br | CH$_3$ | OCH$_3$ | |
| 1 | Q-1 (R$_5$ = CH$_3$) | — | H | 6-SCH(CH$_3$)CH$_2$Cl | CH$_3$ | OCH$_3$ | |
| 1 | Q-1 (R$_5$ = CH$_3$) | — | H | H | C$_2$H$_5$ | OCH$_3$ | |
| 1 | Q-1 (R$_5$ = CH$_3$) | — | H | H | CH$_2$F | OCH$_3$ | |
| 1 | Q-1 (R$_5$ = CH$_3$) | — | H | H | CF$_3$ | OCH$_3$ | |
| 1 | Q-1 (R$_5$ = CH$_3$) | — | H | H | OCH$_2$CHF$_2$ | CH$_3$ | |
| 1 | Q-1 (R$_5$ = CH$_3$) | — | H | H | CH$_2$Cl | OCH$_3$ | |
| 1 | Q-1 (R$_5$ = CH$_3$) | — | H | H | CH$_2$Br | OCH$_3$ | |
| 1 | Q-1 (R$_5$ = CH$_3$) | — | H | H | H | OCH$_3$ | |

TABLE 2-continued

General Formula 2

| J | Q | E | R | R$_1$ | X | Y | m.p. °C. |
|---|---|---|---|---|---|---|---|
| 1 | Q-1 (R$_5$ = CH$_3$) | — | H | H | OCH$_3$ | SCH$_3$ | |
| 1 | Q-1 (R$_5$ = CH$_3$) | — | H | H | OCH$_3$ | C≡CH | |
| 1 | Q-1 (R$_5$ = CH$_3$) | — | H | H | OCH$_3$ | N(CH$_3$)$_2$ | |
| 1 | Q-1 (R$_5$ = CH$_3$) | — | H | H | OCH$_3$ | C$_2$H$_5$ | |
| 1 | Q-1 (R$_5$ = CH$_3$) | — | H | H | OCH$_3$ | CH$_2$OCH$_3$ | |
| 1 | Q-1 (R$_5$ = CH$_3$) | — | H | H | OCH$_3$ | CH(OCH$_3$)$_2$ | |
| 2a | Q-1 (R$_5$ = CH$_3$) | — | H | H | CH$_3$ | OCH$_3$ | 188–190 |
| 2a | Q-1 (R$_5$ = CH$_3$) | — | H | H | OCH$_3$ | OCH$_3$ | 168–171 |
| 2a | Q-1 (R$_5$ = CH$_3$) | — | H | H | OC$_2$H$_5$ | NHCH$_3$ | |
| 2a | Q-1 (R$_5$ = CH$_3$) | — | H | H | OCH$_3$ | cyclopropyl | |
| 2a | Q-1 (R$_5$ = C$_2$H$_5$) | — | H | H | CH$_3$ | OCH$_3$ | |
| 2a | Q-1 (R$_5$ = n-C$_3$H$_7$) | — | H | H | CH$_3$ | OCH$_3$ | |
| 2a | Q-1 (R$_5$ = CH$_2$CN) | — | H | H | CH$_3$ | OCH$_3$ | 190–193 |
| 2a | Q-1 (R$_5$ = CH$_2$CH=CH$_2$) | — | H | H | CH$_3$ | OCH$_3$ | 181–183 |
| 2a | Q-1 (R$_5$ = CF$_2$H) | — | H | H | CH$_3$ | OCH$_3$ | |
| 2a | Q-1 (R$_5$ = CF$_2$H) | — | H | H | OCH$_3$ | OCH$_3$ | |
| 2a | Q-1 (R$_5$ = CF$_2$H) | — | H | H | OC$_2$H$_5$ | NHCH$_3$ | |
| 2a | Q-7 (R$_5$, R$_6$ = CH$_3$) | — | H | H | OCH$_3$ | CH$_3$ | |
| 2a | Q-15 (R$_7$ = CH$_3$) | — | H | H | CH$_3$ | OCH$_3$ | |
| 2a | Q-15 (R$_7$ = CH$_3$) | — | H | H | OCH$_3$ | OCH$_3$ | |
| 2a | Q-15 (R$_7$ = CH$_3$) | — | H | H | OC$_2$H$_5$ | NHCH$_3$ | |
| 2a | Q-15 (R$_7$ = CH$_3$) | — | H | H | OCH$_2$CF$_3$ | OCH$_3$ | |
| 2a | Q-15 (R$_7$ = CH$_3$) | — | H | H | OCH$_2$CH$_2$F | CH$_3$ | |
| 2b | Q-1 (R$_5$ = CH$_3$) | — | H | H | CH$_3$ | OCH$_3$· | |
| 2b | Q-7 (R$_5$, R$_6$ = CH$_3$) | — | H | H | CH$_3$ | OCH$_3$ | |
| 2c | Q-1 (R$_5$ = CH$_3$) | — | H | H | CH$_3$ | OCH$_3$ | |
| 3a | (R$_2$ = CH$_3$)Q-1 (R$_5$ = CH$_3$) | — | H | H | CH$_3$ | OCH$_3$ | |
| 3b | (R$_2$ = C$_2$H$_5$)Q-1 (R$_5$ = CH$_3$) | — | H | H | CH$_3$ | OCH$_3$ | |
| 3c | (R$_2$ = CH$_3$)Q-1 (R$_5$ = CH$_3$) | — | H | H | CH$_3$ | OCH$_3$ | |
| 3d | (R$_2$ = CH$_3$)Q-1 (R$_5$ = CH$_3$) | — | H | H | CH$_3$ | OCH$_3$ | |
| 3d | (R$_2$ = C$_3$H$_7$)Q-1 (R$_5$ = CH$_3$) | — | H | H | CH$_3$ | OCH$_3$ | |
| 3d | (R$_2$ = CH(CH$_3$)$_2$)Q-1 (R$_5$ = CH$_3$) | — | H | H | CH$_3$ | OCH$_3$ | |
| 4 | Q-1 (R$_5$ = CH$_3$) | — | H | H | CH$_3$ | OCH$_3$ | dec. 168 |
| 5 | Q-15 (R$_7$ = CH$_3$) | — | H | H | CH$_3$ | OCH$_3$ | |
| 1 | Q-18 (R$_6$ = CH$_3$) | — | H | H | CH$_3$ | OCH$_3$ | |
| 1 | Q-18 (R$_6$ = CH$_3$) | — | H | H | OCH$_3$ | OCH$_3$ | |
| 1 | Q-19 | — | H | H | CH$_3$ | OCH$_3$ | |
| 1 | Q-19 | — | H | H | OCH$_3$ | OCH$_3$ | |
| 1 | Q-15 (R$_7$ = H) | — | H | H | CH$_3$ | OCH$_3$ | |
| 1 | Q-1 (R$_5$ = H) | — | H | H | CH$_3$ | OCH$_3$ | |
| 2a | Q-20 | — | H | H | CH$_3$ | OCH$_3$ | |
| 2a | Q-20 | — | H | H | OCH$_3$ | OCH$_3$ | |
| 1 | Q-21 | — | H | H | OCH$_3$ | OCH$_3$ | |
| 1 | Q-22 | — | H | H | OCH$_3$ | CH$_3$ | |
| 1 | Q-23 (R$_6$', R$_6$'' = CH$_3$) | — | H | H | OCH$_3$ | CH$_3$ | |
| 1 | Q-1 (R$_5$ = CH$_3$) | — | H | 5-CH$_2$CN | CH$_3$ | OCH$_3$ | |
| 1 | Q-1 (R$_5$ = CH$_3$) | — | H | 5-CH$_2$OCH$_3$ | CH$_3$ | OCH$_3$ | |
| 1 | Q-1 (R$_5$ = CH$_3$) | — | H | 5-CH$_2$SCH$_3$ | CH$_3$ | OCH$_3$ | |
| 1 | Q-1 (R$_5$ = CH(CH$_3$)$_2$) | — | H | H | OCH$_3$ | OCH$_3$ | 190–193 |
| 1 | Q-17 (R$_6$ = CH$_3$) | — | H | H | CH$_3$ | OCH$_3$ | |
| 2a | Q-1 (R$_5$ = H) | — | H | H | CH$_3$ | OCH$_3$ | 134–136 |
| 2a | Q-1 (R$_5$ = H) | — | H | H | OCH$_3$ | OCH$_3$ | 137–138 |
| 2a | Q-1 (R$_5$ = CH$_2$CN) | — | H | H | OCH$_3$ | OCH$_3$ | 182–185 |
| 2a | Q-1 (R$_5$ = C(O)CH$_3$) | — | H | H | OCH$_3$ | CH$_3$ | 129–130 |
| 2a | Q-1 (R$_5$ = CH$_2$CH=CH$_2$) | — | H | H | OCH$_3$ | OCH$_3$ | 156–159 |
| 1 | Q-1 (R$_5$ = CH(CH$_3$)$_2$) | — | H | H | OCH$_3$ | OCH$_3$ | 190–193 |
| 1 | Q-1 (R$_5$ = CH$_2$CH$_2$CH$_2$CH$_3$) | — | H | H | OCH$_3$ | OCH$_3$ | 156–162 |
| 1 | Q-1 (R$_5$ = CH$_2$CO$_2$CH$_3$) | — | H | H | OCH$_3$ | OCH$_3$ | 163–173 |
| 1 | Q-1 (R$_5$ = CH$_3$) | — | H | H | CH$_3$ | CH$_3$ | 219–221 |
| 1 | Q-1 (R$_5$ = CH$_2$CH$_2$OCH$_3$) | — | H | H | OCH$_3$ | OCH$_3$ | 143–151 |
| 1 | Q-1 (R$_5$ = CH$_3$) | CH$_2$ | H | H | OCH$_3$ | OCH$_3$ | 169–173 |
| 1 | Q-1 (R$_5$ = CH$_3$) | — | H | 5-Cl | OCH$_3$ | OCH$_3$ | 198–200 |
| 4 | Q-1 (R$_5$ = CH$_3$) | — | H | H | OCH$_3$ | OCH$_3$ | dec. 162 |
| 5 | Q-24 (R$_6$' = CH$_3$) | — | H | H | OCH$_3$ | CH$_3$ | 230–240 |
| 1 | Q-1 (R$_5$ = CH$_3$) | — | H | 6-CH$_3$ | OCH$_3$ | CH$_3$ | |
| 1 | Q-1 (R$_5$ = CH$_3$) | — | H | 6-CH$_3$ | OCH$_3$ | OCH$_3$ | |
| 1 | Q-1 (R$_5$ = CH$_3$) | — | H | 6-Cl | OCH$_3$ | CH$_3$ | |
| 1 | Q-1 (R$_5$ = CH$_3$) | — | H | 6-Cl | OCH$_3$ | OCH$_3$ | |
| 1 | Q-1 (R$_5$ = CH$_3$) | — | H | 5-SCH$_3$ | OCH$_3$ | OCH$_3$ | |
| 1 | Q-1 (R$_5$ = CH$_3$) | — | H | 5-OCH$_3$ | OCH$_3$ | OCH$_3$ | |
| 1 | Q-1 (R$_5$ = CH$_3$) | — | H | 5-OCH$_2$CF$_3$ | CH$_3$ | OCH$_3$ | |
| 1 | Q-1 (R$_5$ = CH$_3$) | — | H | 5-OCH$_2$CF$_3$ | OCH$_3$ | OCH$_3$ | |
| 1 | Q-1 (R$_5$ = CH$_3$) | — | H | 5-OCH$_2$N$_3$ | OCH$_3$ | CH$_3$ | |
| 1 | Q-1 (R$_5$ = CH$_3$) | — | H | 5-CH$_2$SO$_2$CH$_3$ | OCH$_3$ | CH$_3$ | |
| 1 | Q-25 (R$_6$ = CH$_3$) | — | H | H | CH$_3$ | OCH$_3$ | |
| 1 | Q-26 (R$_6$ = CH$_3$) | — | H | H | CH$_3$ | OCH$_3$ | |
| 1 | Q-27 (R$_6$ = CH$_3$) | — | H | H | CH$_3$ | OCH$_3$ | |
| 2a | Q-28 | — | H | H | CH$_3$ | OCH$_3$ | |
| 2a | Q-29 | — | H | H | CH$_3$ | OCH$_3$ | |
| 2a | Q-30 | — | H | H | CH$_3$ | OCH$_3$ | |

TABLE 2-continued

| | | General Formula 2 | | | | | |
|---|---|---|---|---|---|---|---|
| J | Q | E | R | $R_1$ | X | Y | m.p. °C. |
| 2b | Q-1 ($R_5$ = $CH_3$) | — | H | H | $OCH_3$ | $OCH_3$ | |
| 2b | Q-1 ($R_5$ = $CH_2CH=CH_2$) | — | H | H | $CH_3$ | $OCH_3$ | |
| 2b | Q-1 ($R_5$ = $CH_2CH=CH_2$) | — | H | H | $OCH_3$ | $OCH_3$ | |

TABLE 3

| | | General Formula 3 | | | | | |
|---|---|---|---|---|---|---|---|
| J | Q | E | $R_1$ | R | $X_1$ | $Y_1$ | m.p. °C. |
| 1 | Q-1 ($R_5$ = $CH_3$) | — | H | H | $CH_3$ | O | 222–224 |
| 1 | Q-1 ($R_5$ = $CH_3$) | — | H | H | $OCH_3$ | O | |
| 1 | Q-1 ($R_5$ = $CH_3$) | — | H | H | $OC_2H_5$ | O | |
| 1 | Q-1 ($R_5$ = $CH_3$) | — | H | H | $OCF_2H$ | O | |
| 1 | Q-1 ($R_5$ = $CH_3$) | — | H | H | $OCH_3$ | $CH_2$ | |
| 1 | Q-7 ($R_5$, $R_6$ = $CH_3$) | — | H | H | $CH_3$ | O | |
| 1 | Q-9 | — | H | H | $CH_3$ | O | |
| 1 | Q-10 | — | H | H | $CH_3$ | O | |
| 1 | Q-15 ($R_7$ = $CH_3$) | — | H | H | $CH_3$ | O | |
| 1 | Q-1 ($R_5$ = $CH_3$) | O | H | H | $CH_3$ | O | |
| 1 | Q-1 ($R_5$ = $CH_3$) | $CH_2$ | H | H | $CH_3$ | O | |
| 1 | Q-1 ($R_5$ = $CH_3$) | — | 5-Cl | H | $CH_3$ | O | |
| 1 | Q-1 ($R_5$ = $CH_3$) | — | 5-$CH_3$ | H | $CH_3$ | O | |
| 1 | Q-1 ($R_5$ = $CH_3$) | — | 5-$OCH_3$ | H | $CH_3$ | O | |
| 2a | Q-1 ($R_5$ = $CH_3$) | — | H | H | $CH_3$ | O | |
| 2b | Q-1 ($R_5$ = $CH_3$) | — | H | H | $CH_3$ | O | |
| 3a | Q-1 ($R_5$ = $CH_3$) | — | H | H | $CH_3$ | O | |
| 3c | Q-1 ($R_5$ = $CH_3$) | — | H | H | $CH_3$ | O | |
| 3d | Q-1 ($R_5$ = $CH_3$) | — | H | H | $CH_3$ | O | |
| 5 | Q-15 ($R_7$ = $CH_3$) | — | H | H | $CH_3$ | O | |
| 1 | Q-1 ($R_5$ = $CH_3$) | — | H | $CH_3$ | $OCH_3$ | O | |
| 1 | Q-18 ($R_6$ = $CH_3$) | — | H | H | $CH_3$ | O | |
| 1 | Q-23 ($R_6'$, $R_6''$ = $CH_3$) | — | H | H | $CH_3$ | O | |

TABLE 4

| | | General Formula 4 | | | | |
|---|---|---|---|---|---|---|
| J | Q | E | R | $R_1$ | $X_1$ | m.p. °C. |
| 1 | Q-1 ($R_5$ = $CH_3$) | — | H | H | $CH_3$ | |
| 1 | Q-1 ($R_5$ = $CH_3$) | — | H | H | $OCH_3$ | |
| 1 | Q-1 ($R_5$ = $CH_3$) | — | H | H | $OC_2H_5$ | |
| 1 | Q-1 ($R_5$ = $CH_3$) | — | H | H | $OCF_2H$ | |
| 1 | Q-7 ($R_5$, $R_6$ = $CH_3$) | — | H | H | $CH_3$ | |
| 1 | Q-9 | — | H | H | $CH_3$ | |
| 1 | Q-10 | — | H | H | $CH_3$ | |
| 1 | Q-15 ($R_7$ = $CH_3$) | — | H | H | $CH_3$ | |
| 1 | Q-1 ($R_5$ = $CH_3$) | O | H | H | $OCH_3$ | |
| 1 | Q-1 ($R_5$ = $CH_3$) | O | H | H | $CH_3$ | |
| 1 | Q-1 ($R_5$ = $CH_3$) | $CH_2$ | H | H | $CH_3$ | |
| 1 | Q-1 ($R_5$ = $CH_3$) | — | H | 5-Cl | $OCH_3$ | |
| 1 | Q-1 ($R_5$ = $CH_3$) | — | H | 5-$CH_3$ | $OCH_3$ | |
| 1 | Q-1 ($R_5$ = $CH_3$) | — | H | 5-$OCH_3$ | $OCH_3$ | |
| 2a | Q-1 ($R_5$ = $CH_3$) | — | H | H | $CH_3$ | |
| 2b | Q-1 ($R_5$ = $CH_3$) | — | H | H | $CH_3$ | |
| 3a | Q-1 ($R_5$ = $CH_3$) | — | H | H | $CH_3$ | |
| 3c | Q-1 ($R_5$ = $CH_3$) | — | H | H | $CH_3$ | |
| 3d | Q-1 ($R_5$ = $CH_3$) | — | H | H | $CH_3$ | |
| 5 | Q-15 ($R_7$ = $CH_3$) | — | H | H | $CH_3$ | |
| 1 | Q-1 ($R_5$ = $CH_3$) | — | $CH_3$ | H | $OCH_3$ | |
| 1 | Q-18 ($R_6$ = $CH_3$) | — | H | H | $CH_3$ | |
| 1 | Q-23 ($R_6'$, $R_6''$ = $CH_3$) | — | H | H | $CH_3$ | |

TABLE 5

| | | General Formula 5 | | | | | |
|---|---|---|---|---|---|---|---|
| J | Q | E | R | $R_1$ | $X_1$ | $Y_3$ | m.p. °C. |
| 1 | Q-1($R_5$ = $CH_3$) | — | H | H | $CH_3$ | $CH_3$ | |
| 1 | Q-1($R_5$ = $CH_3$) | — | H | H | $OCH_3$ | $CH_3$ | |
| 1 | Q-1($R_5$ = $CH_3$) | — | H | H | $OC_2H_5$ | $CH_3$ | |
| 1 | Q-1($R_5$ = $CH_3$) | — | H | H | $OCF_2H$ | $CH_3$ | |
| 1 | Q-1($R_5$ = $CH_3$) | — | H | H | $OCH_3$ | H | |
| 1 | Q-1($R_5$ = $CH_3$) | — | H | H | $CH_3$ | H | |
| 1 | Q-7($R_5$, $R_6$ = $CH_3$) | — | H | H | $OCH_3$ | $CH_3$ | |
| 1 | Q-9 | — | H | H | $OCH_3$ | $CH_3$ | |
| 1 | Q-10 | — | H | H | $OCH_3$ | $CH_3$ | |
| 1 | Q-15($R_7$ = $CH_3$) | — | H | H | $OCH_3$ | $CH_3$ | |

TABLE 5-continued

General Formula 5

| J | Q | E | R | R₁ | X₁ | Y₃ | m.p. °C. |
|---|---|---|---|---|---|---|---|
| 1 | Q-1(R₅ = CH₃) | O | H | H | OCH₃ | H | |
| 1 | Q-1(R₅ = CH₃) | CH₂ | H | H | OCH₃ | H | |
| 1 | Q-1(R₅ = CH₃) | — | 5-Cl | H | OCH₃ | H | |
| 1 | Q-1(R₅ = CH₃) | — | 5-CH₃ | H | OCH₃ | H | |
| 1 | Q-1(R₅ = CH₃) | — | 5-OCH₃ | H | OCH₃ | H | |
| 2a | Q-1(R₅ = CH₃) | — | H | H | CH₃ | H | |
| 2b | Q-1(R₅ = CH₃) | — | H | H | OCH₃ | H | |
| 3a | Q-1(R₅ = CH₃) | — | H | H | CH₃ | H | |
| 3c | Q-1(R₅ = CH₃) | — | H | H | CH₃ | H | |
| 3d | Q-1(R₅ = CH₃) | — | H | H | CH₃ | H | |
| 5 | Q-15(R₇ = CH₃) | — | H | H | OCH₃ | H | |
| 1 | Q-1(R₅ = CH₃) | — | CH₃ | H | OCH₃ | H | |
| 1 | Q-18(R₆ = CH₃) | — | H | H | CH₃ | H | |
| 1 | Q-23(R₆', R₆'' = CH₃) | — | H | H | CH₃ | H | |

TABLE 6

General Formula 6

| J | Q | E | R | R₁ | X₂ | Y₂ | m.p. °C. |
|---|---|---|---|---|---|---|---|
| 1 | Q-1(R₅ = CH₃) | — | H | H | CH₃ | OCH₃ | |
| 1 | Q-1(R₅ = CH₃) | — | H | H | CH₃ | OC₂H₅ | |
| 1 | Q-1(R₅ = CH₃) | — | H | H | CH₃ | SCH₃ | |
| 1 | Q-1(R₅ = CH₃) | — | H | H | CH₃ | SC₂H₅ | |
| 1 | Q-1(R₅ = CH₃) | — | H | H | CH₃ | CH₃ | |
| 1 | Q-1(R₅ = CH₃) | — | H | H | CH₃ | CH₂CH₃ | |
| 1 | Q-1(R₅ = CH₃) | — | H | H | C₂H₅ | OCH₃ | |
| 1 | Q-1(R₅ = CH₃) | — | H | H | CH₂CF₃ | OCH₃ | |
| 1 | Q-7(R₅, R₆ = CH₃) | — | H | H | CH₃ | OCH₃ | |
| 1 | Q-9 | — | H | H | CH₃ | OCH₃ | |
| 1 | Q-10 | — | H | H | CH₃ | OCH₃ | |
| 1 | Q-15(R₇ = CH₃) | — | H | H | CH₃ | SCH₃ | |
| 1 | Q-1(R₅ = CH₃) | O | H | H | CH₃ | OCH₃ | |
| 1 | Q-1(R₅ = CH₃) | CH₂ | H | H | CH₃ | OCH₃ | |
| 1 | Q-1(R₅ = CH₃) | — | H | 5-Cl | CH₃ | OCH₃ | |
| 1 | Q-1(R₅ = CH₃) | — | H | 5CH₃ | CH₃ | OCH₃ | |
| 1 | Q-1(R₅ = CH₃) | — | H | 5-OCH₃ | CH₃ | OCH₃ | |
| 2a | Q-1(R₅ = CH₃) | — | H | H | CH₃ | OCH₃ | |
| 2b | Q-1(R₅ = CH₃) | — | H | H | CH₃ | OCH₃ | |
| 3a | Q-1(R₅ = CH₃) | — | H | H | CH₃ | SCH₃ | |
| 3c | Q-1(R₅ = CH₃) | — | H | H | CH₃ | OCH₃ | |
| 3d | Q-1(R₅ = CH₃) | — | H | H | CH₃ | OCH₃ | |
| 5 | Q-15(R₇ = CH₃) | — | H | H | CH₃ | OCH₃ | |
| 1 | Q-1(R₅ = CH₃) | — | CH₃ | H | CH₃ | OCH₃ | |
| 1 | Q-18(R₆ = CH₃) | — | H | H | CH₃ | OCH₃ | |
| 1 | Q-23(R₆', R₆'' = CH₃) | — | H | H | CH₃ | OCH₃ | |

TABLE 7

General Formula 7

| J | Q | E | R | R₁ | X₃ | m.p. °C. |
|---|---|---|---|---|---|---|
| 1 | Q-1(R₅ = CH₃) | — | H | H | CH₃ | |
| 1 | Q-1(R₅ = CH₃) | — | H | H | OCH₃ | |
| 1 | Q-7(R₅, R₆ = CH₃) | — | H | H | CH₃ | |
| 1 | Q-9 | — | H | H | CH₃ | |
| 1 | Q-10 | — | H | H | OCH₃ | |
| 1 | Q-15(R₇ = CH₃) | — | H | H | OCH₃ | |
| 1 | Q-1(R₅ = CH₃) | O | H | H | CH₃ | |
| 1 | Q-1(R₅ = CH₃) | CH₂ | H | H | CH₃ | |
| 1 | Q-1(R₅ = CH₃) | — | H | 5-Cl | CH₃ | |
| 1 | Q-1(R₅ = CH₃) | — | H | 5-CH₃ | CH₃ | |
| 1 | Q-1(R₅ = CH₃) | — | H | 5-OCH₃ | CH₃ | |
| 2a | Q-1(R₅ = CH₃) | — | H | H | OCH₃ | |
| 2b | Q-1(R₅ = CH₃) | — | H | H | CH₃ | |
| 3a | Q-1(R₅ = CH₃) | — | H | H | CH₃ | |
| 3c | Q-1(R₅ = CH₃) | — | H | H | OCH₃ | |
| 3d | Q-1(R₅ = CH₃) | — | H | H | OCH₃ | |
| 5 | Q-15(R₇ = CH₃) | — | H | H | OCH₃ | |
| 1 | Q-1(R₅ = CH₃) | — | CH₃ | H | OCH₃ | |

TABLE 8

General Formula 8

| J | Q | E | R | R₁ | X₄ | Y₄ | Z₁ | m.p. (°C.) |
|---|---|---|---|---|---|---|---|---|
| 1 | Q-1(R₅ = CH₃) | — | H | H | CH₃ | CH₃ | CH | 144–155 |
| 1 | Q-1(R₅ = CH₃) | — | H | H | CH₃ | CH₃ | N | |
| 1 | Q-1(R₅ = CH₃) | — | H | H | OCH₃ | CH₃ | CH | |
| 1 | Q-1(R₅ = CH₃) | — | H | H | OCH₃ | CH₃ | N | |
| 1 | Q-1(R₅ = CH₃) | — | H | H | OCH₃ | OCH₃ | CH | |
| 1 | Q-1(R₅ = CH₃) | — | H | H | OCH₃ | OCH₃ | N | |
| 1 | Q-1(R₅ = CH₃) | — | H | H | Cl | CH₃ | CH | |
| 1 | Q-1(R₅ = CH₃) | — | H | H | OCH₃ | Cl | CH | |
| 1 | Q-1(R₅ = CH₃) | — | H | H | OC₂H₅ | CH₃ | CH | |

TABLE 8-continued

General Formula 8

| J | Q | E | R | $R_1$ | $X_4$ | $Y_4$ | $Z_1$ | m.p. (°C.) |
|---|---|---|---|---|---|---|---|---|
| 1 | Q-1($R_5$ = $CH_3$) | — | H | H | $CH_2OCH_3$ | $CH_3$ | N | |
| 1 | Q-1($R_5$ = $CH_3$) | — | H | H | $CH_2OCH_3$ | $OCH_3$ | CH | |
| 1 | Q-1($R_5$ = $CH_3$) | — | H | H | $OC_2H_5$ | $OC_2H_5$ | N | |
| 1 | Q-1($R_5$ = $CH_3$) | O | H | H | $CH_3$ | $CH_3$ | CH | |
| 1 | Q-7($R_5$, $R_6$ = $CH_3$) | $CH_2$ | H | H | $CH_3$ | $CH_3$ | CH | |
| 1 | Q-9 | — | H | H | $CH_3$ | $CH_3$ | CH | |
| 1 | Q-9 | — | H | H | $OCH_3$ | $OCH_3$ | N | |
| 1 | Q-10 | — | H | H | $CH_3$ | $CH_3$ | CH | |
| 1 | Q-1($R_5$ = $C_2H_5$) | — | H | H | $CH_3$ | $CH_3$ | CH | |
| 1 | Q-1($R_5$ = n-$C_3H_7$) | — | H | H | $CH_3$ | $CH_3$ | CH | |
| 2a | Q-1($R_5$ = $CH_3$) | — | H | H | $CH_3$ | $CH_3$ | CH | |
| 2b | Q-1($R_5$ = $CH_3$) | — | H | H | $CH_3$ | $CH_3$ | CH | |
| 3a | Q-1($R_5$ = $CH_3$) | — | H | H | $CH_3$ | $CH_3$ | CH | |
| 3c | Q-1($R_5$ = $CH_3$) | — | H | H | $CH_3$ | $CH_3$ | CH | |
| 3d | Q-1($R_5$ = $CH_3$) | — | H | H | $CH_3$ | $CH_3$ | CH | |
| 1 | Q-18($R_6$ = $CH_3$) | — | H | H | $CH_3$ | $CH_3$ | CH | |
| 1 | Q-23($R_6'$, $R_6''$ = $CH_3$) | — | H | H | $CH_3$ | $CH_3$ | CH | |
| 2a | Q-20 | — | H | H | $CH_3$ | $CH_3$ | CH | |

TABLE 9

General Formula 9

| J | Q | E | R | $R_1$ | W | X | Y | Z | m.p. (°C.) |
|---|---|---|---|---|---|---|---|---|---|
| 1 | Q-1($R_5$ = $CH_3$) | — | H | H | O | $OCH_3$ | $OCH_3$ | $CCH_3$ | |
| 1 | Q-1($R_5$ = $C_2H_5$) | — | H | H | O | $OCH_3$ | $OCH_3$ | $CCH_3$ | |
| 1 | Q-1($R_5$ = n-$C_3H_7$) | — | H | H | O | $OCH_3$ | $OCH_3$ | $CCH_3$ | |
| 1 | Q-1($R_5$ = $CH_3$) | — | H | H | O | $OCH_3$ | $OCH_3$ | $CC_2H_5$ | |
| 1 | Q-1($R_5$ = $CH_3$) | — | H | H | O | $OCH_3$ | $OCH_3$ | CCl | |
| 1 | Q-1($R_5$ = $CH_3$) | — | H | H | O | $OCH_3$ | $OCH_3$ | CBr | |
| 1 | Q-9 | — | H | H | O | $OCH_3$ | $OCH_3$ | $CCH_3$ | |
| 2a | Q-1($R_5$ = $CH_3$) | — | H | H | O | $OCH_3$ | $OCH_3$ | $CCH_3$ | |
| 2b | Q-1($R_5$ = $CH_3$) | — | H | H | O | $OCH_3$ | $OCH_3$ | $CCH_3$ | |
| 3c | Q-1($R_5$ = $CH_3$) | — | H | H | O | $OCH_3$ | $OCH_3$ | $CCH_3$ | |
| 3d | Q-1($R_5$ = $CH_3$) | — | H | H | O | $OCH_3$ | $OCH_3$ | $CCH_3$ | |
| 1 | Q-1($R_5$ = $CH_3$) | — | H | H | S | $OCH_3$ | $OCH_3$ | CH | |
| 1 | Q-1($R_5$ = $CH_3$) | — | H | H | S | $OCH_3$ | $CH_3$ | N | |
| 1 | Q-1($R_5$ = $C_2H_5$) | — | H | H | S | $OCH_3$ | $OCH_3$ | CH | |
| 1 | Q-1($R_5$ = n-$C_3H_7$) | — | H | H | S | $OCH_3$ | $OCH_3$ | CH | |
| 1 | Q-9 | — | H | H | S | $OCH_3$ | $CH_3$ | N | |
| 1 | Q-9 | — | H | H | S | $OCH_3$ | $CH_3$ | CH | |
| 1 | Q-7($R_5$, $R_6$ = $CH_3$) | — | H | H | S | $OCH_3$ | $OCH_3$ | CH | |
| 1 | Q-10 | — | H | H | S | $OCH_3$ | $OCH_3$ | CH | |
| 2a | Q-1($R_5$ = $CH_3$) | — | H | H | S | $OCH_3$ | $OCH_3$ | CH | |
| 2b | Q-1($R_5$ = $CH_3$) | — | H | H | S | $OCH_3$ | $OCH_3$ | CH | |
| 2c | Q-1($R_5$ = $CH_3$) | — | H | H | S | $OCH_3$ | $OCH_3$ | CH | |
| 3d | Q-1($R_5$ = $CH_3$) | — | H | H | S | $OCH_3$ | $OCH_3$ | CH | |
| 1 | Q-18($R_6$ = $CH_3$) | — | H | H | S | $OCH_3$ | $OCH_3$ | CH | |
| 1 | Q-20 | — | H | H | S | $OCH_3$ | $OCH_3$ | CH | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 10

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, (including Emulsifiable Concentrates) | 5–50 | 40–95 | 0–15 |
| Aqueous Suspension | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 14

Aqueous Suspension

| | |
|---|---|
| 2-(4,5-dihydro-4-methyl-5-oxo-1,3,4-oxadiazol-2-yl)-N—[(4-methoxy-6-methyl-1,3,5-triazin-2-yl)-aminocarbonyl]benzenesulfonamide | 25% |
| hydrated attapulgite | 3% |
| crude calcium ligninsulfonate | 10% |
| sodium dihydrogen phospate | 0.5% |
| water | 61.5% |

The ingredients are ground together in a ball or roller mill until the solid particles have been reduced to diameters under 10 microns.

EXAMPLE 15

Wettable Powder

| | |
|---|---|
| 2-(4,5-dihydro-4-methyl-5-oxo-1,3,4-oxadiazol- | 80% |
| 2-yl)-N—[(4,6-dimethoxypyrimidin-2-yl)amino-carbonyl]benzenesulfonamide | |
| sodium alkylnaphthalenesulfonate | 2% |
| sodium ligninsulfonate | 2% |
| synthetic amorphous silica | 3% |
| kaolinite | 13% |

The ingredients are blended and then ground in a hammermill to produce particles with an average particle size less than 25 microns in diameter. The material is reblended and sifted through a U.S.S. No. 50 sieve (0.3 mm opening) before being packaged.

EXAMPLE 16

Extruded Pellet

| | |
|---|---|
| 2-(4,5-dihydro-4-methyl-5-oxo-1,3,4-oxadiazol-2-yl)-N—[(4-methoxy-6-methyl-1,3,5-triazin-2-yl)-aminocarbonyl]benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 17

High Strength Concentrate

| | |
|---|---|
| 2-(4,5-dihydro-4-methyl-5-oxo-1,3,4-oxadiazol-2-yl)-N—[(4,6-dimethoxypyrimidin-2-yl)amino-carbonyl]benzenesulfonamide | 98.5% |
| silica aerogel | 0.5% |
| synthetic amorphous silica | 1.0% |

The ingredients are blended and ground in a hammer-mill to produce a material essentially all passing a U.S.S. No. 50 screen (0.3 mm opening). The concentrate may then be formulated in a variety of ways.

EXAMPLE 18

Wettable Powder

| | |
|---|---|
| 2-(4,5-dihydro-4-methyl-5-oxo-1,3,4-oxadiazol-2-yl)-N—[(4,6-dimethoxypyrimidin-2-yl)amino-carbonyl]benzenesulfonamide | 65% |
| dodecylphenol polyethylene | 4% |
| glycol ether | 4% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammer-mill to produce particles essentially all below 100 microns, the material is reblended and sifted through a U.S.S. No. 50 sieve (0.3 mm opening) and packaged.

EXAMPLE 19

Wettable Powder

| | |
|---|---|
| 2-(4,5-dihydro-4-methyl-5-oxo-1,3,4-oxadiazol-2-yl)-N—[(4-methoxy-6-methyl-1,3,5-triazin-2-yl)-aminocarbonyl]benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 20

Wettable Powder

| | |
|---|---|
| 2-(4,5-dihydro-4-methyl-5-oxo-1,3,4-oxadiazol-2-yl)-N—[(4-methoxy-6-methyl-1,3,5-triazin-2-yl)-aminocarbonyl]benzenesulfonamide | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 21

Granule

| | |
|---|---|
| wettable powder of Example 20 | 15% |
| gypsum | 69% |
| potassium sulfate | 16% |

The ingredients are blended in a rotating mixer and water sprayed on to accomplish granulation. When most of the material has reached the desired range of 1.0 to 0.42 mm (U.S.S. #18 to 40 sieves), the granules are removed, dried and screened. Oversize material is crushed to produce additional material in the desired range. These granules contain 6% active ingredient.

EXAMPLE 22

Oil Suspension

| | |
|---|---|
| 2-(4,5-dihydro-4-methyl-5-oxo-1,3,4-oxadiazol-2-yl)-N—[(4,6-dimethoxypyrimidin-2-yl)aminocarbonyl]benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 23

Oil Suspension

| | |
|---|---|
| 2-(4,5-dihydro-4-methyl-5-oxo-1,3,4-oxadiazol-2-yl)-N—[(4,6-dimethoxypyrimidin-2-yl)aminocarbonyl]benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 3 microns. The product can be used directly, extended with oils, or emulsified in water.

Utility

Test results indicate that the compounds of the present invention are highly active pre-emergent or post-emergent herbicides or plant growth regulants. Many of them have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as wheat and barley. Alternatively, the subject compounds are useful to modify plant growth. The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.005 to 10 kg/ha, the lower rates being suggested for use on lighter soils and/or those having a low organic matter content, for plant growth modifications or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

Compounds

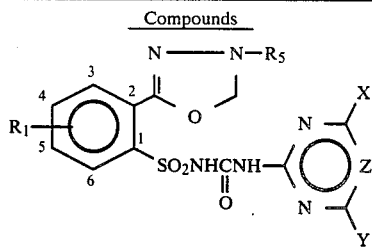

| Compound | R₁ | R₅ | X | Y | Z |
|---|---|---|---|---|---|
| 1 | H | CH₃ | OCH₃ | OCH₃ | CH |
| 2 | H | CH₃ | OCH₃ | CH₃ | CH |
| 3 | H | CH₃ | CH₃ | CH₃ | CH |
| 4 | H | CH₃ | Cl | OCH₃ | CH |
| 5 | H | CH₃ | OCH₃ | CH₃ | N |
| 6 | H | CH₃ | OCH₃ | OCH₃ | N |
| 7 | H | CH₃ | Cl | OCH₂CH₃ | CH |
| 8 | H | CH₃ | OC₂H₅ | NHCH₃ | CH |
| 9 | H | CH₃ | OCH₃ | CH₂SCH₃ | CH |
| 10 | H | CH₃ | OCH₃ | H | CH |
| 11 | H | CH₃ | CH₃ | H | CH |
| 12 | H | CH₃ | OCH₃ | CH₂OCH₂CH₃ | CH |
| 13 | H | CH₃ | OCF₂H | OCH₃ | CH |
| 14 | H | CH₃ | Br | OCH₃ | CH |
| 15 | H | CH₃ | OCH₃ | CH(OCH₃)₂ | CH |
| 16 | H | CH₃ | CH₃ | OC₂H₅ | CH |
| 17 | H | CH₃ | CH₃ | CH₂OCH₃ | CH |
| 18 | H | CH₃ | cyclopropyl | OCH₃ | N |
| 19 | H | C₂H₅ | OCH₃ | OCH₃ | CH |
| 20 | H | C₂H₅ | CH₃ | OCH₃ | CH |
| 21 | H | C₂H₅ | CH₃ | CH₃ | CH |
| 22 | H | C₂H₅ | Cl | OCH₃ | CH |
| 23 | H | C₂H₅ | CH₃ | OCH₃ | N |
| 24 | H | C₂H₅ | OCH₃ | OCH₃ | N |
| 25 | H | n-C₃H₇ | OCH₃ | OCH₃ | CH |
| 26 | H | n-C₃H₇ | CH₃ | OCH₃ | CH |
| 27 | H | n-C₃H₇ | CH₃ | OCH₃ | N |
| 28 | H | CH₂CH(Cl)CH₂Cl | OCH₃ | OCH₃ | CH |
| 29 | H | i-C₃H₇ | OCH₃ | OCH₃ | CH |
| 30 | H | i-C₃H₇ | CH₃ | OCH₃ | CH |
| 31 | H | i-C₃H₇ | CH₃ | CH₃ | CH |
| 32 | H | n-C₄H₉ | CH₃ | OCH₃ | CH |
| 33 | H | CH₂OCH₃ | OCH₃ | OCH₃ | CH |
| 34 | H | CH₂OCH₃ | CH₃ | OCH₃ | CH |
| 35 | H | CH₂OCH₃ | CH₃ | CH₃ | CH |
| 36 | H | CH₂OCH₃ | Cl | OCH₃ | CH |
| 37 | H | CH₂OCH₃ | CH₃ | OCH₃ | N |
| 38 | H | CH₂OCH₃ | OCH₃ | OCH₃ | N |
| 39 | H | CH₂CO₂CH₃ | OCH₃ | OCH₃ | CH |
| 40 | H | CH₂CH₂OCH₃ | OCH₃ | OCH₃ | CH |
| 41 | H | CH₂CH₂OCH₃ | CH₃ | OCH₃ | CH |
| 42 | H | CH₂CN | OCH₃ | OCH₃ | CH |
| 43 | H | CH₂CN | CH₃ | OCH₃ | CH |
| 44 | H | CH₂CH=CH₂ | OCH₃ | OCH₃ | CH |
| 45 | H | CH₂CH=CH₂ | CH₃ | OCH₃ | CH |
| 46 | H | CH₂CH=CH₂ | CH₃ | CH₃ | CH |
| 47 | H | CH₂CH=CH₂ | Cl | OCH₃ | CH |
| 48 | H | CH₂CH=CH₂ | CH₃ | OCH₃ | N |
| 49 | H | CH₂CH=CH₂ | OCH₃ | OCH₃ | N |
| 50 | 5-Cl | CH₃ | OCH₃ | OCH₃ | CH |
| 51 | 5-Cl | CH₃ | CH₃ | OCH₃ | CH |
| 52 | 5-Cl | CH₃ | CH₃ | CH₃ | CH |
| 53 | 5-Cl | CH₃ | Cl | OCH₃ | CH |
| 54 | 5-Cl | CH₃ | CH₃ | OCH₃ | N |
| 55 | 5-Cl | CH₃ | OCH₃ | OCH₃ | N |
| 56 | H | CH₃ | OC₂H₅ | NHCH₃ | N |
| 57 | H | CH₃ | OCH₂CF₃ | NHCH₃ | N |
| 58 | H | CH₂OCH₃ | OCF₂H | OCH₃ | CH |

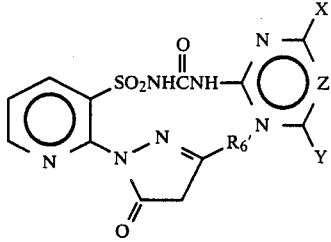

| Compound | $R_6'$ | X | Y | Z |
|---|---|---|---|---|
| 59 | H | $OCH_3$ | $OCH_3$ | CH |
| 60 | H | $CH_3$ | $OCH_3$ | CH |
| 61 | $CH_3$ | $OCH_3$ | $OCH_3$ | CH |

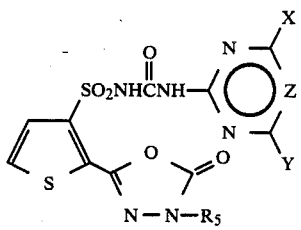

| Compound | $R_5$ | X | Y | Z |
|---|---|---|---|---|
| 62 | $CH_2CH=CH_2$ | $CH_3$ | $OCH_3$ | CH |
| 63 | $CH_2CH=CH_2$ | $OCH_3$ | $OCH_3$ | CH |
| 64 | $CH_2CN$ | $OCH_3$ | $OCH_3$ | CH |
| 65 | $CH_3$ | $CH_3$ | $CH_3$ | CH |
| 66 | $CH_3$ | $CH_3$ | $OCH_3$ | CH |
| 67 | $CH_3$ | $OCH_3$ | $OCH_3$ | CH |

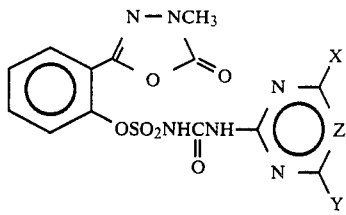

| Compound | X | Y | Z |
|---|---|---|---|
| 68 | $OCH_3$ | $OCH_3$ | CH |
| 69 | $CH_3$ | $OCH_3$ | CH |

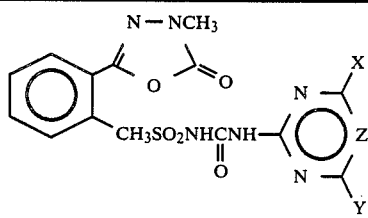

| Compound | X | Y | Z |
|---|---|---|---|
| 70 | $OCH_3$ | $OCH_3$ | CH |

Test A

Seeds of crabgrass (Digitaria sp.), barnyardgrass (Echinochloa crusqualli), wild oats (Avena fatua), cheatgrass (Bromus secalinus), velvetleaf (Abutilon theophrasti), morningglory (Ipomoea spp.), cocklebur (Xanthium pensylvanicum), sorghum, corn, soybean, sugarbeet, cotton, rice, wheat and purple nutsedge (Cyperus rotundus) tubers were planted and treated pre-emergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis or necrosis;
B=burn;
D=defoliation;
E=emergence inhibition;
G=growth retardation;
H=formative effects;
U=unusual pigmentation;
X=axillary stimulation;
S=albinism; and
6Y=abscised buds or flowers.

TABLE A

| | Cmpd. 1 | Cmpd. 2 | Cmpd. 3 | Cmpd. 4 | Cmpd. 5 | Cmpd. 6 | Cmpd. 7 | Cmpd. 8 | Cmpd. 9 | Cmpd. 10 | Cmpd. 11 | Compound 12 | | Cmpd. 13 | Cmpd. 14 | Cmpd. 15 |
|---|---|---|---|---|---|---|---|---|---|---|---|---|---|---|---|---|
| Rate kg/ha | 0.05 | 0.05 | 0.05 | 0.05 | 0.05 | 0.05 | 0.05 | 0.05 | 0.05 | 0.05 | 0.05 | 0.01 | 0.05 | 0.05 | 0.05 | 0.05 |
| | | | | | | | POST-EMERGENCE | | | | | | | | | |
| Morningglory | 10C | 10C | 10C | 9C | 10C | — | 3C,9G | 4G | 3C,8H | 4C,9G | 4C,9H | 5G | 2C,7H | 1C,7G | — | 3C,8H |
| Cocklebur | 10C | 10C | 10C | 10C | 4G | 5C,9G | 5C,9G | 2C,8G | 5C,9H | 4C,9G | 4C,8G | 8G | 5C,9H | 5C,9G | — | 5C,9H |
| Velvetleaf | 10C | 9C | 9C | 9C | 4C,8G | 9C | 3G | 2C,8G | 4C,9H | 5C,9H | — | 2G | 3C,6G | 4C,8H | 9C | 3C,7G |
| Nutsedge | 10C | 9C | 9C | 9G | 2G | 5C,9G | 2C,8G | 2C,8G | 2C,8G | 0 | 0 | 0 | 5G | 2C,8G | 9C | 3G |
| Crabgrass | 3C,8G | 3C,8G | 3C,8G | 5G | 0 | 4C,8G | 2G | 2C,5G | 3G | 0 | 2H | 0 | 3C,5G | 0 | 9C | 3G |
| Giant Foxtail | — | — | — | — | — | — | — | — | — | — | — | 8H | — | — | — | — |
| Barnyardgrass | 5C,9H | 3C,9H | 5C,9H | 3C,9H | 2H | — | 3C,7H | 4C,9H | 5C,9H | 7H | 4C,9H | 8H | 4C,9H | 7H | 4C,9H | 4C,9H |
| Cheatgrass | 6C,9G | 9C | 9C | 7G | 2G | 9H | 8G | 2C,8G | 2C,9G | 4G | 2C,9G | 4G | 2C,9G | 4G | 2C,9G | 2C,9G |
| Wild Oats | 3C,8G | 5C,9G | 3C,9G | 3C,8G | 0 | 5C,9G | 4G | 3G | 3G | 2C,7G | 3C,7H | 1C | 3C,7H | 0 | 9C | 3C,6G |
| Wheat | 3G | 3C,9G | 3C,9G | 2G | 0 | 4C,9G | 3G | 5G | 2G | 0 | 5G | 0 | 5G | 0 | — | 4G |
| Corn | 3C,9G | 3C,9G | 3C,9G | 3C,9H | 7H | 6C,9G | 5H | 3C,9G | 3C,9G | 2H | 9C | 2U,8G | 9C | 7H | — | 9C |
| Barley | — | — | — | — | — | — | — | — | — | — | — | — | — | — | — | — |
| Soybean | 9C | 9C | 9C | 6H | 5C,9G | 5C,9H | 5C,9G | 5C,9G | 5C,9G | 5C,9G | 4C,9G | 3C,8G | 9C | 2C,4G | 2C,9G | 4C,9G |
| Rice | 9C | 9C | 9C | 3C,9G | 4G | 9C | 2C,8G | 4C,9H | 5C,9G | 2G | 6C,9G | 4C,9G | 2C,8G | 3C,8G | 3C,8G | 6C,9G |
| Sorghum | 2C,9G | 4C,9G | 4C,9G | 9H | 2C,5G | 5C,5G | 3C,9H | 3C,9H | 5C,9G | 2G | 4C,9G | 3C,9H | 4C,9G | 4C,9G | 9C | 4C,9G |
| Sugar beet | 9C | 9C | 9C | 5C,9G | 9C | 9C | 3C,6H | 3C,8H | 5C,9G | 10C | 4C,7H | 3G | 9C | 4C,8G | 9C | 6C,9H |
| Cotton | 9C | 9C | 9C | 9C | 5C,9G | 5C,9G | 2C,8G | 3C,8G | 4C,9G | 4C,9G | 4C,8H | 5G | 9C | 5C,9G | 9C | 4C,9H |
| | | | | | | | PRE-EMERGENCE | | | | | | | | | |
| | Cmpd. 16 | Cmpd. 17 | Cmpd. 18 | Compound 19 | | Cmpd. 20 | Cmpd. 21 | Cmpd. 22 | Cmpd. 23 | Cmpd. 25 | Cmpd. 10 | Cmpd. 11 | | | | |
| | | | | 0.01 | 0.05 | | | | | | | | | | | |
| Morningglory | 9G | 9G | 9C | 4C,8G | 10C | 9G | 8G | 3G | 2C,2H | 3G | 3H | 2C | 7G | 8G | 3H | 3H |
| Cocklebur | 9H | 10E | 9H | 5C,9G | 10C | — | 9H | 9H | 5G | 4G | 4G | 2H | 3C | 3G | 4G | 4G |
| Velvetleaf | 9C | 9C | 9C | 3G | 10C | 2G | 3G | 9C | 3C,7G | 9G | 3C,3H | 2H | 0 | 0 | 5G | 0 |
| Nutsedge | 10E | 10E | 10E | 3G | 10C | 0 | 2C,5G | 9C | 3G | 5G | 0 | 0 | 0 | 2G | 5G | 0 |
| Crabgrass | 7G | 3C,7G | 3C,6G | 4G | 5G | 0 | 0 | 4G | 2G | — | 0 | 0 | 3G | 5G | — | 0 |
| Giant Foxtail | — | — | — | — | — | — | — | — | — | — | — | — | — | — | — | — |
| Barnyardgrass | 9H | 5C,9H | 3C,9H | 1C | — | 2C,2H | 5H | 4C,9H | 4C,9H | — | 4C,7H | 4C,9H | 4C,7H | 5G | 3C,7H | 3C,7H |
| Cheatgrass | 10H | 9H | 6H | 2G | — | 7G | 2C,8H | 4C,9H | 5C,9H | — | 2G | 7G | 7G | 4G | — | 7G |
| Wild Oats | 2C,7G | 5C,9G | 3C,8H | — | — | 2C | 3C,7G | 4C,9H | 7G | — | 2C,5G | 3C,7G | 3C,7G | 0 | 2C,5G | 2C,6G |
| Wheat | 6G | 5C,9H | 7G | 2C,8G | — | 3G | 5H | 5C,9H | 6G | — | 6G | 2C | 7G | 0 | 6G | 2C,6G |
| Corn | 2C,9G | 9G | 2C,8G | — | — | 2C,7G | 2C,9G | 3C,9H | 3C,8G | — | 0 | 7H | 3C,7G | 4G | 3C,8H | 3C,8H |
| Barley | — | — | — | — | — | — | — | — | — | — | — | — | — | — | — | — |
| Soybean | 9H | 9H | 4C,6H | 2C,5H | — | 3C,7G | 5H | 3C,3H | 2C,6H | — | 2C,2H | 3C,5H | — | 2G | — | 0 |
| Rice | 10E | 10E | 10E | 9H | — | 5G | 2C,8H | 5C,9H | 4C,8H | — | 0 | 0 | 4C,8H | 7H | — | 4C,8H |
| Sorghum | 10H | 10H | 5C,9H | 3C,8G | — | 2C,5G | 3C,5G | 4C,9H | — | — | 2G | 4C,8H | 3C,7H | 5G | — | 4C,9H |
| Sugar beet | 9C | 9C | 4C,9G | 5C,9G | — | 5C,9G | 3C,8G | 10E | 5C,9G | — | 4C,7G | 3C,7H | 4C,9G | 8G | — | 5H |
| Cotton | 9G | 9G | 9G | 8G | — | 2C,8H | 6G | 0 | — | — | 2G | 2H | — | 4G | — | 0 |
| | Cmpd. 16 | Cmpd. 17 | Cmpd. 18 | Compound 19 | | Cmpd. 20 | Cmpd. 21 | Cmpd. 22 | Cmpd. 23 | Cmpd. 24 | Cmpd. 25 | Cmpd. 26 | Cmpd. 27 | Cmpd. 28 | Cmpd. 29 | Cmpd. 30 |
| Rate kg/ha | 0.05 | 0.05 | 0.05 | 0.01 | 0.05 | 0.05 | 0.05 | 0.05 | 0.05 | 0.05 | 0.05 | 0.05 | 0.05 | 0.05 | 0.05 | 0.05 |
| | | | | | | | POSTEMERGENCE | | | | | | | | | |
| Morningglory | 10C | 4C,9G | 5C,9G | 4C,8G | 10C | 5C,9G | 10C | 10C | 10C | 10C | 9C | 9C | 9C | 2C,7G | 9C | 10C |
| Cocklebur | 9C | 6C,9G | 5C,9G | 5C,9G | 10C | 9C | 10C | 10C | 10C | 10C | 10C | 9C | 9C | 5C,9G | 9C | 9C |
| Velvetleaf | 9C | 9C | 4C,9G | 10C | 10C | 5C,9G | 10C | 9C | 10C | 5C,9G | 9C | 9C | 4C,9H | 4C,8H | 10C | 9C |
| Nutsedge | 9G | 4C,8G | 0 | 10C | 10C | 4C,9G | 3C,9G | 4G | 10C | 2C,5G | 2C,9G | 9G | 0 | 3G | 10C | 2C,8G |
| Crabgrass | 3C,7H | 4H | — | 3G | 4G | 2G | 0 | 0 | 10C | 2G | 2G | 3G | 2G | 2G | 3G | 0 |
| Giant Foxtail | — | — | — | 2C,7H | 5G | — | 4H | — | — | — | — | — | — | — | — | — |
| Barnyardgrass | 5C,9H | 4C,8H | 3C,9H | 2G | 5C,9H | 9H | 4H | — | 10C | 3H | 9H | 9H | 0 | 3C,8H | 4C,9H | 3C,9H |
| Cheatgrass | 3C,9G | 4C,9G | 3C,8H | 0 | 6C,9G | 5C,9G | 8G | 2G | 10C | 0 | 8G | 9G | 2H | 2C,5G | 2C,8G | 3C,9H |
| Wild Oats | 3C,7G | 3C,8G | 9G | — | — | 6C,9G | 7G | 0 | — | 5G | 5G | 3C,9G | 0 | 0 | 6G | 3C,9G |

TABLE A-continued

| | Cmpd. 31 | | Cmpd. 32 | | Cmpd. 33 | | Cmpd. 34 | | Cmpd. 35 | | Cmpd. 36 | | Cmpd. 37 | | Cmpd. 38 | | Cmpd. 39 | | Compound 40 | | Compound 41 | | Compound 42 | | Compound 43 | |
|---|---|---|---|---|---|---|---|---|---|---|---|---|---|---|---|---|---|---|---|---|---|---|---|---|---|---|
| Rate kg/ha | 0.05 | | | | 0.05 | | 0.05 | | 0.05 | | 0.05 | | 0.05 | | 0.05 | | 0.05 | | 0.05 | 0.01 | 0.05 | 0.01 | 0.05 | 0.01 | 0.05 | 0.01 |
| Wheat | 5G | 2C,7G | | | 0 | 5G | 4C,9G | 9G | 9G | 9C | 2G | 0 | 2C,5H | 0 | 7G | 0 | — | | | | | | | | | |
| Corn | 5C,9G | 5C,9G | | | 2C,4H | 9C | 5H | 10C | 4C,9G | 10C | 3U,9H | 2C,7G | 9C | 5C,9G | 4U,9C | 8H | 3C,9H | 7G | | | | | | | | |
| Barley | — | — | | | — | — | — | — | — | — | — | — | — | — | — | — | — | — | | | | | | | | |
| Soybean | 9C | 9C | | | 5C,9G | 9C | 4C,9G | 5C,9G | 5C,9G | 9C | 4C,9G | 9C | 9C | 9C | 6C,9G | 5C,9G | 4C,9G | 4C,9G | | | | | | | | |
| Rice | 9C | 9C | | | 0 | 5C,9G | 4G | 6C,9G | 6C,9G | 4C,9G | 5C,9G | 2G | 3G | 3G | 6C,9G | 0 | 4C,9G | 2C,6G | | | | | | | | |
| Sorghum | 5C,9H | 3U,9H | | | 2H | 4C,9H | 2G | 3U,9H | 3U,9H | 3C,9H | 3C,9H | 2C | 2G | 2G | 4C,9H | 9C | 1C,3H | 4G | | | | | | | | |
| Sugar beet | 9C | 9C | | | 5C,9G | 9C | 3G | 10C | 10C | 9C | 9C | 2C,3G | 9C | 9C | 3C,7G | 9C | 3C,5G | 9C | | | | | | | | |
| Cotton | 9C | 9C | | | 4C,9G | 9C | 0 | 9C | 9C | 5C,9G | 5C,9G | 5C,9G | 5C,9G | 9C | 2C,6G | 5C,9G | 4G | 5C,9G | | | | | | | | |
| | | | | | | | | | | | | | | | | | | | | | | | | | | |
| Morningglory | 8H | 6H | | | 9G | 9G | 2C,3H | 9G | 9G | 9G | 9G | 8G | 8G | 9G | 8G | 9G | 7G | 9C | | | | | | | | |
| Cocklebur | 7H | 9H | | | 9H | — | 3H | 9H | 9H | 8H | 9H | — | 8H | — | 9H | 7H | 7G | 9H | | | | | | | | |
| Velvetleaf | 10C | 5H | | | 2C,8G | 9G | 3G | 2C,8G | 5C,8G | 8G | 8H | — | 8G | 7G | 4C,9G | 9C | 5G | 9C | | | | | | | | |
| Nutsedge | 10E | 0 | | | 0 | 9G | 3G | 2C,5G | 10E | 4G | 5G | 8H | 2G | 0 | 10E | 5G | 3G | 10E | | | | | | | | |
| Giant Foxtail | 5G | 2G | | | 0 | 4G | 0 | 5G | 2G | 2G | 4G | 2G | 4G | 7G | 3G | 3G | 6G | 2C | | | | | | | | |
| | | | | | | | | | | | | | | | | | | | | | | | | | | |
| Barnyardgrass | 4C,9H | 6H | | | 0 | 2C,5G | 2C | 3C,9H | 3C,9H | 3H | 2C,4G | 0 | 0 | 3C,9H | 7G | 3C,9H | 0 | 2G | | | | | | | | |
| Cheatgrass | 10H | 6H | | | 0 | 7G | — | 3C,9H | 3C,9H | 2C,7H | 2C,6G | 0 | 3C,9H | 0 | 6G | 0 | — | 8G | | | | | | | | |
| Wild Oats | 5C,9G | 6G | | | 0 | 2C,5G | 2C | 3C,9H | 5C,8G | 2C,8G | 2C,6G | 3G | 0 | 1C | 2C,7G | 4C,9H | 4G | 2C,8G | | | | | | | | |
| Wheat | 5C,9G | 6G | | | 0 | 5G | 2G | 5G | 4C,9G | 2C,8G | 6G | 3G | 3G | 5G | 5G | 2C,6G | 3C,5G | 7G | | | | | | | | |
| Corn | 4C,9H | 3C,7H | | | 4C,8G | 9G | 5G | 4C,9H | 4C,9H | 2C,8G | 8G | 2G | 2G | 0 | 2C,9G | 3C,9H | 5G | 4C,9H | | | | | | | | |
| Barley | — | — | | | — | — | — | — | — | — | — | — | — | — | — | — | — | — | | | | | | | | |
| Soybean | 4C,6H | 3C,4H | | | 4C,5H | 5G | 2G | 3C,7H | 3C,7H | 2C | 2G | 4C,6H | 3C,5G | 6H | 2C,9H | 2C,5G | 3C,4G | 3C,7H | | | | | | | | |
| Rice | 9H | 9H | | | 0 | 2C,8G | 0 | 9C,9H | 9C,9H | 2C,6G | 2C,6G | 0 | 2G | 2C,8G | 9G | 0 | 3C,5G | 3C,9H | | | | | | | | |
| Sorghum | 5C,9H | 4C,8G | | | 0 | 2C,7G | 0 | 4C,9G | 4C,9G | 3C,5G | 3C,5G | 0 | 7G | 2C | 3C,9G | 0 | 5G | 3C,9H | | | | | | | | |
| Sugar beet | 5C,9G | 4C,9G | | | 5C,9G | 5C,9G | 10C | 10C | 10C | 4C,9G | 5C,9G | 9C | 10C | 9C | 5C,9G | 3C,9G | 5G | 10C | | | | | | | | |
| Cotton | 4C,8G | 4G | | | 8G | 9G | 5G | 9G | 9G | 9G | 8G | 7G | — | 3G | 4G | 4G | 5G | 9G | | | | | | | | |

POSTEMERGENCE

| | Cmpd. 31 | Cmpd. 32 | Cmpd. 33 | Cmpd. 34 | Cmpd. 35 | Cmpd. 36 | Cmpd. 37 | Cmpd. 38 | Cmpd. 39 | Compound 40 | | Compound 41 | | Compound 42 | | Compound 43 | |
|---|---|---|---|---|---|---|---|---|---|---|---|---|---|---|---|---|---|
| | 0.05 | 0.05 | 0.05 | 0.05 | 0.05 | 0.05 | 0.05 | 0.05 | 0.05 | 0.05 | 0.01 | 0.05 | 0.01 | 0.05 | 0.01 | 0.05 | 0.01 |
| Morningglory | 3C,9G | 9C | 10C | 10C | 9G | 9G | 2C,5G | 2C,9G | 2C,5H | 5C,9G | 2C,4G | 10C | 5C,9G | 3G | 6G | 3C,7G | 2C,6G |
| Cocklebur | 3C,9H | 9C | 10C | 10C | 10C | 10C | 3G | 3G | 3G | 5C,9G | 6C,9G | 5C,9G | 3C,9H | 8H | 3G | 3C,8H | 5G |
| Velvetleaf | 3C,9H | 5C,9G | 10C | 10C | 9G | 9C | 2C,7G | 2C,7H | 2C,7H | 9C | 9C | 3C,9H | 9C | 2C,7G | 2G | 3C,7G | 4G |
| Nutsedge | 2C,8G | 4C,8G | 10C | 9G | 6G | 0 | 2C | 0 | 2C | 4C,9G | 3C,9G | 7G | 7G | 8G | 2G | 3C,8G | 3C,7G |
| Crabgrass | 3G | 0 | 2G | 3G | 0 | 0 | 0 | 3G | 0 | 4C,8G | 5C,9G | 7G | 0 | 3G | 0 | 5G | 0 |
| Giant Foxtail | — | 2H | 3G | 7G | 0 | 0 | 0 | 0 | 0 | 9C | 5C,9G | 7G | 3G | 6G | 2G | 7G | 3G |
| Barnyardgrass | 3C,8H | 3C,7H | 6G | 4C,9G | 5G | 3G | 2G | 3C,9H | 3C,9H | 9C | 9C | 4C,9H | 4C,9H | 3C,9H | 2C,5H | 3C,7H | 2H |
| Cheatgrass | 3C,8G | 3G | 2G | 4C,5G | 0 | 0 | 4G | 0 | 0 | 8G | 5C,9G | 2C,6G | 9C | 3C,9G | 7G | 5G | 5G |
| Wild Oats | 3C,9G | 2C,5G | 7G | 8G | 6G | 0 | 0 | 1C | 0 | 9G | 2G | 2C,5G | 4G | 9G | 3G | 9G | 3G |
| Wheat | 5G | 3G | 4G | 6G | 0 | 6G | 4G | 5G | 3G | 7G | 3G | 4C,9G | 3G | 2C,8G | 2G | 7G | 2G |
| Corn | 3C,9H | 4C,9G | 8G | 5C,9G | 4H,6G | 4G | 4G | 2C,4G | 2C,9G | 9G | 3C,9H | 2C,5G | 4C,9G | 2C,8G | 2C,7G | 3C,9G | 2C,7H |
| Barley | — | 4G | 5G | 5G | 0 | 0 | 0 | — | 9G | 2C,8G | 6G | 2C,8G | 0 | 3C,9G | 0 | 2C,5G | 0 |
| Soybean | 3C,9G | 3C,8H | 10C | 10C | 7G | 9G | 2C,6G | 2C,6G | 2C,9G | 4C,9G | 3C,9H | 4C,9G | 4C,9G | 3C,9G | 3C,7G | 3C,7G | 2C,5G |
| Rice | 5C,9G | 4C,9H | 6G | 6G | 7G | 3G | 3G | 2C,8G | 9G | 2C,9G | 3C,8G | 2C,5G | 4C,8H | 7G | 3G | 3C,6G | 4G |
| Sorghum | 3C,8G | 3C,7H | 8G | 9G | 9G | 2G | 3C,9G | 0 | 3G | 5C,9H | 3C,9H | 4C,9G | 4C,9G | 3C,7G | 2C,5G | 5G | 0 |
| Sugar beet | 5C,9G | 3G | 10C | 9G | 9G | 10C | 3C,9H | 9C | 3C,9H | 5C,9H | 4C,8H | 9C | 9C | 2C,5G | 3C,7G | 3C,7G | 3G |
| Cotton | 4C,9H | 5C,9G | 10C | 9G | 9G | 9G | 4C,9G | 4C,9G | 4C,9G | 9C | 4C,9H | 9C | 4C,9G | 10C | 5G | 2C,7G | 3G |

PREEMERGENCE

| | Cmpd. 31 | Cmpd. 32 | Cmpd. 33 | Cmpd. 34 | Cmpd. 35 | Cmpd. 36 | Cmpd. 37 | Cmpd. 38 | Cmpd. 39 | Compound 40 | | Compound 41 | | Compound 42 | | Compound 43 | |
|---|---|---|---|---|---|---|---|---|---|---|---|---|---|---|---|---|---|
| | 0.05 | 0.05 | 0.05 | 0.05 | 0.05 | 0.05 | 0.05 | 0.05 | 0.05 | 0.05 | 0.01 | 0.05 | 0.01 | 0.05 | 0.01 | 0.05 | 0.01 |
| Morningglory | 7H | 8G | 9G | 9G | 9G | 9G | 6G | 7H | 7H | 5G | 2C,3H | 9G | 5H | 6G | 8H | 7G | 7G |
| Cocklebur | 8G | 7H | 9G | 9G | 7G | 9G | 7G | 8H | — | 9H | 3C,7H | 8H | 2C,5H | 3G | 8H | 7H | 7H |
| Velvetleaf | 7H | 8G | 10E | 9G | 3G | 8G | 3G | 8G | 7G | 10E | 5G | 10E | 4G | 2G | 7G | 7G | 7G |
| Nutsedge | 3G | 5G | | 10E | 4G | 3G | 0 | 0 | 0 | 9G | 5G | 9G | 0 | 4G | 0 | 8G | 0 |

TABLE A-continued

| | Compound 44 | | Compound 45 | | Compound 46 | | Compound 47 | | Compound 48 | | Compound 49 | | Compound 50 | | Compound 51 | | Compound 52 | | Compound 0 | |
|---|---|---|---|---|---|---|---|---|---|---|---|---|---|---|---|---|---|---|---|---|---|
| Rate kg/ha | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 | 0.05 | 0.01 |
| Crabgrass | 0 | 2G | 3G | 6G | 3G | 2G | 2C,5G | 0 | 0 | 0 | 2G | 0 | 5G | 5G | 0 | 5G | 5G | 5G | 5G | 5G |
| Giant Foxtail | — | 5G | 3G | 5G | 6G | 2C | 2C,8G | 0 | 0 | 0 | 8G | 4G | 4C,8H | 4C,9H | 0 | 9H | 4G | 6G | 4G | 4G |
| Barnyardgrass | 2G | 5G | 2G | 3G | 2G | 3C | 7G | 0 | 0 | 0 | 3C,9H | 3C,8H | 5C,9H | 5C,9H | 0 | 10C | 3G | 5G | 6G | 3G |
| Cheatgrass | 0 | 2G | 6G | 6G | 4G | 10E | 0 | 0 | 1C | 0 | 9H | 3G | 6C,9H | 6C,9H | 5G | 10C | 6G | 6G | 6G | 3G |
| Wild Oats | 2C,4G | 5G | 10E | 4G | 5G | 8G | 3G | 0 | 3G | 0 | 7G | 0 | 2C,8G | 2C,8G | 2C,9G | 7G | 6G | 6G | 6G | 2G |
| Wheat | 4G | 3G | 8G | 2G | 8G | 8G | 2G | 0 | 2C | 0 | 7G | 3C,8H | 5C,9H | 4C,9G | 4G | 2C,8G | 3G | 6G | 3G | 0 |
| Corn | 2C,5G | 3C,8H | 8G | 8G | 8G | 9G | 2H | 0 | 2G | 0 | 4C,9H | 3C,8H | 2C,9H | 3C,9H | 3C,7H | 3C,9H | 2G | 7G | 2G | 4G |
| Barley | — | 9G | 3G | 3G | 7G | 8G | 0 | 0 | 3H | 0 | 6C,9G | 8G | 5C,9H | 5C,9H | 9G | 3C,9H | 7G | 8H | 7G | 2G |
| Soybean | 2C,3G | 3C,5G | 6G | 6G | 9G | 7G | 2G | 3C,7G | 0 | 0 | 3C,7H | 3C,4H | 9H | 9G | 3C,9G | 5C,9H | 2C,2H | 3C,7H | 2C,2H | 0 |
| Rice | 3C,7G | 3C,7H | 10E | 9G | 10E | 8G | 2G | 2C | 2C,2H | 0 | 9H | 3C,7H | 10E | 3C,6H | 9G | 3C,9H | 3G | 8H | 0 | 5G |
| Sorghum | 3C,3G | 2C,8H | 8G | 8G | 9G | 9G | 3G | 3G | 2C | 0 | 9H | 4C,9H | 3C,8H | 3C,7H | 7G | 3C,9H | 2G | 3C,8G | 5G | 3G |
| Sugar beet | 3C,8G | 8G | 9G | 8G | 9G | 10E | 9G | 4G | 3G | 0 | 10E | 4C,9H | 4C,9G | 8H | 8G | 3C,8H | 6G | 3C,8G | 5G | 5G |
| Cotton | 7G | 7H | 9G | 9G | 9G | 9G | 9G | 3C,5G | 9G | 4C,9G | 4C,9G | 2C,9G | 2C,9G | 3C,8H | 9G | 3C,9G | 7G | 6G | 5G | 6G |

| | POSTEMERGENCE |
|---|---|
| Morningglory | 10C 10C 9C 9C 9C 3C,7G 2C,5G 5G 5C,9G 4C,9G 10C 10C 10C 10C 9C 9G 9C 9G 10C 10C 8G 0.05 |
| Cocklebur | 10C 10C 10C 10C 9H 3C,9H 2C,8G 8H 9C 0 10C 10C 9H 9H 10C 9H 10C 9H — 0.05 |
| Velvetleaf | 9C 9C 9C 9C 0 3C,8H 7G 4G 7C 4C,8H 10C 10C 10C 10C 10C 9C 10C 9C 7G 0.05 |
| Nutsedge | 3C,7G 3C,7G 8G 8G 3C,7G 0 0 0 0 0 10E 10E 10E 10E 10E 9C 9C 5C,9G 4C,9G 0.05 |
| Crabgrass | 4C,9G 4C,9G 3G 3G 2G 2C,5G 0 0 0 0 5G 7G 3C,7G 3C,7G 3C,7G 3C,7G 3C,7G 3C,7G 3C,5G 3C,3G 0.05 |

PREEMERGENCE

| Giant Foxtail | 6G 0 7G 3G 0 3C,6H 0 0 2G 0 7G 3G 4C,9G 4G 3C,9H 4G 9G 0 2G 0.05 |
| Barnyardgrass | 3C,8G 3G 2C,8G 3C,5G 2G 2C,5G 2G 0 2H 0 8H 9C 3C,9H 5C,9H 3C,9H 3C,7H 8H 3C,7H 2G 0.05 |
| Cheatgrass | 5C,9G 9H 5C,9H 3C,6G 3C,8H 3C,6H 0 0 0 0 9C 9C 6C,9G 4C,9G 4C,9G 9G 7G 4G 0.05 |
| Wild Oats | 4C,9G 6G 4C,8G 2C,6G 6G 6G 2G 0 0 0 9C 1C 9G 5G 9G 3C,9G 4G 0.05 |
| Wheat | 3C,7G 4G 2C,8G 2C,6G 3G 3G 6G 0 0 0 7G 9G 6C,9G 3C,6H 2C,9G 8G 6G 0.05 |
| Corn | 2C,7G 0 9C 3C,9G 3C,8H 2C,5G 5G 5G 4G 0 5C,9G 3C,7H 9G 5G 5C,9G 4C,9H 2C,7G 2C,5G 0.05 |
| Barley | 9G 3C,9H 2C,9G 5G 3G 3G 2C,8H 1H 5C,9G 0 8G 2C,5H 8G 8G 2C,9G 7G 2C,7G 0 0.05 |
| Soybean | 8G 0 4C,9G 3C,7G 3C,8H 3C,7G 3G 8H 6G 0 9C 3C,7H 3C,6H 3C,8H 9C 4C,9H 6G 0.05 |
| Sorghum | 3C,7G 6H 5C,9G 2C,6H 3C,8H 7G 4G 2C,2G 2G 4C,9G 7G 7G 3C,8G 3C,8H 9G 7H 6G 0.05 |
| Rice | 4C,9G 5G 2C,9H 8H 3C,6G 3G 0 0 3C,7H 0 3C,9H 7H 3C,8H 3C,8H 3C,9H 4C,9H 9G 0.05 |
| Sugar beet | 4C,9H 2C,5G 3C,8H 3C,8G 3C,6G 3G 4G 3C,5G 2G 0 9H 3C,9G 3C,9H 3C,9H 9H 9H 9H 5C,9G 0.05 |
| Cotton | 10E 7G 5C,9G 3C,9H 3C,6G 7G 8G 4C,9G 5G 5G 9C 9G 9C 9C 9C 9C 10C 10C 6G |

TABLE A-continued

| | Compound 53 | | Compound 54 | | Compound 55 | | Compound 56 | | Cmpd. 57 | Cmpd. 58 | Cmpd. 59 | Cmpd. 60 | Cmpd. 61 | Compound 62 | | Compound 63 | | Compound 64 | | Compound 65 |
|---|---|---|---|---|---|---|---|---|---|---|---|---|---|---|---|---|---|---|---|---|
| Rate kg/ha | 0.01 | 0.05 | 0.01 | 0.05 | 0.01 | 0.05 | 0.01 | 0.05 | 0.05 | 0.05 | 0.05 | 0.05 | 0.05 | 0.01 | 0.05 | 0.01 | 0.05 | 0.01 | 0.05 | 0.05 |
| POSTEMERGENCE | | | | | | | | | | | | | | | | | | | | |
| Morningglory | 10C | 10C | 10C | 10C | 5C,9G | 5C,9G | 9C | 4C,9G | 10C | 3C,7G | 3C,7H | 1C | 3C,7G | 10C | 10C | 3C,7G | 2C,7G | 1H | 3C,7G |
| Cocklebur | 2C,9H | 10C | 9C | 9C | 5C,9H | 6G | — | 10C | 4G | 4C,9H | 4G | 3C,9G | 1H | 2C,7H | 2C,9H | 3H | 3G | 0 | 9C |
| Velvetleaf | 8H | 10C | 10C | 9C | 7G | 4C,9H | 7G | 9C | 5G | 4C,9G | 3C,8H | 2C,5G | 9C | 10C | 9C | 9C | 10C | 2C,8H | 9C |
| Nutsedge | 2C,5G | 9G | 9G | 5G | 0 | 5G | 5G | 5C,9G | 0 | 4C,9G | 2C,5G | 3C,5G | 4G | 2C,8G | 4G | 0 | 0 | 0 | 2G |
| Crabgrass | 0 | 2G | 5G | 0 | 0 | 5G | 7G | 5G | 0 | 0 | 0 | 3C,7G | 0 | 4G | 2G | 0 | 0 | 0 | 2C,4G |
| Giant Foxtail | 0 | 5G | 0 | 4G | 0 | 0 | — | 4G | 4G | 2C,6G | 2C,6G | 9C | 3G | 0 | 5G | 0 | 5G | 2G | 3C,9H |
| Barnyardgrass | 3C,3H | 9C | 3C,4H | 9H | 3C,7H | 5C,9H | 2C,7H | 4H | 4H | 4C,9H | 3C,6H | 5C,9G | 9H | 3G | 8H | 2H | 8G | 0 | 4C,9G |
| Cheatgrass | 2G | 5G | 2G | 0 | 0 | 2C,5G | 3C,7G | 3C,7G | 0 | 6C,9H | 2G | 2C,9G | 0 | 2G | 7G | 3G | 2C,5G | 0 | 3C,9G |
| Wild Oats | 2C | 5G | 5G | 3C,3G | 0 | 2C,5G | 2C,5G | 3C,5G | 2G | 0 | 0 | 4C,9G | 2G | 0 | 7G | 0 | 2C,4G | 0 | 4C,9G |
| Wheat | 0 | 3G | 3G | 4G | 0 | 0 | 0 | 0 | 0 | 8G | 3G | 9G | 4G | 2C,7G | 0 | 0 | 0 | 0 | 3C,9G |
| Corn | 2H | 2C,9H | 4G | 2C,5H | 0 | 4C,9H | 0 | 4C,9H | 8H | 3C,9H | 3C,8H | 5C,9G | 4C,9H | 4C,9H | 5H | 0 | 2C,7G | 2C | 4C,9G |
| Barley | 0 | 4G | 2G | 2C | 0 | 3C,6H | — | 9C | 0 | 9C | 3G | 9C | 4G | 4G | 2G | 0 | 0 | 0 | 3C,8G |
| Soybean | 2C,8G | 9C | 5C,9G | 5C,9G | 4C,9G | 5C,9G | 4C,9G | 3G | 4C,9G | 3H,6G | 5C,9H | 9C | 2C,5H | 2C,5H | 3C,7H | 3H | 2C,7G | 3C,4G | 9C |
| Rice | 2G | 5C,9G | 6G | 4C,9G | 5G | 5C,9G | 5C,9G | 3C,4G | 3G | 9C | 9C | 3C,4G | 3C,7G | 2G | 2C,5G | 0 | 5G | 0 | 5C,9G |
| Sorghum | 2C,8H | 3C,8G | 3G | 3C,7G | 2G | 9H | 3C,7G | 9H | 3C,4G | 4C,9G | 4C,9G | 3C,7G | 2C,8G | 4G | 6G | 4G | 9C | 1C,6G | 2C,9G |
| Sugar beet | 9C | 10C | 10C | 5C,9G | 4C,8G | 5C,9G | 5C,9G | 9C | 9C | 4C,9H | 9C | 9C | 8G | 2C,7G | 3C,9H | 3C,8H | 10E | 3C,9G | 9C |
| Cotton | 10C | 4C,9G | 4C,8H | 4C,8G | 4C,9G | 9G | 4G | 4C,8H | 5C,9G | 3C,8H | 3C,8H | 3C,6G | 10C | 9H | 9C | 10C | 0 | 2C,7H | 9C |
| PREEMERGENCE | | | | | | | | | | | | | | | | | | | | |
| Morningglory | 7H | 9G | 9G | 9H | 8H | 9G | 8G | 0 | 0 | 9G | 0 | 5G | 4G | 4G | 3G | 0 | 6G |
| Cocklebur | 7H | 9G | 3C,8H | — | 3C,5H | 5G | 7G | 0 | 1H | 9H | 0 | 3G | 3G | 5H | 0 | 0 | 9H |
| Velvetleaf | 5G | 4C,9G | 3C,5H | 6H | — | 5G | 7G | 4C,9G | 4G | 4C,9G | 0 | 8G | 3G | 0 | 2H | 0 | 9G |
| Nutsedge | 0 | 10E | 5C,9G | 4C,9G | 5G | 5G | 3G | 10E | 0 | 0 | 0 | 0 | 0 | 0 | 0 | 0 | 5G |
| Crabgrass | 0 | 0 | 0 | 7G | 3G | 3G | 3G | 0 | 0 | 0 | 0 | 3G | 2G | 0 | 2H | 0 | 0 |
| Giant Foxtail | 2G | 3C,5G | 4G | 2C,7G | 3G | — | — | 4G | 0 | 0 | 2G | 10H | 7G | 0 | 2G | 0 | 3C,7H |
| Barnyardgrass | 7G | 3C,7G | 5G | 5C,9H | 3C,7G | 9G | 2G | 3C,6G | 0 | 0 | 0 | 3G | 3G | 0 | 0 | 0 | 9H |
| Cheatgrass | 0 | 6G | 5G | 2C,2G | 3G | 9G | 2C,6G | 3G | 0 | 0 | 0 | 5G | 5G | 0 | 5G | 0 | 8G |
| Wild Oats | 1C | 2C,6G | 0 | 4G | 3G | 0 | 0 | 2C,5G | 0 | 0 | 0 | 5G | 0 | 0 | 8G | 0 | 8G |
| Wheat | 5G | 3C,7G | 7G | 2C,7G | 5G | 3C,7G | 3C,6G | 5G | 4G | 0 | 0 | 3G | 2G | 0 | 0 | 0 | 3C,9G |
| Corn | 3G | 9G | 3G | 9H | 5G | — | 3C,4H | 2C,4G | 8G | 0 | 0 | 0 | 3G | 0 | 3G | 0 | 9G |
| Barley | 5H | 5G | 9H | 9H | 9H | 6H | 3C,7G | 3C,6G | 0 | 0 | 0 | 4H | 3G | 5H | 3C,9G | 0 | 3C,8G |
| Soybean | 5G | 4C,9H | 7H | 10E | 10E | 10E | 3C,7G | 3C,6H | 4H | 2C,2H | 2C,2H | 2C,8G | 0 | 0 | 9H | 0 | 9H |
| Rice | 8G | 3C,8G | 3C,7G | 9H | 3C,5G | 6H | 3C,4H | 8G | 0 | 3C,8G | 3C,8G | 2C,5G | 4G | 0 | 3C,9H | 0 | 3C,9H |
| Sorghum | 8G | 9C | 9C | 5C,9G | 4C,8G | 10E | 3C,7G | 2C,4G | 8G | 3C,6G | 3C,6G | 0 | 8G | 7G | 0 | 0 | 9C |
| Sugar beet | 8G | 4C,9G | 4C,8H | 4C,8G | 4C,7G | 5C,9G | 3C,7G | — | 0 | 0 | 0 | 7G | 5G | 5G | 10E | — | 9G |
| Cotton | | | | | 4C,9G | | 4G | 9G | | 2H | | 9G | | | | | | | |

| | Compound 65 | Compound 66 | | Compound 67 | | Cmpd. 68 | Cmpd. 69 | Compound 70 |
|---|---|---|---|---|---|---|---|---|
| Rate kg/ha | 0.01 | 0.05 | 0.01 | 0.05 | 0.01 | 0.05 | 0.05 | 0.01 |
| POSTEMERGENCE | | | | | | | | |
| Morningglory | 2G | 10C | 3C,8G | 10C | 2C,8G | 5C,9G | 2C,3G | 3C,7G |
| Cocklebur | 4G | 9C | 5G | 10C | 7G | 5C,9G | 3C,9H | 2C,5G |
| Velvetleaf | 9C | 10C | 10C | 10C | 10C | 3C,5G | 2G | 4G |
| Nutsedge | 0 | 9G | 2C,8G | 9G | 3C,6G | 2C,5G | 0 | 3G |
| Crabgrass | 0 | 2C,6G | 3G | 4G | 0 | 0 | 2G | 0 |

TABLE A-continued

| | | | | | | | | | |
|---|---|---|---|---|---|---|---|---|---|
| Giant Foxtail | 0 | 8G | 2C,4G | 2C,7G | 3G | — | — | 0 | 0 |
| Barnyardgrass | 2C,5H | 9H | 3C,8H | 3C,8H | 2C,3H | 0 | 2G | 0 | 0 |
| Cheatgrass | 9G | 8G | 2C,8G | 2C,9G | 4G | 0 | 0 | 0 | 0 |
| Wild Oats | 3C,6G | 3C,9G | 2C,3G | 2C,3G | 0 | 0 | 0 | 0 | 0 |
| Wheat | 4G | 9G | 2G | 2G | 0 | 0 | 0 | 0 | 0 |
| Corn | 3C,6G | 3C,9H | 3C,9H | 3C,7H | 3G | 0 | 0 | 0 | 0 |
| Barley | 0 | 3C,9G | 3G | 3G | 3G | 0 | 0 | 0 | 0 |
| Soybean | 5C,9G | 9C | 9C | 9C | 5C,9G | 2H | 3C,8H | 3C,5H |
| Rice | 3C,9G | 4C,9G | 3C,8G | 2C,7G | 2G | 0 | 0 | 0 | 0 |
| Sorghum | 3C,8G | 9G | 5C,9G | 3C,9G | 3C,7G | 0 | 0 | 1H | 0 |
| Sugar beet | 9C | 10C | 10C | 10C | 10C | 2C,4G | 3G | 1H | 0 |
| Cotton | 5C,9G | 10C | 10C | 10C | 10C | 2C,4G | 5G | 1H | 0 |

| | | | | PREEMERGENCE | | | | | |
|---|---|---|---|---|---|---|---|---|---|
| Morningglory | 2H | 8G | 9G | 9G | 6G | 0 | 2H | 0 |
| Cocklebur | 8G | 3H | 9H | 9H | 0 | — | 3H | — |
| Velvetleaf | 3G | 9G | 9G | 9G | 3G | 0 | 5G | 0 |
| Nutsedge | 0 | 10E | 6G | 10E | 4G | 0 | 0 | 0 |
| Crabgrass | 0 | 1C | 0 | 0 | 0 | — | 0 | 0 |
| Giant Foxtail | 0 | 3C,7G | 3C,7G | 3C,7G | 2C,4G | 0 | 2C | 0 |
| Barnyardgrass | 0 | 9H | 9H | 9H | 2C,3G | 0 | 3G | 0 |
| Cheatgrass | 5G | 3C,9H | 9H | 3C,9H | 6G | 0 | 0 | 0 |
| Wild Oats | 2C,7G | 3C,8G | 3C,6G | 3C,9H | 0 | 0 | 0 | 0 |
| Wheat | 3G | 8G | 6G | 2C,6G | 0 | — | 0 | 0 |
| Corn | 4G | 2U,9G | 2C,8G | 2C,7G | 7G | 0 | 2C | 0 |
| Barley | 8G | 7G | 7G | 4G | 2G | 0 | 3G | 0 |
| Soybean | 5G | 3C,8H | 3C,8H | 3C,8H | 6G | 1C | 0 | 0 |
| Rice | 2C,8H | 3C,9H | 3C,9H | 7G | 3C | 3C | 0 | 0 |
| Sorghum | 2C,3G | 3C,9G | 3C,9H | 8G | 3C,7G | 0 | 3G | 0 |
| Sugar beet | 4C,9G | 9C | 5C,9G | 9C | 5G | 3G | 3G | 5G |
| Cotton | 8G | 9G | 9G | 9G | 2G | 0 | — | — |

What is claimed is:
1. A compound of the formula:

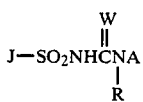

wherein

J is

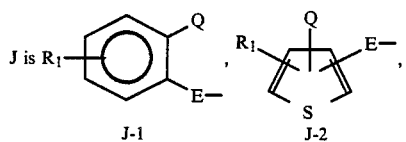

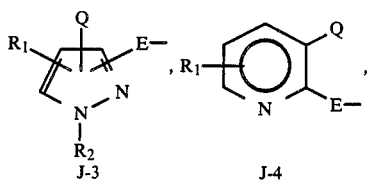

W is O or S;
R is H or CH$_3$;
E is a single bond, CH$_2$ or O;
Q is a saturated 5- or 6-membered heterocyclic ring, bonded through carbon or nitrogen, containing a carbonyl group and 2-3 heteroatoms selected from the group consisting of 0-2 oxygen, 0-2 sulfur or 0-2 nitrogen; a 5-membered heterocyclic ring, bonded through carbon or nitrogen, containing a carbonyl group and 2-3 heteroatoms selected from the group consisting of 0-2 oxygen, 0-2 sulfur or 1-3 nitrogen and containing one endocyclic double bond; a 6-membered heterocyclic ring, bonded through carbon or nitrogen, containing a carbonyl group and 2-3 heteroatoms selected from the group consisting of 0-2 oxygen, 0-2 sulfur or 1-3 nitrogen and containing one or two endocyclic double bonds; or a 5-membered heterocyclic ring, bonded through carbon or nitrogen, containing two adjacent carbonyl groups and 2 heteroatoms selected from the group consisting of 0-1 oxygen, 0-1 sulfur, or 1-2 nitrogen and containing onr endocyclic double bond, said Q value may be substituted or unsubstituted wherein the substituent groups are selected from the group consisting of C$_1$-C$_4$ alkyl, C$_1$-C$_4$ haloalkyl, C$_3$-C$_4$ alkenyl, C$_3$-C$_4$ haloalkenyl, C$_3$-C$_4$ alkynyl, C$_3$-C$_4$ haloalkynyl, C$_1$-C$_3$ cyanoalkyl, C$_2$-C$_4$ alkoxyalkyl, C$_2$-C$_4$ alkylthioalkyl, C$_2$-C$_4$ alkylcarbonyl, C$_3$-C$_4$ alkylcarbonylalkyl, C$_1$-C$_4$ alkyl substituted with OH or NH$_2$, C$_2$-C$_4$ alkylaminoalkyl, C$_3$-C$_4$ dialkylaminoalkyl, CH$_2$CH(OCH$_3$)$_2$.

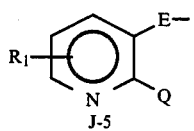

C(O)N(CH$_3$)$_2$, P(O)(OC$_1$-C$_2$ alkyl)$_2$, P(S)(OC$_1$-C$_2$ alkyl)$_2$ or C$_1$-C$_2$ alkyl substituted with C$_1$-C$_2$ alkoxycarbonyl;

R$_1$ is H, C$_1$-C$_3$ alkyl, C$_1$-C$_3$ haloalkyl, halogen, nitro, C$_1$-C$_3$ alkoxy, SO$_2$NR$_a$R$_b$, C$_1$-C$_3$ alkylthio, C$_1$-C$_3$ alkylsulfinyl, C$_1$-C$_3$ alkylsulfonyl, CH$_2$CN, CN, CO$_2$R$_c$, C$_1$-C$_3$ haloalkoxy, C$_1$-C$_3$ haloalkylthio, C$_2$-C$_4$ alkoxyalkyl, C$_2$-C$_4$ alkylthioalkyl, CH$_2$N$_3$ or NR$_d$R$_e$;

R$_a$ is H, C$_1$-C$_4$ alkyl, C$_2$-C$_3$ cyanoalkyl, methoxy or ethoxy;

R$_b$ is H, C$_1$-C$_4$ alkyl or C$_3$-C$_4$ alkenyl; or

R$_a$ and R$_b$ may be taken together as —(CH$_2$)$_3$—, —(CH$_2$)$_4$—, —(CH$_2$)$_5$— or —CH$_2$CH$_2$OCH$_2$CH$_2$—;

R$_c$ is C$_1$-C$_4$ alkyl, C$_3$-C$_4$ alkenyl, C$_3$-C$_4$ alkynyl, C$_2$-C$_4$ haloalkyl, C$_2$-C$_3$ cyanoalkyl, C$_5$-C$_6$ cycloalkyl, C$_4$-C$_7$ cycloalkylalkyl or C$_2$-C$_4$ alkoxyalkyl;

R$_d$ and R$_e$ are independently H or C$_1$-C$_2$ alkyl;

A is

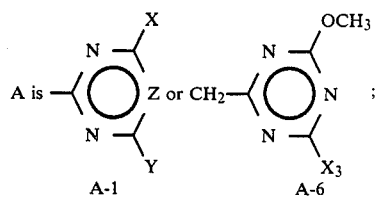

X is H, C$_1$-C$_4$ alkyl, C$_1$-C$_4$ alkoxy, C$_2$-C$_4$ haloalkoxy, C$_1$-C$_4$ haloalkyl, C$_1$-C$_4$ haloalkylthio, C$_1$-C$_4$ alkylthio, C$_2$-C$_5$ alkoxyalkyl, C$_2$-C$_5$ alkoxyalkoxy, amino, C$_1$-C$_3$ alkylamino, di(C$_1$-C$_3$ alkyl)amino or C$_3$-C$_5$ cycloalkyl;

Y is H, C$_1$-C$_4$ alkyl, C$_1$-C$_4$ alkoxy, C$_2$-C$_4$ haloalkoxy, C$_1$-C$_4$ haloalkylthio, C$_1$-C$_4$ alkylthio, C$_2$-C$_5$ alkoxyalkyl, C$_2$-C$_5$ alkoxyalkoxy, amino, C$_1$-C$_3$ alkylamino, di(C$_1$-C$_3$ alkyl)amino, C$_3$-C$_4$ alkenyloxy, C$_3$-C$_4$ alkynyloxy, C$_2$-C$_5$ alkylthioalkyl, C$_1$-C$_4$ haloalkyl, C$_2$-C$_4$ alkynyl, azido, cyano, C$_2$-C$_5$ alkylsulfinylalkyl, C$_2$-C$_5$ alkylsulfonylalkyl,

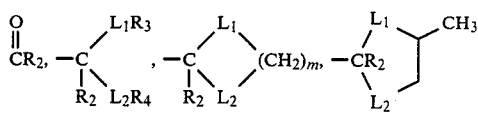

or N(OCH$_3$)CH$_3$;
m is 2 or 3;
L$_1$ and L$_2$ are independently O or S;
R$_2$ is H or C$_1$-C$_3$ alkyl;
R$_3$ and R$_4$ are independently C$_1$-C$_3$ alkyl;
Z is N; and
X$_3$ is CH$_3$ or OCH$_3$;
and their agriculturally suitable salts; provided that
(a) when Q contains 2 heteroatoms selected from 0-2 oxygen and 0-2 sulfur, said heteroatoms are not bonded directly to one another, and when Q contains 3 nitrogen heteroatoms, only two of these may be bonded directly together;

(b) when J is J-2 or J-3, the substituent Q and the sulfonylurea bridge are on adjacent carbon atoms;

(c) when E is O, then J is J-1 and W is O;

(d) when W is S, then R is H, A is A-1, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or 1,3-dioxolan-2-yl;

(e) when the total number of carbons of X and Y is greater than four, then the number of carbons of $R_1$ must be less than or equal to two, and the number of carbons of the substituents on Q must be less than or equal to two; and (f) when Q is bound through nitrogen and contains 2-heteroatoms and one carbonyl group, and said heteroatoms are bound through the carbonyl, then J is other than J-1.

2. A compound of claim 1 wherein Q is selected from

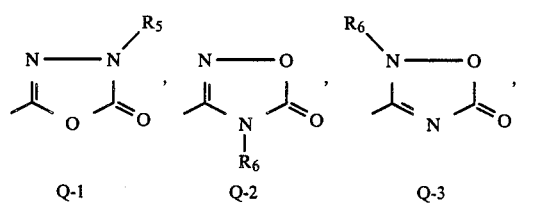

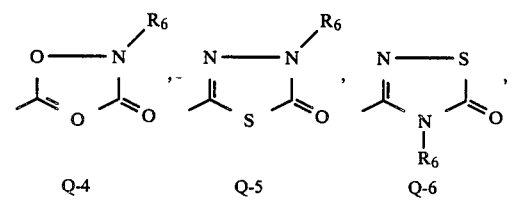

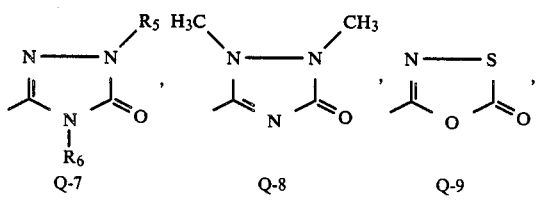

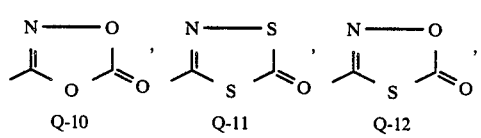

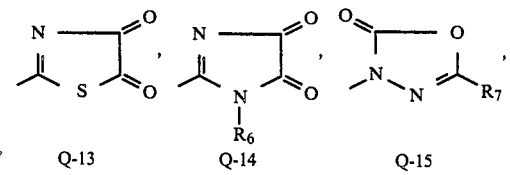

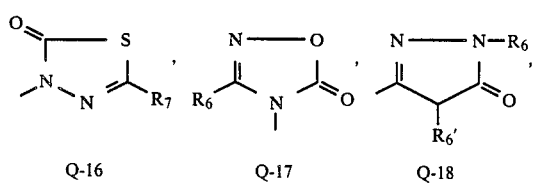

-continued

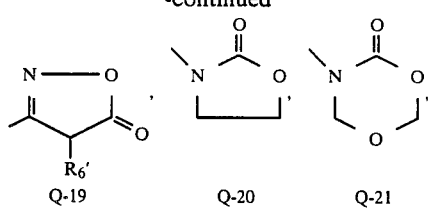

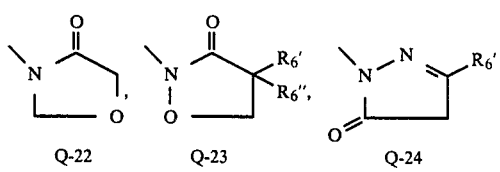

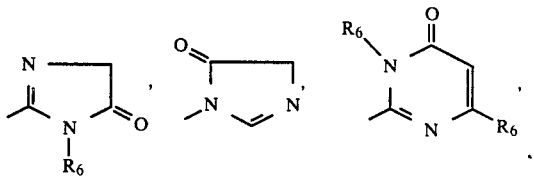

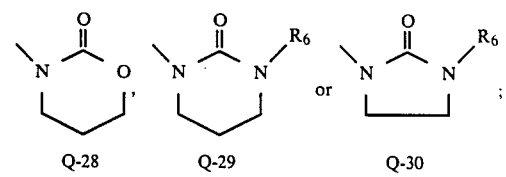

wherein $R_5$ is H, $C_1-C_4$ alkyl, $CH_2CH=CH_2$, $CH_2CH=CHCH_3$, $CH_2C\equiv CH$, $CH_2C\equiv CCH_3$, $CH_2CN$, $CH_2CO_2(C_1-C_2$ alkyl), $CH(CH_3)CO_2(-C_1-C_2$ alkyl), $CF_2H$, $C_2-C_3$ alkyl substituted with 1-3 atoms of F or Cl, $CH_2OCH_3$, $CH_2OCH_2CH_3$, $CH_2CH_2OCH_3$, or $CH_2CH_2OCH_2CH_3$;

$R_6$ is $C_1-C_3$ alkyl;

$R_6'$ and $R_6''$ are independently H or $C_1-C_2$ alkyl; and $R_7$ is H, $C_1-C_4$ alkyl, $C_1-C_3$ haloalkyl or $CH_2CH=CH_2$.

3. Compounds of claim 1 where E is a single bond.

4. Compounds of claim 1 where E is $CH_2$, and W is O.

5. Compounds of claim 1 where E is O.

6. Compounds of claim 3 where Q is

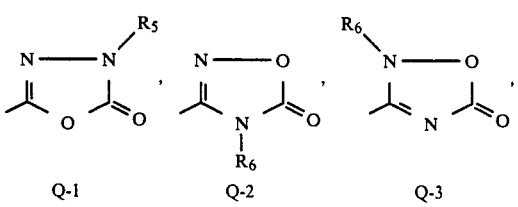

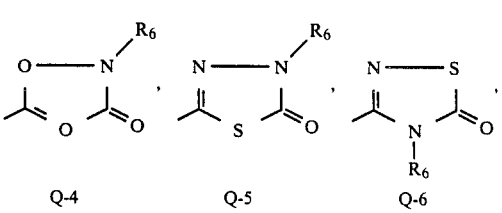

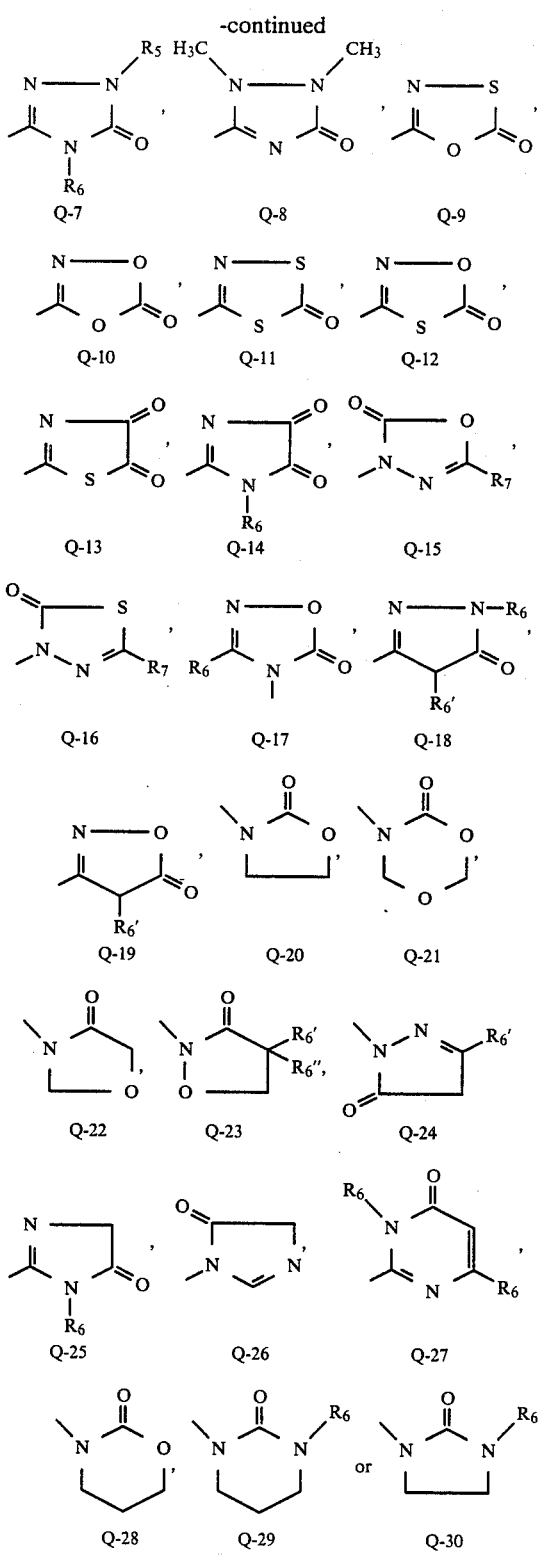

wherein
R₅ is H, C₁–C₄ alkyl, CH₂CH=CH₂, CH₂CH=CHCH₃, CH₂C≡CH, CH₂C≡CCH₃, CH₂CN, CH₂CO₂(C₁–C₂ alkyl), CH(CH₃)CO₂(C₁–C₂ alkyl), CF₂H, C₂–C₃ alkyl substituted with 1–3 atoms of F or Cl, CH₂OCH₃, CH₂OCH₂CH₃, CH₂CH₂OCH₃, or CH₂CH₂OCH₂CH₃;
R₆ is C₁–C₃ alkyl;

R₆′ and R₆″ are independently H or C₁–C₂ alkyl; and
R₇ is H, C₁–C₄ alkyl, C₁–C₃ haloalkyl or CH₂CH=CH₂.

7. Compounds of claim 6 where
R₁ is H, F, Cl, Br, C₁–C₂ alkyl, C₁–C₃ alkoxy, C₁–C₃ alkylthio, or C₁–C₂ alkyl, C₁–C₃ alkoxy or C₁–C₃ alkylthio substituted with 1–3 atoms of F, Cl, or Br;
X is C₁–C₂ alkyl, C₁–C₂ alkoxy, CH₂F, CF₃, OCH₂CH₂F, OCH₂CHF₂, OCH₂CF₃, CH₂Cl or CH₂Br; and
Y is H, C₁–C₂ alkyl, C₁–C₂ alkoxy, CH₂OCH₃, CH₂OCH₂CH₃, NHCH₃, N(OCH₃)CH₃, N(CH₃)₂, CF₃, SCH₃, OCH₂CH=CH₂, OCH₂C≡CH, OCH₂CH₂OCH₃, CH₂SCH₃,

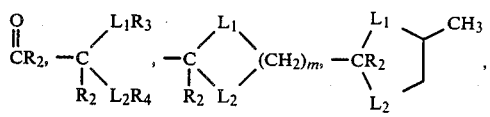

SCF₂H, cyclopropyl, OCF₂H, SCF₂H, cyclopropyl, C≡CH or C≡CCH₃.
8. Compounds of claim 7 where A is A-1.
9. Compounds of claim 8 where J is J-1.
10. Compounds of claim 8 where J is J-2.
11. Compounds of claim 8 where J is J-3.
12. Compounds of claim 8 where J is J-4.
13. Compounds of claim 8 where J is J-5.
14. Compounds of claim 8 where
J is J-1;
R₁ is H, Cl, CH₃ or OCH₃;
X is CH₃, or OCH₃; and
Y is CH₃, OCH₃, C₂H₅, CH₂OCH₃, NHCH₃, CH(OCH₃)₂ or cyclopropyl.
15. Compounds of claim 14 where Q is Q-1.
16. Compounds of claim 14 where Q is Q-2.
17. Compounds of claim 14 where Q is Q-3.
18. Compounds of claim 14 where Q is Q-4.
19. Compounds of claim 14 where Q is Q-5.
20. Compounds of claim 14 where Q is Q-6.
21. Compounds of claim 14 where Q is Q-7.
22. Compounds of claim 14 where Q is Q-8.
23. Compounds of claim 14 where Q is Q-9.
24. Compounds of claim 14 where Q is Q-10.
25. Compounds of claim 14 where Q is Q-11.
26. Compounds of claim 14 where Q is Q-12.
27. Compounds of claim 4 where
R is H;
J is J-1;
R₁ is H;
A is A-1;
X is CH₃, OCH₃, or OCH₂CH₃,
Y is CH₃, OCH₃, C₂H₅, CH₂OCH₃, NHCH₃, CH(OCH₃)₂ or cyclopropyl and Q is

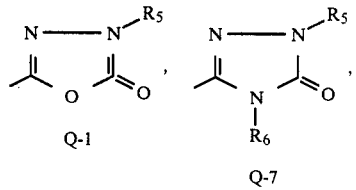

-continued

Q-10, Q-15 structures wherein
R$_5$ is H, C$_1$-C$_4$ alkyl, CH$_2$CH=CH$_2$, CH$_2$CH=CHCH$_3$, CH$_2$C≡CH, CH$_2$C≡CCH$_3$, CH$_2$CN, CH$_2$CO$_2$(C$_1$-C$_2$ alkyl), CH(CH$_3$)CO$_2$(C$_1$-C$_2$ alkyl), CF$_2$H, C$_2$-C$_3$ alkyl substituted with 1-3 atoms of F or Cl, CH$_2$OCH$_3$, CH$_2$OCH$_2$CH$_3$, CH$_2$CH$_2$OCH$_3$, or CH$_2$CH$_2$OCH$_2$CH$_3$;
R$_6$ is C$_1$-C$_3$ alkyl;
R$_7$ is H, C$_1$-C$_4$ alkyl, C$_1$-C$_3$ haloalkyl or CH$_2$CH=CH$_2$.

28. Compounds of claim 5 where
R is H;
J is J-1;
R$_1$ is H;
A is A-1;
X is CH$_3$, OCH$_3$, or OCH$_2$CH$_3$;
Y is CH$_3$, OCH$_3$, C$_2$H$_5$, CH$_2$OCH$_3$, NHCH$_3$, CH(OCH$_3$)$_2$ or cyclopropyl and Q is Q-1, Q-7, Q-10, Q-15 structures wherein
R$_5$ is H, C$_1$-C$_4$ alkyl, CH$_2$CH=CH$_2$, CH$_2$CH=CHCH$_3$, CH$_2$C≡CH, CH$_2$C≡CCH$_3$, CH$_2$CN, CH$_2$CO$_2$(C$_1$-C$_2$ alkyl), CH(CH$_3$)CO$_2$(C$_1$-C$_2$ alkyl), CF$_2$H, C$_2$-C$_3$ alkyl substituted with 1-3 atoms of F or Cl, CH$_2$OCH$_3$, CH$_2$OCH$_2$CH$_3$, CH$_2$C$_2$OCH$_3$, or CH$_2$CH$_2$OCH$_2$CH$_3$;
R$_6$ is C$_1$-C$_3$ alkyl;
R$_7$ is H, C$_1$-C$_4$ alkyl, C$_1$-C$_3$ haloalkyl or CH$_2$CH=CH$_2$.

29. The compound of claim 1 which is 2-(4,5-dihydro-4-methyl-5-oxo-1,3,4-oxadiazol-2-yl)-N-[(4-methoxy-6-methyl-1,3,5-triazin-2-yl)aminocarbonyl]benzenesulfonamide.

30. A composition suitable for controlling the growth of undesired vegetation which comprises an effective amount of a compound of claim 1 and at least one of the following: surfactant, solid or liquid diluent.

31. A composition suitable for controlling the growth of undesired vegetation which comprises an effective amount of a compound of claim 2 and at least one of the following: surfactant, solid or liquid diluent.

32. A composition suitable for controlling the growth of undesired vegetation which comprises an effective amount of a compound of claim 3 and at least one of the following: surfactant, solid or liquid diluent.

33. A composition suitable for controlling the growth of undesired vegetation which comprises an effective amount of a compound of claim 4 and at least one of the following: surfactant, solid or liquid diluent.

34. A composition suitable for controlling the growth of undesired vegetation which comprises an effective amount of a compound of claim 5 and at least one of the following: surfactant, solid or liquid diluent.

35. A composition suitable for controlling the growth of undesired vegetation which comprises an effective amount of a compound of claim 6 and at least one of the following: surfactant, solid or liquid diluent.

36. A method for controlling the growth of undesired vegetation which comprises applying to the locus to be protected an effective amount of a compound of claim 1.

37. A method for controlling the growth of undesired vegetation which comprises applying to the locus to be protected an effective amount of a compound of claim 2.

38. A method for controlling the growth of undesired vegetation which comprises applying to the locus to be protected an effective amount of a compound of claim 3.

39. A method for controlling the growth of undesired vegetation which comprises applying to the locus to be protected an effective amount of a compound of claim 4.

40. A method for controlling the growth of undesired vegetation which comprises applying to the locus to be protected an effective amount of a compound of claim 5.

41. A method for controlling the growth of undesired vegetation which comprises applying to the locus to be protected an effective amount of a compound of claim 6.

* * * * *